(12) United States Patent
Shoemaker et al.

(10) Patent No.: US 9,452,186 B2
(45) Date of Patent: *Sep. 27, 2016

(54) ENHANCED STEM CELL COMPOSITION

(71) Applicant: FATE THERAPEUTICS, INC., San Diego, CA (US)

(72) Inventors: Dan Shoemaker, San Diego, CA (US); David Robbins, Temecula, CA (US); John D. Mendlein, Encinitas, CA (US); Caroline Desponts, La Jolla, CA (US)

(73) Assignee: Fate Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/362,386

(22) PCT Filed: Nov. 29, 2012

(86) PCT No.: PCT/US2012/066987
§ 371 (c)(1),
(2) Date: Jan. 9, 2015

(87) PCT Pub. No.: WO2013/082243
PCT Pub. Date: Jun. 6, 2013

(65) Prior Publication Data
US 2014/0369972 A1  Dec. 18, 2014

Related U.S. Application Data

(60) Provisional application No. 61/566,492, filed on Dec. 2, 2011.

(51) Int. Cl.
| C12N 5/00 | (2006.01) |
|---|---|
| A01N 63/00 | (2006.01) |
| A61K 35/28 | (2015.01) |
| C12N 5/0789 | (2010.01) |
| A61K 35/12 | (2015.01) |
| A61K 35/51 | (2015.01) |

(52) U.S. Cl.
CPC ............ *A61K 35/28* (2013.01); *C12N 5/0647* (2013.01); *A61K 35/51* (2013.01); *A61K 2035/124* (2013.01); *C12N 2501/02* (2013.01); *C12N 2501/39* (2013.01)

(58) Field of Classification Search
None
See application file for complete search history.

(56) References Cited

U.S. PATENT DOCUMENTS

| 4,683,202 A | 7/1987 | Mullis |
|---|---|---|
| 5,077,049 A | 12/1991 | Dunn et al. |
| 5,397,706 A | 3/1995 | Correa et al. |
| 5,442,033 A | 8/1995 | Bezwada |
| 5,460,964 A | 10/1995 | McGlave et al. |
| 5,635,387 A | 6/1997 | Fei et al. |
| 5,677,136 A | 10/1997 | Simmons et al. |
| 5,716,827 A | 2/1998 | Tsukamoto et al. |
| 5,750,397 A | 5/1998 | Tsukamoto et al. |
| 5,753,516 A | 5/1998 | Heagy et al. |
| 5,759,793 A | 6/1998 | Schwartz et al. |
| 5,854,033 A | 12/1998 | Lizardi |
| 5,945,337 A | 8/1999 | Brown |
| 6,207,802 B1 | 3/2001 | Zsebo et al. |
| 6,610,719 B2 | 8/2003 | Paralkar et al. |
| 6,747,037 B1 | 6/2004 | Old et al. |
| 6,891,062 B2 | 5/2005 | Oida et al. |
| 7,131,958 B2 | 11/2006 | Deverre |
| 7,147,626 B2 | 12/2006 | Goodman et al. |
| 7,625,752 B2 | 12/2009 | Casper et al. |
| 8,551,782 B2 | 10/2013 | Zon et al. |
| 8,563,310 B2 | 10/2013 | Zon et al. |
| 2002/0115586 A1 | 8/2002 | Enikolopov et al. |
| 2003/0022363 A1 | 1/2003 | Rao et al. |
| 2005/0054103 A1 | 3/2005 | Peled et al. |
| 2005/0074435 A1 | 4/2005 | Casper et al. |
| 2005/0101599 A1 | 5/2005 | Zeiher et al. |
| 2006/0005153 A1 | 1/2006 | Maruyama et al. |
| 2006/0121085 A1 | 6/2006 | Warren et al. |
| 2006/0247214 A1 | 11/2006 | DeLong et al. |
| 2007/0154563 A1 | 7/2007 | Behnam et al. |
| 2009/0029912 A1 | 1/2009 | Gronthos et al. |
| 2009/0220465 A1 | 9/2009 | Scadden et al. |
| 2010/0143317 A1 | 6/2010 | Pecora et al. |
| 2010/0322907 A1 | 12/2010 | Calvi et al. |
| 2012/0189594 A1 | 7/2012 | Zon et al. |

(Continued)

FOREIGN PATENT DOCUMENTS

| EP | 1563846 A1 | 8/2005 |
|---|---|---|
| JP | 2009530408 A | 8/2009 |

(Continued)

OTHER PUBLICATIONS

Pittenger MF et al. 1999. Multilineage potential of adult human mesenchymal stem cells. Science 284: 143-147 (plus online supplemental content).*
Delorme B et al. 2008. Specific plasma membrane protein phenotype of culture-amplified and native human bone marrow mesenchymal stem cells. Blood 111: 2631-2635.*
Shyu A-B et al. 2008. Messenger RNA regulation: to translate or to degrade. EMBO J 27: 471-481.*
Adams et al., "Haematopoietic stem cells depend on Gαs-mediated signalling to engraft bone marrow," Nature, 459:103-107 (2009).
Attar et al., "Regulation of hematopoietic stem cell growth," Leukemia 18:1760-1768, 2004.
Barany, Genetic disease detection and DNA amplification using cloned thermostable ligase, Proc. Natl. Acad. Sci. USA, 88(1):189-193 (1991).

(Continued)

*Primary Examiner* — Lora E Barnhart Driscoll
(74) *Attorney, Agent, or Firm* — Jones Day

(57) ABSTRACT

The invention provides improved methods for cell therapy. In particular, the invention provides therapeutic compositions of enhanced hematopoietic stem and progenitor cells having improved engraftment and homing properties, and methods of making the therapeutic compositions. The invention further provides methods of improving the efficacy of hematopoietic stem and progenitor cell transplantation including transplanting the therapeutic composition to subjects in need of hematopoietic system reconstitution.

40 Claims, 14 Drawing Sheets

(56) References Cited

U.S. PATENT DOCUMENTS

| | | | |
|---|---|---|---|
| 2012/0202288 | A1 | 8/2012 | Mendlein et al. |
| 2013/0209423 | A1 | 8/2013 | Zon et al. |
| 2013/0209424 | A1 | 8/2013 | Zon et al. |
| 2013/0216507 | A1 | 8/2013 | Zon et al. |
| 2014/0369972 | A1 | 12/2014 | Shoemaker et al. |

FOREIGN PATENT DOCUMENTS

| | | | |
|---|---|---|---|
| RU | 2002113565 | A | 11/2000 |
| RU | 2205627 | C1 | 6/2003 |
| WO | 9506112 | A1 | 3/1995 |
| WO | 9640866 | A1 | 12/1996 |
| WO | 0038663 | A2 | 7/2000 |
| WO | 0050568 | A2 | 8/2000 |
| WO | 01/12596 | A1 | 2/2001 |
| WO | 2004032965 | A1 | 4/2004 |
| WO | 2004078169 | A1 | 9/2004 |
| WO | 2006047476 | A2 | 5/2006 |
| WO | 2006078886 | | 7/2006 |
| WO | 2006086639 | | 8/2006 |
| WO | 2007/071456 | A1 | 6/2007 |
| WO | 2007070964 | A1 | 6/2007 |
| WO | 2007112084 | A2 | 10/2007 |
| WO | 2008021475 | A2 | 2/2008 |
| WO | 2008056963 | A1 | 5/2008 |
| WO | 2008073748 | A1 | 6/2008 |
| WO | 2009104807 | A1 | 8/2009 |
| WO | 2009134532 | A2 | 11/2009 |
| WO | 2010054271 | A1 | 5/2010 |
| WO | 2010108028 | A2 | 9/2010 |
| WO | 2012021845 | A2 | 2/2012 |
| WO | 2013082241 | A2 | 6/2013 |
| WO | 2013082243 | A1 | 6/2013 |

OTHER PUBLICATIONS

Barker et al., "Mining the Wnt pathway for cancer therapeutics," Nature Reviews Drug Discovery 5:997-1014, 2006.
Brandt et al, "Practical aspects of preparative HPLC in pharmaceutical and development production," LC-GC Europe, pp. 2-5 (2002).
Bug et al., "Valproic Acid Stimulates Proliferation and Self-renewal of Hematopoietic stem cells," Cancer Research 65(7):2537-2541, 2005.
Capmany et al., "Short-term, serum-free, static culture of cord blood-derived CD34+ cells: effects of FLT3-L and MIP-1α on in vitro expansion of hematopoietic cells," Haematologica 84:675-682, 1999. Cayman Chemical Company, "16, 16-dimethyl Prostaglandin E2. Catalog No. 14750. CAS Registry No. 39746-25-3," Product Information, Mar. 30, 2006, one page.
Cayman Chemical Company, "16, 16-dimethyl Prostaglandin E2. Catalog No. 14750. CAS Registry No. 39746-25-3," Product Information, Mar. 30, 2006, one page.
Chen et al., "Intravenous administration of human umbilical cord blood reduces behavioral deficits after stroke in rats," Stroke, 32(11):2682-2688 (2001).
Cohn, S.M. et al., "Crypt stem cell surivival in the mouse intestinal epithelium is regulated by prostaglandins synthesized through cyclooxygenase-1," Journal of Clinical Investigation, 99(6):1367-1379, 1997.
Crawford, "Thoracoabdominal aortic aneurysms: Preoperative and intraoperative factors determining immediate and long-term results of operations in 605 patients," Vas. Surg. 3:389-404, 1986.
Curnow et al., "Topical Glucocorticoid Therapy Directly Induces Up-Regulation of Functional CXCR4 on Primed T Lymphocytes in the Aqueous Humor of Patients with Uveitis," The Journal of Immunology 172: 7154-7161, 2004.
Daley, J P, et al., "Ex vivo expansion of human hematopoietic progenitor cells in serum-free StemProTM-34 Medium," Focus 18(3):62-67, 2000.
Davidson and Zon, "The 'definitive' (and 'primitive') guide to zebrafish hematopoiesis," Oncogene 23:7233-7246, (2004).

De Jong and Zon, "Use of the zebrafish system to study primitive and definitive hematopoiesis," Annu. Rev. Genet. 39:481-501, (2005).
Desplat et al., "Is the COX-2 effect on accelerated hematopoiesis mediated by prostaglandin E2?" Experimental Hematology 28:741-742, (2000).
Dupuis et al., "Prostaglandin E2 Stimulates the Growth of Human Blood CD34+ Progenitors," Prostaglandins & Other Lipid Mediators 55:179-186, 1998.
FDA Guidance for Industry, Sterile drug products produced by aseptic processing—current good manufacturing practice, 63 pages (2003).
FDA Sterile drug products produced by aseptic processing draft, 50 pages, Sep. 22, 2002.
Feher and Gidali, "Prostaglandin E2 as stimulator of haemopoietic stem cell proliferation," Nature 247: 550-551, Feb. 22, 1974.
Freedman et al., "Autocrine and paracrine growth control by granulocyte-monocyte colony-stimulating factor of acute lymphoblastic leukemia cells," Blood, 81(11):3068-3075 (1993).
Galloway, J.L. et al., "Ontogeny of hematopoiesis: examining the emergence of hematopoietic cells in the vertebrate embryo," Curr Top Dev Biol. 53:139-158, 2003.
Gentile et al., "In Vivo Modulation of Murine Myelopoiesis Following Intravenous Administration of Prostaglandin E2," Blood 62(5):1100-1107, Nov. 1983.
Gidali and Feher, "The Effect of E Type Prostaglandins on the Proliferation of Haemopoietic Stem Cells In Vivo," Cell Tissue Kinet. 10: 365-373, 1977.
Goessling et al., "Genetic interaction of PGE2 and Wnt signaling regulates developmental specification of stem cells and regeneration," Cell 136:1136-1147, Mar. 20, 2009.
Goessling et al., "APC mutant zebrafish uncover a changing temporal requirement for Wnt signaling in liver development," Developmental Biology 320:161-174, 2008.
Goichberg et al., "cAMP-induced PKCzeta activation increases functional CXCR4 expression on human CD34+ hematopoietic progenitors," Blood. 107(3):870-879, 2006.
Guastalla et al., "Cyclooxygenase 2 and breast cancer," Bull. Cancer, 91(special):S99-108, 2004.
Guatelli et al., "Isothermal, in vitro amplification of nucleic acids by a multienzyme reaction modeled after retroviral replication," Proc. Natl. Acad. Sci USA, 87(5):1874-1878 (1990).
Hanson and Ainsworth, "16, 16-Dimethyl Prostaglandin E2 Induces Radioprotection in Murine Intestinal and Hematopoietic Stem Cells," Radiation Research 103: 196-203, 1985.
Hartshorn et al., "Cell Technology for Cell Products," pp. 221-224, R. Smith, Editor; Springer Netherlands, 2007.
Herrler et al., "Prostaglandin E positively modulates endothelial progenitor cell homeostasis: An advanced treatment modality for autologous cell therapy," Journal of Vascular Research 46: 333-346, Jan. 10 2009.
Hoggatt et al., "Prostaglandin E2 enhances hematopoietic stem cell homing, survival, and proliferation," Blood. 113(22):5444-5455, 2009.
Hoggart et al., "Eicosanoid regulation of hematopoiesis and hematopoietic stem and progenitor trafficking," Leukemia, 24(12):1993-2002 (2010).
Horowitz, "Uses and Growth of Hematopoietic Cell Transplantation," In: Blume KG, Forman SJ, Appelbaum FR, eds. Thomas' Hematopoietic Cell Transplantation. 3rd ed. Malden, Mass: Blackwell; 2007:9-15.
Hsia and Zon, "Transcriptional regulation of hematopoietic stem cell development in zebrafish," Experimental Hematology 33:1007-1014, 2005.
Hubbell et al., "Matrix Effects," Principles of Tissue Engineering, 2nd Ed, Academic Press, San Diego, CA pp. 237-250 (2000).
Jandl, Blood: Textbook of Hematology, 2nd Ed., Little, Brown and Company, Boston, MA pp. 544-545 (1996).
Janssens et al., "The Wnt-dependent signaling pathways as target in oncology drug discovery," Investigational New Drugs 24:263-280, 2006.

(56) References Cited

OTHER PUBLICATIONS

Kahn et al., "Overexpression of CXCR4 on human CD34+ progenitors increases their proliferation, migration, and NOD/SCID repopulation," Blood, 103(8):2942-2949 (2004).
Kamel et al., "Potential interaction of prostaglandin and Wnt signaling pathways mediating bone cell responses to fluid flow," Journal of Bone and Mineral Research, vol. 21, NR. Suppl. 1, p. S92, Sep. 15-19, 2006.
Kataoka et al., "Prostaglandin E2 receptor EP4 agonist induces Bcl-xL and independently activates proliferation signals in mouse primary hepatocytes," Journal of Gastroenterology 40(6): 610-616, Jun. 1, 2005.
Kishi. T. et al., "Bone marrow suppression induced by high dose valproic acid." Arch Dis Child 71(2):153-155, 1994.
Kollet et al., "Human CD34+CXCR4-sorted cells harbor intracellular CXCR4, which can be functionally expressed and provide NOD/SCID repopulation," Blood, 100(8):2778-2786 (2002).
Konturek et al., "Prostaglandins and ulcer healing," Journal of Physiology and Pharmacology 56 (Supp 5):5-31 2005.
Kouchoukos et al., "Elective hypothermic cardiopulmonary bypass and circulatory arrest for spinal cord protection during operations on the thoracoabdominal aorta," J. Thorac. Cardiovasc. Surg. 99:659-664,1990.
Krishnan et al., "Regulation of bone mass by Wnt signaling," J Clin Invest 116(5):1202-1209, May 2006.
Kurtzberg et al., "Unrelated Placental Blood in Marro Transplantation," Stem Cells 18:153-154, 2000.
Kwoh et al, "Transcription-based amplification system and detection of amplified human immunodeficiency virus type 1 with a bead-based sandwich hybridization format," Proc. Natl. Acad. Sci USA, 86(4)1173-1177 (1989).
Kyriakou et al., "Factors that influence short-term homing of human bone marrow-derived mesenchymal stem cells in a xenogeneic animal model," Haematologica—The Hematology Journal 93(10): 1457-1465, 2008.
Lee et al., "Mechanisms involved in prostaglandin E2-mediated neuroprotection against TNF-alpha: possible involvement of multiple signal transduction and beta-catenin/T-Cell factor," Journal of Neuroimmunology, 155(1-2):21-31, Oct. 1, 2004.
Liu et al., "Ex vivo expansion of hematopoietic stem cells derived from umbilical cord blood in rotating wall vessel," Journal of Biotechnology 124:592-601, 2006.
Lizardi et al., "Exponental amplification of recombinant-RNA hybridization probes," Bio/Technology 6:1197 (1988).
McCowage et al., "Multiparameter-fluorescence activated cell sorting analysis of retroviral vector gene transfer into primitive umbilical cord blood cells," Exp Hematol 26(4):288-298, Apr. 1998.
North and Zon, "Modeling human hematopoietic and cardiovascular diseases in zebrafish," Developmental Dynamics 228:568-583, 2003.
North et al., "Prostaglandin E2 regulates vertebrate haematopoietic stem cell homeostasis," Nature 447:1007-1011, Jun. 21, 2007.
Okamoto et al., "Molecular and clinical basis for the regeneration of human gastrointestinal epithelia," J. Gastroenterol, 39:1-6, 2004.
Okunieff et al., "Effects of hydralazine on in vivo tumor energy metabolism, hematopoietic radiation sensitivity, and cardiovascular parameters," International Journal of Radiation Oncology Biology Physics 16(5):1145-1148,1989.
Pachence et al., "Biodegradable polymers," Principles of Tissue Engineering, 2nd Ed, Academic Press, San Diego, CA pp. 263-278 (2000).
Paladin Labs Inc., "Summary basis of decision (SBD) PRVANTAS®, Histrelin acetate subdermal implant, 50mg," Submission Control No. 092567, 24 pages (2006).
Quackenbush, "Microarray data normalization and transformation," Nat. Genet., 32(Suppl):496-501 (2002).
SAFC Biosciences, Technical Bulletin, BIOEZE™ Bags—polyethylene (PE) film, 4 pages (2006).
Saltmann et al., "Cell interactions with polymers," Principles of Tissue Engineering, 2nd Ed, Academic Press, San Diego, CA pp. 221-236 (2000).
Sankaranarayanan et al., "Radioprotective Effects of Prostaglandins for Chromosomal Aberrations and Cell Killing in V79 Chinese Hamster Cells Grown as Spheroids in Vitro and for Mouse Spermatogonial Stem Cells and Bone Marrow Cells in Vivo," International Journal of Radiation Biology 67(1):47-55, 1995.
Schena et al., "Quantitative monitoring of gene expression patterns with a complementary DNA microarray," Science, 270(5235):467-470 (1995).
Schmidt et al., "Influence of prostaglandlin on repair of rat stomach damaged by absolute ethanol," Journal of Surgical Research 41(4): 367-377, Oct. 1, 1986.
Shao et al., "Prostaglandin E2 induces VEGF expression via the Wnt pathway," Gastroenterology, vol. 128, NR. 4, Suppl. 2, p. A146, Apr. 2005.
Shetsov et al., "Activation of beta-catenin signaling pathways by classical G-protein-coupled receptors: mechanisms and consequences in cycling and non-cycling cells," Cell Cycle 5(20): 2295-2300, Oct. 5, 2006. Epub Oct. 16, 2006.
Shi et al., "Regulation of CXCR4 expression in human mesenchymal stem cells by cytokine treatment: role in homing effeciency in NOD/SCID mice," Haematologica—The Hematology Journal 92(7): 897-904, Jul 2007.
Stier et al., "Notch1 activation increases hematopoietic stem cell self-renewal in vivo and favors lymphoid over myeloid lineage outcome," Blood, 99(7):2369-78, 2002.
Takayama et al., "Patterning of cells and their environment," Principles of Tissue Engineering, 2nd Ed, Academic Press, San Diego, CA pp. 209-218 (2000).
Thomson et al., "Polymer scaffold processing," Principles of Tissue Engineering, 2nd Ed, Academic Press, San Diego, CA pp. 251-262 (2000).
Tocris Bioscience, Safety Data Sheet. Product Name: Prostaglandin E2. Catalog No. 2296. CAS No. 363-24-6, Version 2.0 SDS Revision Date: Dec. 19, 2008, SDS Print Date Jan. 22, 2014, four pages.
Tseng Al-Sun et al., "The GSK-3 inhibitor 810 promotes proliferation in mammalian," Chemistry & Biology, 13:957-963, 2006.
Urakawa et al., "Study of 16, 16-dimethyl prostaglandin E2 for prevention of stress ulcer after hepatectomy of experimental cirrhotic liver and its influence on hepatic regeneration," Database EMBASE [online]1990.
Wagner et al., "Transplantation of unrelated donor umbilical cord blood in 102 patients with malignant and nonmalignant diseases: influence of CD34 cell dose and HLA disparity on treatment-related mortality and survival," Blood, 100(5):1611-1618 (2002).
Walden, TL Jr. et al., Abstract only. "16,16-Dimethyl prostaglandin E2 increases survival in mice following irradiation," Radial. Res. 109(3):440-448, Mar. 1987.
Weis et al., "Detection of rare mRNAs via quantitative RT-PCT," Trends Genet., 8(8):263-264 (1992).
WHO Pharmacopoeia Library, "Methods of analysis: 1. physical and physiochemical methods: 1.14 chromatography: 1.14.4 high-performance liquid chromattography," Retrieved from Internet. http://apps.who.int/phint/en/p/docf/, Aug. 15, 2003.

* cited by examiner

ENHANCED STEM CELL COMPOSITION

CROSS-REFERENCE TO RELATED APPLICATIONS

This application is a 371 of PCT/US2012/066987 filed Nov. 29, 2012, which application claims the benefit under 35 U.S.C. §119(e) of U.S. Provisional Application No. 61/566,492, filed Dec. 2, 2011, each of which is incorporated herein by reference in its entirety.

BACKGROUND

1. Technical Field

The invention relates to enhanced hematopoietic stem and progenitor cells and therapeutic compositions comprising the enhanced cells. The invention also relates to methods of making the enhanced hematopoietic and progenitor cells and therapeutic compositions and methods of use thereof, including use for reconstituting the hematopoietic system of an individual and treating conditions and diseases associated with ischemia.

2. Description of the Related Art

The goal of regenerative medicine is to maintain, improve or even restore the function of damaged or diseased cells, tissues, and organs. One way that regenerative medicine aims to revolutionize the practice of medicine is to employ cell-based therapeutics to treat patients. However, for the promise of cell-based therapeutics to be fully realized, the therapeutic cells should be well-tolerated when introduced into a patient, the cells should also migrate or "home" to sites where therapy is needed, and the cells should be capable of providing the therapy desired. The art has attempted to employ stem cell- and progenitor cell-based therapeutics but has met with little, if any, success in a human clinical setting.

One area of regenerative medicine that would benefit from improved cell-based therapeutics are stem cell transplants, e.g., bone marrow transplants and hematopoietic stem cell transplants to treat various genetic diseases, cancers, and degenerative disorders. According to the National Marrow Donor Program® (NMDP), an estimated 45,000 to 50,000 hematopoietic cell transplants are performed annually worldwide to treat patients with life-threatening malignant and non-malignant diseases. However, bone marrow transplantation has numerous drawbacks: bone marrow donation is painful, at times it is difficult and time consuming, and often not possible, to find HLA donor matched tissue; and allogeneic transplants are associated with a significant incidence of graft-versus-host-disease (GVHD). Moreover, although allogeneic hematopoietic stem cell transplants have been performed using more easily obtainable umbilical cord blood, cord blood transplants still have a risk of GVHD. Other drawbacks to existing methods of cord blood transplants, include fewer numbers of transplantable cells and deficient homing and engraftment of donor cells, both of which put the patient at high risk for life threatening infections. In addition, cord blood transplants generally have all the same risks as marrow and peripheral blood transplants.

Numerous approaches have been tried to expand the number of human hematopoietic stem and progenitor cells in cord blood within isolated grafts in ex vivo settings, to reduce the incidence of GVHD, or to increase the ability of the cells to home and engraft, but these efforts have had limited success.

Another area of regenerative medicine that would benefit from improved cell-based therapeutics is the treatment of tissue damaged by ischemia. Disruption of blood flow to tissues and organs is known as ischemia. The viability of cells, tissues, and organs in the human body depends on adequate blood flow. Adequate blood flow provides cells with oxygen, glucose, and much needed nutrients that are important for the regulation of cellular physiology and metabolism. Ischemia can be acute or chronic. Both acute and chronic forms of ischemia result in the loss of adequate nutrients to the cells, and if prolonged, will result in hypoxic and/or anoxic conditions. If the ischemia is left untreated, the cells may undergo necrosis or apoptosis, thereby jeopardizing the integrity and health of the tissue or organ.

Ischemia affects millions of patients in the United States each year. Ischemia is caused by a virtually limitless variety of genetic conditions, environmental insults, traumatic injury, or surgical interventions. The most common types of ischemia patients suffer from include, but are not limited to cerebral ischemias, spinal cord injuries, cardiovascular ischemias, limb ischemias, intestinal ischemias, dermal ischemias (e.g., burns and frostbite wounds) and ischemias resulting from medical and surgical procedures, including, but not limited to organ transplants, and skin grafts.

Currently, resolution of acute and chronic ischemia requires restoration of tissue perfusion and blood flow often using surgical means, which further places patients as risk for ischemic tissue damage. Restoration of blood flow after a period of ischemia can actually be more damaging than the ischemia. Reintroduction of oxygen causes a greater production of damaging free radicals as well as allowing, via removal of the extracellular acidotic conditions, influx of calcium and thus calcium overloading. Overall this results in reperfusion injury which can result in potentially fatal cardiac arrhythmias, also necrosis can be greatly accelerated. Other existing treatments that address ischemic tissue include hyperbaric oxygen, intravenous thrombolytics, anti-inflammatory agents, and local application of angiogenesis promoters. However, these treatments have generally met with limited success, if any.

Thus, many of the cell-based compositions and materials used in regenerative medicine are currently cost-prohibitive, inefficient, and/or unsafe. Other significant shortcomings for the use of stem cell- and progenitor cell-based therapeutic in regenerative medicine are the lack of technologies available to control stem cell proliferation, mobility, or to direct the stem cell, e.g., homing, to the particular niche or tissue where the therapy is needed. The end result is that cell-based therapeutics are not considered a realistic treatment option for those in need of regenerative medicine.

Accordingly, there is a substantial need in the art for improved cell-based therapeutics that are expandable, that are able to home to sites in the patient where therapy is desired, and that are able to provide a persistent therapeutic benefit. The present invention addresses these needs and offers other related advantages.

SUMMARY OF THE INVENTION

The invention generally provides novel cell-based compositions with improved therapeutic properties. In one embodiment, the present invention contemplates, in part, a human hematopoietic stem or progenitor cell comprising a hematopoietic stem or progenitor cell that has been contacted ex vivo with one or more agents that increase CXCR4 gene expression in the cells and gene expression of CXCR4 is increased at least about 30 fold in the contacted hematopoietic stem or progenitor cell compared to non-contacted hematopoietic stem or progenitor cells.

In a particular embodiment, the one or more agents comprises (i) one or more prostaglandin pathway agonists; and (ii) one or more glucocorticoids.

In a certain particular embodiment, the prostaglandin pathway agonist comprises a compound that selectively binds the $PGE_2$ $EP_2$ or $PGE_2$ $EP_4$ receptor.

In a further particular embodiment, the prostaglandin pathway agonist is selected from the group consisting of $PGE_2$, $dmPGE_2$, 15(S)-15-methyl $PGE_2$, 20-ethyl $PGE_2$, and 8-iso-16-cyclohexyl-tetranor $PGE_2$.

In another particular embodiment, the prostaglandin pathway agonist comprises $PGE_2$, or a $PGE_2$ analogue or derivative.

In an additional particular embodiment, the prostaglandin pathway agonist comprises 16,16-dimethyl $PGE_2$.

In a certain embodiment, the glucocorticoid is selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol.

In a further certain embodiment, the glucocorticoid is medrysone.

In an additional certain embodiment, the stem or progenitor cells have been contacted with at least one agent for a time of at least about one hour.

In another certain embodiment, the stem or progenitor cells have been contacted with at least one agent for a time of about one hour to about twenty-four hours.

In another certain embodiment, the stem or progenitor cells have been contacted with at least one agent for a time of about one hour to about twelve hours.

In another certain embodiment, the stem or progenitor cells have been contacted with at least one agent for a time of about one hour to about six hours.

In a particular certain embodiment, the stem or progenitor cells have been contacted with at least one agent for a time of about two hours to about six hours.

In a further embodiment, the stem or progenitor cells have been contacted with at least one agent for a time of about two hours to about four hours.

In an addition further embodiment, the cell is obtained from bone marrow, umbilical cord blood, mobilized peripheral blood, Wharton's jelly, placenta, or fetal blood.

In one embodiment, the present invention contemplates, in part, a composition, e.g., a therapeutic composition, comprising a population of cells comprising human hematopoietic stem or progenitor cells wherein the hematopoietic stem or progenitor cells have been contacted ex vivo with one or more agents that increase CXCR4 expression in the human hematopoietic stem or progenitor cells and gene expression of CXCR4 is increased at least about 30 fold in the contacted hematopoietic stem or progenitor cells compared to non-contacted hematopoietic stem or progenitor cells.

In an additional embodiment, the one or more agents comprises (i) one or more prostaglandin pathway agonists and (ii) one or more glucocorticoids.

In a particular additional embodiment, gene expression of CXCR4 is increased by at least about 40 fold in the contacted hematopoietic stem or progenitor cells compared to non-contacted hematopoietic stem or progenitor cells.

In a particular additional embodiment, gene expression of CXCR4 is increased by at least about 50 fold in the contacted hematopoietic stem or progenitor cells compared to non-contacted hematopoietic stem or progenitor cells.

In a particular additional embodiment, gene expression of CXCR4 is increased by at least about 60 fold in the contacted hematopoietic stem or progenitor cells compared to non-contacted hematopoietic stem or progenitor cells.

In a particular additional embodiment, gene expression of CXCR4 is increased by at least about 70 fold in the contacted hematopoietic stem or progenitor cells compared to non-contacted hematopoietic stem or progenitor cells.

In a particular additional embodiment, gene expression of CXCR4 is increased by at least about 80 fold in the contacted hematopoietic stem or progenitor cells compared to non-contacted hematopoietic stem or progenitor cells.

In a particular additional embodiment, gene expression of CXCR4 is increased by about 40 to about 80 fold in the contacted hematopoietic stem or progenitor cells compared to non-contacted hematopoietic stem or progenitor cells.

In a particular additional embodiment, gene expression of CXCR4 is increased by about 50 to about 80 fold in the contacted hematopoietic stem or progenitor cells compared to non-contacted hematopoietic stem or progenitor cells.

In a particular additional embodiment, gene expression of CXCR4 is increased by about 60 to about 80 fold in the contacted hematopoietic stem or progenitor cells compared to non-contacted hematopoietic stem or progenitor cells.

In certain additional embodiments, contacted hematopoietic stem or progenitor cells comprise a gene expression signature wherein gene expression of CXCR4 is increased by about 30, about 40, about 50, about 60, about 70, or about 80 fold in the contacted hematopoietic stem or progenitor cells compared to non-contacted hematopoietic stem or progenitor cells and wherein gene expression of one or more genes selected from the group consisting of: hyaluronan synthase 1 (HAS1), GTP-binding protein GEM (GEM), dual specificity protein phosphatase 4 (DUSP4), amphiregulin (AREG), Nuclear receptor related 1 protein (NR4A2), renin (REN), cAMP-responsive element modulator (CREM), collagen, type I, alpha 1 (COL1A1), and Fos-related antigen 2 (FOSL2) is increased by at least about two fold, about three fold, about four fold, about five fold, about ten fold, about twenty fold, about thirty fold, about forty fold, or about fifty fold in the treated stem or progenitor cells compared to non-contacted stem or progenitor cells.

In other additional embodiments, contacted hematopoietic stem or progenitor cells comprise a gene expression signature wherein gene expression of CXCR4 is increased by at least 30 fold in the contacted hematopoietic stem or progenitor cells compared to non-contacted cells and wherein gene expression of one or more genes selected from the group consisting of: HAS1, GEM, DUSP4, AREG, NR4A2, REN, CREM, COL1A1, FOSL2 is increased by at least about two fold in the treated stem or progenitor cells compared to non-contacted cells.

In other additional embodiments, contacted hematopoietic stem or progenitor cells comprise a gene expression signature wherein gene expression of CXCR4 is increased by at least 30 fold in the contacted hematopoietic stem or progenitor cells compared to non-contacted cells and wherein gene expression of one or more genes selected from the group consisting of: HAS1, GEM, DUSP4, AREG, NR4A2, REN, CREM, COL1A1, FOSL2 is increased by at least about three fold in the treated stem or progenitor cells compared to non-contacted cells.

In other additional embodiments, contacted hematopoietic stem or progenitor cells comprise a gene expression signature wherein gene expression of CXCR4 is increased by at least 30 fold in the contacted hematopoietic stem or progenitor cells compared to non-contacted cells and wherein gene expression of one or more genes selected from the group consisting of: HAS1, GEM, DUSP4, AREG, NR4A2, REN, CREM, COL1A1, FOSL2 is increased by at least about five fold in the treated stem or progenitor cells compared to non-contacted cells.

In other additional embodiments, contacted hematopoietic stem or progenitor cells comprise a gene expression signature wherein gene expression of CXCR4 is increased by at least 30 fold in the contacted hematopoietic stem or progenitor cells compared to non-contacted cells and wherein gene expression of one or more genes selected from the group consisting of: HAS1, GEM, DUSP4, AREG, NR4A2, REN, CREM, COL1A1, FOSL2 is increased by at least about ten fold in the treated stem or progenitor cells compared to non-contacted cells.

In other additional embodiments, contacted hematopoietic stem or progenitor cells comprise a gene expression signature wherein gene expression of CXCR4 is increased by at least 30 fold in the contacted hematopoietic stem or progenitor cells compared to non-contacted cells and wherein gene expression of two or more genes selected from the group consisting of: HAS1, GEM, DUSP4, AREG, NR4A2, REN, CREM, COL1A1, FOSL2 is increased by at least about two fold in the treated stem or progenitor cells compared to non-contacted cells.

In other additional embodiments, contacted hematopoietic stem or progenitor cells comprise a gene expression signature wherein gene expression of CXCR4 is increased by at least 30 fold in the contacted hematopoietic stem or progenitor cells compared to non-contacted cells and wherein gene expression of two or more genes selected from the group consisting of: HAS1, GEM, DUSP4, AREG, NR4A2, REN, CREM, COL1A1, FOSL2 is increased by at least about three fold in the treated stem or progenitor cells compared to non-contacted cells.

In other additional embodiments, contacted hematopoietic stem or progenitor cells comprise a gene expression signature wherein gene expression of CXCR4 is increased by at least 30 fold in the contacted hematopoietic stem or progenitor cells compared to non-contacted cells and wherein gene expression of two or more genes selected from the group consisting of: HAS1, GEM, DUSP4, AREG, NR4A2, REN, CREM, COL1A1, FOSL2 is increased by at least about five fold in the treated stem or progenitor cells compared to non-contacted cells.

In other additional embodiments, contacted hematopoietic stem or progenitor cells comprise a gene expression signature wherein gene expression of CXCR4 is increased by at least 30 fold in the contacted hematopoietic stem or progenitor cells compared to non-contacted cells and wherein gene expression of two or more genes selected from the group consisting of: HAS1, GEM, DUSP4, AREG, NR4A2, REN, CREM, COL1A1, FOSL2 is increased by at least about ten fold in the treated stem or progenitor cells compared to non-contacted cells.

In other additional embodiments, contacted hematopoietic stem or progenitor cells comprise a gene expression signature wherein gene expression of CXCR4 is increased by at least 30 fold in the contacted hematopoietic stem or progenitor cells compared to non-contacted cells and wherein gene expression of three or more genes selected from the group consisting of: HAS1, GEM, DUSP4, AREG, NR4A2, REN, CREM, COL1A1, FOSL2 is increased by at least about two fold in the treated stem or progenitor cells compared to non-contacted cells.

In other additional embodiments, contacted hematopoietic stem or progenitor cells comprise a gene expression signature wherein gene expression of CXCR4 is increased by at least 30 fold in the contacted hematopoietic stem or progenitor cells compared to non-contacted cells and wherein gene expression of three or more genes selected from the group consisting of: HAS1, GEM, DUSP4, AREG, NR4A2, REN, CREM, COL1A1, FOSL2 is increased by at least about three fold in the treated stem or progenitor cells compared to non-contacted cells.

In other additional embodiments, contacted hematopoietic stem or progenitor cells comprise a gene expression signature wherein gene expression of CXCR4 is increased by at least 30 fold in the contacted hematopoietic stem or progenitor cells compared to non-contacted cells and wherein gene expression of three or more genes selected from the group consisting of: HAS1, GEM, DUSP4, AREG, NR4A2, REN, CREM, COL1A1, FOSL2 is increased by at least about five fold in the treated stem or progenitor cells compared to non-contacted cells.

In other additional embodiments, contacted hematopoietic stem or progenitor cells comprise a gene expression signature wherein gene expression of CXCR4 is increased by at least 30 fold in the contacted hematopoietic stem or progenitor cells compared to non-contacted cells and wherein gene expression of three or more genes selected from the group consisting of: HAS1, GEM, DUSP4, AREG, NR4A2, REN, CREM, COL1A1, FOSL2 is increased by at least about ten fold in the treated stem or progenitor cells compared to non-contacted cells.

In a certain additional embodiment, the prostaglandin pathway agonist comprises a compound that selectively binds the $PGE_2$ $EP_2$ or $PGE_2$ $EP_4$ receptor.

In a further additional embodiment, the prostaglandin pathway agonist is selected from the group consisting of $PGE_2$, $dmPGE_2$, 15(S)-15-methyl $PGE_2$, 20-ethyl $PGE_2$, and 8-iso-16-cyclohexyl-tetranor $PGE_2$.

In another additional embodiment, the prostaglandin pathway agonist comprises $PGE_2$, or a $PGE_2$ analogue or derivative thereof.

In another embodiment, the prostaglandin pathway agonist comprises 16,16-dimethyl $PGE_2$.

In another particular embodiment, the glucocorticoid is selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol.

In another certain embodiment, the hematopoietic stem or progenitor cells have been contacted for a time of at least about one hour with at least one of (i) one or more prostaglandin pathway agonists or (ii) one or more glucocorticoids.

In another further embodiment, the hematopoietic stem or progenitor cells have been contacted for a time of about two hours to about twenty-four hours with at least one of (i) one or more prostaglandin pathway agonists and (ii) one or more glucocorticoids.

In another additional embodiment, the hematopoietic stem or progenitor cells have been contacted for a time of about two hours to about six hours with at least one of (i) one or more prostaglandin pathway agonists and (ii) one or more glucocorticoids.

In a particular embodiment, the hematopoietic stem or progenitor cells have been contacted for a time of about four hours with at least one of (i) one or more prostaglandin pathway agonists and (ii) one or more glucocorticoids.

In a certain embodiment, the population of cells comprises less than about 0.10, 0.50, 1.0, 3, 5, 10, 15, 20, or 30% $CD34^+$ cells.

In a further embodiment, the population of cells comprises at least about 0.01% and no more than about 50% of $CD34^+$ cells.

In another embodiment, the population of cells comprises at least about 1% $CD34^+$ cells.

In an additional embodiment, the population of cells comprises at least about 3% $CD34^+$ cells.

In a particular embodiment, the population of cells comprises at least about 5% $CD34^+$ cells.

In another particular embodiment, the population of cells comprises at least about 10% $CD34^+$ cells.

In yet another particular embodiment, the population of cells comprises at least about 20% $CD34^+$ cells.

In still yet another particular embodiment, the population of cells comprises at least about 30% $CD34^+$ cells.

In a certain embodiment, the population of cells comprises at least about 40% $CD34^+$ cells.

In another certain embodiment, the population of cells comprises at least about 50% $CD34^+$ cells.

In yet another certain embodiment, the population of cells comprises at least about 60% $CD34^+$ cells.

In still yet another certain embodiment, the population of cells comprises at least about 70% $CD34^+$ cells.

In a further embodiment, the population of cells comprises at least about 80% $CD34^+$ cells.

In another further embodiment, the population of cells comprises at least about 90% $CD34^+$ cells.

In yet another further embodiment, the population of cells comprises at least about 95% $CD34^+$ cells.

In an additional embodiment, the population of cells is not expanded ex vivo.

In a certain embodiment, the composition is generated at a point-of-care and is administered into a patient without culturing the population of cells.

In a further embodiment, the composition is washed and is substantially free of the one or more agents.

In another embodiment, the population of cells is obtained from bone marrow, fetal liver, fetal blood, placenta, placental blood, umbilical cord blood, or mobilized peripheral blood.

In one embodiment, the present invention contemplates, in part, a method of preparing a human hematopoietic stem or progenitor cell comprising contacting the hematopoietic stem or progenitor cell ex vivo with one or more agents that increase CXCR4 gene expression in the cells; wherein the CXCR4 gene expression is increased at least about 30 fold in the contacted hematopoietic stem or progenitor cell compared to non-contacted hematopoietic stem or progenitor cells.

In a particular embodiment, the one or more agents comprises (i) one or more prostaglandin pathway agonists; and (ii) one or more glucocorticoids.

In a certain particular embodiment, the prostaglandin pathway agonist comprises a compound that selectively binds the $PGE_2$ $EP_2$ or $PGE_2$ $EP_4$ receptor.

In a further particular embodiment, the prostaglandin pathway agonist is selected from the group consisting of $PGE_2$, $dmPGE_2$, 15(S)-15-methyl $PGE_2$, 20-ethyl $PGE_2$, and 8-iso-16-cyclohexyl-tetranor $PGE_2$.

In another particular embodiment, the prostaglandin pathway agonist comprises $PGE_2$, or a $PGE_2$ analogue or derivative.

In an additional particular embodiment, the prostaglandin pathway agonist comprises 16,16-dimethyl $PGE_2$.

In a certain embodiment, the glucocorticoid is selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol.

In a further certain embodiment, the glucocorticoid is medrysone.

In an additional certain embodiment, the stem or progenitor cells have been contacted with at least one agent for a time of at least about one hour.

In another certain embodiment, the hematopoietic stem or progenitor cell has been contacted with at least one agent for a time of about one hour to about twenty-four hours.

In another certain embodiment, the stem or progenitor cells have been contacted with at least one agent for a time of about one hour to about six hours.

In a particular certain embodiment, the stem or progenitor cells have been contacted with at least one agent for a time of about two hours to about six hours.

In a further embodiment, the stem or progenitor cells have been contacted with at least one agent for a time of about two hours to about four hours.

In an addition further embodiment, the cell is obtained from bone marrow, umbilical cord blood, mobilized peripheral blood, Wharton's jelly, placenta, or fetal blood.

In one embodiment, the present invention contemplates, in part, a method of preparing a therapeutic composition comprising contacting hematopoietic stem or progenitor cells ex vivo with (i) one or more prostaglandin pathway agonists and (ii) one or more glucocorticoids; wherein the CXCR4 gene expression is increased at least about 30 fold in the contacted hematopoietic stem or progenitor cells compared to non-contacted hematopoietic stem or progenitor cells.

In a particular embodiment, gene expression of CXCR4 is increased by at least about 40 fold in the contacted hematopoietic stem or progenitor cells compared to non-contacted hematopoietic stem or progenitor cells.

In a certain particular embodiment, the prostaglandin pathway agonist comprises a compound that selectively binds the $PGE_2$ $EP_2$ or $PGE_2$ $EP_4$ receptor.

In a further particular embodiment, the prostaglandin pathway agonist is selected from the group consisting of $PGE_2$, $dmPGE_2$, 15(S)-15-methyl $PGE_2$, 20-ethyl $PGE_2$, and 8-iso-16-cyclohexyl-tetranor $PGE_2$.

In another particular embodiment, the prostaglandin pathway agonist comprises $PGE_2$, or a $PGE_2$ analogue or derivative.

In an additional particular embodiment, the prostaglandin pathway agonist comprises 16,16-dimethyl $PGE_2$.

In a certain embodiment, the glucocorticoid is selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol.

In a further certain embodiment, the glucocorticoid is medrysone.

In a particular embodiment, the hematopoietic stem or progenitor cells have been contacted with (i) one or more prostaglandin pathway agonists and (ii) one or more glucocorticoids for a time of at least about one hour.

In a further particular embodiment, the hematopoietic stem or progenitor cells have been contacted with (i) one or more prostaglandin pathway agonists and (ii) one or more glucocorticoids for a time of about two hours to about twenty-four hours.

In a further particular embodiment, the hematopoietic stem or progenitor cells have been contacted with (i) one or more prostaglandin pathway agonists and (ii) one or more glucocorticoids for a time of about two hours to about twelve hours.

In a further particular embodiment, the hematopoietic stem or progenitor cells have been contacted with (i) one or more prostaglandin pathway agonists and (ii) one or more glucocorticoids for a time of about two hours to about six hours.

In an additional particular embodiment, the hematopoietic stem or progenitor cells have been contacted with (i) one or more prostaglandin pathway agonists and (ii) one or more glucocorticoids for a time of about two hours to about four hours.

In another particular embodiment, the hematopoietic stem or progenitor cells have been contacted with (i) one or more prostaglandin pathway agonists and (ii) one or more glucocorticoids for a time of about four hours.

In a certain embodiment, the population of cells comprises less than about 0.10, 0.50, 1.0, 3, 5, 10, 15, 20, or 30% $CD34^+$ cells.

In a further embodiment, the population of cells comprises at least about 0.01% and no more than about 50% of $CD34^+$ cells.

In another embodiment, the population of cells comprises at least about 1% $CD34^+$ cells.

In an additional embodiment, the population of cells comprises at least about 3% $CD34^+$ cells.

In a particular embodiment, the population of cells comprises at least about 5% $CD34^+$ cells.

In another particular embodiment, the population of cells comprises at least about 10% $CD34^+$ cells.

In yet another particular embodiment, the population of cells comprises at least about 20% $CD34^+$ cells.

In still yet another particular embodiment, the population of cells comprises at least about 30% $CD34^+$ cells.

In a certain embodiment, the population of cells comprises at least about 40% $CD34^+$ cells.

In another certain embodiment, the population of cells comprises at least about 50% $CD34^+$ cells.

In yet another certain embodiment, the population of cells comprises at least about 60% $CD34^+$ cells.

In still yet another certain embodiment, the population of cells comprises at least about 70% $CD34^+$ cells.

In a further embodiment, the population of cells comprises at least about 80% $CD34^+$ cells.

In another further embodiment, the population of cells comprises at least about 90% $CD34^+$ cells.

In yet another further embodiment, the population of cells comprises at least about 95% CD34+ cells.

In an additional embodiment, the population of cells is not expanded ex vivo.

In a certain embodiment, the composition is generated at a point-of-care and is administered into a patient without culturing the population of cells.

In a further embodiment, the composition is washed and is substantially free of the one or more agents.

In another embodiment, the population of cells is obtained from bone marrow, fetal liver, fetal blood, placenta, placental blood, umbilical cord blood, or mobilized peripheral blood.

In various embodiments, the present invention contemplates, in part, a method of treating a subject in need of cell therapy comprising administering to the subject human hematopoietic stem or progenitor cells wherein the hematopoietic stem or progenitor cells have been contacted ex vivo one or more agents that increase CXCR4 expression in the human hematopoietic stem or progenitor cells and gene expression of CXCR4 is increased at least about 30 fold in the contacted hematopoietic stem or progenitor cells compared to non-contacted hematopoietic stem or progenitor cells.

In a particular embodiment, the subject has acute myelogenous leukemia (AML), acute lymphoblastic leukemia (ALL), chronic myelogenous leukemia (CML), chronic lymphocytic leukemia (CLL), juvenile myelomonocytic leukemia, Hodgkin's lymphoma, non-Hodgkin's lymphoma, multiple myeloma, severe aplastic anemia, Fanconi's anemia, paroxysmal nocturnal hemoglobinuria (PNH), pure red cell aplasia, amegakaryocytosis/congenital thrombocytopenia, severe combined immunodeficiency syndrome (SCID), Wiskott-Aldrich syndrome, beta-thalassemia major, sickle cell disease, Hurler's syndrome, adrenoleukodystrophy, metachromatic leukodystrophy, myelodysplasia, refractory anemia, chronic myelomonocytic leukemia, agnogenic myeloid metaplasia, familial erythrophagocytic lymphohistiocytosis, solid tumors, chronic granulomatous disease, mucopolysaccharidoses, or Diamond Blackfan.

In a certain embodiment, the subject has breast cancer, ovarian cancer, brain cancer, prostate cancer, lung cancer, colon cancer, skin cancer, liver cancer, pancreatic cancer, or sarcoma.

In another embodiment, the subject has received bone marrow ablative or non-myeolablative chemotherapy or radiation therapy.

In a further embodiment, the subject is a bone marrow donor.

In one embodiment, the subject has an ischemic tissue or a tissue damaged by ischemia.

In a particular embodiment, the subject has at least one symptom associated with an ischemic tissue or a tissue damaged by ischemia.

In various embodiments, the ischemia is associated with acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

In one embodiment, the present invention contemplates, in part, a method of increasing hematopoietic stem and progenitor cell homing and/or engraftment in a subject comprising administering to the subject a composition comprising a population of cells comprising human hematopoietic stem or progenitor cells wherein the hematopoietic stem or progenitor cells have been contacted ex vivo with one or more agents that increase CXCR4 gene expression in the cells; and gene expression of CXCR4 is increased at least about 30 fold in the contacted hematopoietic stem or progenitor cells compared to non-contacted hematopoietic stem or progenitor cells.

In a particular embodiment, the one or more agents comprises (i) one or more prostaglandin pathway agonists; and (ii) one or more glucocorticoids.

In a certain particular embodiment, the prostaglandin pathway agonist comprises a compound that selectively binds the $PGE_2$ $EP_2$ or $PGE_2$ $EP_4$ receptor.

In a further particular embodiment, the prostaglandin pathway agonist is selected from the group consisting of $PGE_2$, $dmPGE_2$, 15(S)-15-methyl $PGE_2$, 20-ethyl $PGE_2$, and 8-iso-16-cyclohexyl-tetranor $PGE_2$.

In another particular embodiment, the prostaglandin pathway agonist comprises $PGE_2$, or a $PGE_2$ analogue or derivative.

In an additional particular embodiment, the prostaglandin pathway agonist comprises 16,16-dimethyl $PGE_2$.

In a certain embodiment, the glucocorticoid is selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol.

In a further certain embodiment, the glucocorticoid is medrysone.

In an additional certain embodiment, the stem or progenitor cells have been contacted with at least one agent for a time of at least about one hour.

In another certain embodiment, the hematopoietic stem or progenitor cell has been contacted with at least one agent for a time of about one hour to about twenty-four hours.

In another certain embodiment, the stem or progenitor cells have been contacted with at least one agent for a time of about one hour to about six hours.

In a particular certain embodiment, the stem or progenitor cells have been contacted with at least one agent for a time of about two hours to about six hours.

In a further embodiment, the stem or progenitor cells have been contacted with at least one agent for a time of about two hours to about four hours.

In an addition further embodiment, the cell is obtained from bone marrow, umbilical cord blood, mobilized peripheral blood, Wharton's jelly, placenta, or fetal blood.

In one embodiment, the present invention contemplates, a method of increasing hematopoietic stem and progenitor cell homing and/or engraftment in a subject comprising administering to the subject a composition comprising a population of cells comprising human hematopoietic stem or progenitor cells wherein the hematopoietic stem or progenitor cells have been contacted ex vivo with (i) one or more prostaglandin pathway agonists and (ii) one or more glucocorticoids; and gene expression of CXCR4 is increased at least about 30 fold in the contacted hematopoietic stem or progenitor cells compared to non-contacted hematopoietic stem or progenitor cells.

In a particular embodiment, gene expression of CXCR4 is increased by at least about 40 fold in the contacted hematopoietic stem or progenitor cells compared to non-contacted hematopoietic stem or progenitor cells.

In a certain particular embodiment, the prostaglandin pathway agonist comprises a compound that selectively binds the $PGE_2$ $EP_2$ or $PGE_2$ $EP_4$ receptor.

In a further particular embodiment, the prostaglandin pathway agonist is selected from the group consisting of $PGE_2$, $dmPGE_2$, 15(S)-15-methyl $PGE_2$, 20-ethyl $PGE_2$, and 8-iso-16-cyclohexyl-tetranor $PGE_2$.

In another particular embodiment, the prostaglandin pathway agonist comprises $PGE_2$, or a $PGE_2$ analogue or derivative.

In an additional particular embodiment, the prostaglandin pathway agonist comprises 16,16-dimethyl $PGE_2$.

In a certain embodiment, the glucocorticoid is selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol.

In a further certain embodiment, the glucocorticoid is medrysone.

In a particular embodiment, the hematopoietic stem or progenitor cells have been contacted with (i) one or more prostaglandin pathway agonists and (ii) one or more glucocorticoids for a time of at least about one hour.

In a further particular embodiment, the hematopoietic stem or progenitor cells have been contacted with (i) one or more prostaglandin pathway agonists and (ii) one or more glucocorticoids for a time of about two hours to about six hours.

In an additional particular embodiment, the hematopoietic stem or progenitor cells have been contacted with (i) one or more prostaglandin pathway agonists and (ii) one or more glucocorticoids for a time of about two hours to about four hours.

In another particular embodiment, the hematopoietic stem or progenitor cells have been contacted with (i) one or more prostaglandin pathway agonists and (ii) one or more glucocorticoids for a time of about four hours.

In a certain embodiment, the population of cells comprises less than about 0.10, 0.50, 1.0, 3, 5, 10, 15, 20, or 30% $CD34^+$ cells.

In a further embodiment, the population of cells comprises at least about 0.01% and no more than about 50% of $CD34^+$ cells.

In another embodiment, the population of cells comprises at least about 1% $CD34^+$ cells.

In an additional embodiment, the population of cells comprises at least about 3% $CD34^+$ cells.

In a particular embodiment, the population of cells comprises at least about 5% $CD34^+$ cells.

In another particular embodiment, the population of cells comprises at least about 10% $CD34^+$ cells.

In yet another particular embodiment, the population of cells comprises at least about 20% $CD34^+$ cells.

In still yet another particular embodiment, the population of cells comprises at least about 30% $CD34^+$ cells.

In a certain embodiment, the population of cells comprises at least about 40% $CD34^+$ cells.

In another certain embodiment, the population of cells comprises at least about 50% $CD34^+$ cells.

In yet another certain embodiment, the population of cells comprises at least about 60% $CD34^+$ cells.

In still yet another certain embodiment, the population of cells comprises at least about 70% CD34+ cells.

In a further embodiment, the population of cells comprises at least about 80% CD34+ cells.

In another further embodiment, the population of cells comprises at least about 90% CD34+ cells.

In yet another further embodiment, the population of cells comprises at least about 95% CD34+ cells.

In an additional embodiment, the population of cells is not expanded ex vivo.

In a certain embodiment, the composition is generated at a point-of-care and is administered into a patient without culturing the population of cells.

In a further embodiment, the composition is washed and is substantially free of the one or more agents.

In another embodiment, the population of cells is obtained from bone marrow, fetal liver, fetal blood, placenta, placental blood, umbilical cord blood, or mobilized peripheral blood.

In various preceding embodiments, the subject has acute myelogenous leukemia (AML), acute lymphoblastic leukemia (ALL), chronic myelogenous leukemia (CML), chronic lymphocytic leukemia (CLL), juvenile myelomonocytic leukemia, Hodgkin's lymphoma, non-Hodgkin's lymphoma, multiple myeloma, severe aplastic anemia, Fanconi's anemia, paroxysmal nocturnal hemoglobinuria (PNH), pure red cell aplasia, amegakaryocytosis/congenital thrombocytopenia, severe combined immunodeficiency syndrome (SCID), Wiskott-Aldrich syndrome, beta-thalassemia major, sickle cell disease, Hurler's syndrome, adrenoleukodystrophy, metachromatic leukodystrophy, myelodysplasia, refractory anemia, chronic myelomonocytic leukemia, agnogenic myeloid metaplasia, familial erythrophagocytic lymphohistiocytosis, or solid tumors.

In several preceding embodiments, the subject has breast cancer, ovarian cancer, brain cancer, prostate cancer, lung cancer, colon cancer, skin cancer, liver cancer, pancreatic cancer, or sarcoma.

In any of the preceding embodiments, the subject has received bone marrow ablative or non-myeolablative chemotherapy or radiation therapy.

In particular preceding embodiments, the subject is a bone marrow donor.

In certain preceding embodiments, the population of cells is autogeneic to the subject.

In several preceding embodiments, the population of cells is mobilized from the peripheral blood or bone marrow of the subject.

In various preceding embodiments, the population of cells is allogeneic to the subject.

In one embodiment, the present invention contemplates, in part, a method of increasing hematopoietic stem and progenitor cell reconstitution in a subject comprising administering to the subject a composition comprising a population of cells comprising human hematopoietic stem or progenitor cells wherein the hematopoietic stem or progenitor cell has been contacted ex vivo with one or more agents that increase CXCR4 gene expression in the cells; and gene expression of CXCR4 is increased at least about 30 fold in the contacted hematopoietic stem or progenitor cell compared to non-contacted hematopoietic stem or progenitor cells.

In a particular embodiment, the one or more agents comprises (i) one or more prostaglandin pathway agonists; and (ii) one or more glucocorticoids.

In a certain particular embodiment, the prostaglandin pathway agonist comprises a compound that selectively binds the $PGE_2$ $EP_2$ or $PGE_2$ $EP_4$ receptor.

In a further particular embodiment, the prostaglandin pathway agonist is selected from the group consisting of $PGE_2$, $dmPGE_2$, 15(S)-15-methyl $PGE_2$, 20-ethyl $PGE_2$, and 8-iso-16-cyclohexyl-tetranor $PGE_2$.

In another particular embodiment, the prostaglandin pathway agonist comprises $PGE_2$, or a $PGE_2$ analogue or derivative.

In an additional particular embodiment, the prostaglandin pathway agonist comprises 16,16-dimethyl $PGE_2$.

In a certain embodiment, the glucocorticoid is selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol.

In a further certain embodiment, the glucocorticoid is medrysone.

In an additional certain embodiment, the stem or progenitor cells have been contacted with at least one agent for a time of at least about one hour.

In another certain embodiment, the hematopoietic stem or progenitor cell has been contacted with at least one agent for a time of about one hour to about twenty-four hours.

In another certain embodiment, the stem or progenitor cells have been contacted with at least one agent for a time of about one hour to about six hours.

In a particular certain embodiment, the stem or progenitor cells have been contacted with at least one agent for a time of about two hours to about six hours.

In a further embodiment, the stem or progenitor cells have been contacted with at least one agent for a time of about two hours to about four hours.

In an addition further embodiment, the cell is obtained from bone marrow, umbilical cord blood, mobilized peripheral blood, Wharton's jelly, placenta, or fetal blood.

In one embodiment, the present invention contemplates, in part, a method of increasing hematopoietic stem and progenitor cell reconstitution in a subject comprising administering to the subject a composition comprising a population of cells comprising human hematopoietic stem or progenitor cells wherein the hematopoietic stem or progenitor cells have been contacted ex vivo with (i) one or more prostaglandin pathway agonists and (ii) one or more glucocorticoids; and b) gene expression of CXCR4 is increased at least about 30 fold in the contacted hematopoietic stem or progenitor cells compared to non-contacted hematopoietic stem or progenitor cells.

In a particular embodiment, gene expression of CXCR4 is increased by at least about 40 fold in the contacted hematopoietic stem or progenitor cells compared to non-contacted hematopoietic stem or progenitor cells.

In a certain particular embodiment, the prostaglandin pathway agonist comprises a compound that selectively binds the $PGE_2$ $EP_2$ or $PGE_2$ $EP_4$ receptor.

In a further particular embodiment, the prostaglandin pathway agonist is selected from the group consisting of $PGE_2$, $dmPGE_2$, 15(S)-15-methyl $PGE_2$, 20-ethyl $PGE_2$, and 8-iso-16-cyclohexyl-tetranor $PGE_2$.

In another particular embodiment, the prostaglandin pathway agonist comprises $PGE_2$, or a $PGE_2$ analogue or derivative.

In an additional particular embodiment, the prostaglandin pathway agonist comprises 16,16-dimethyl $PGE_2$.

In a certain embodiment, the glucocorticoid is selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol.

In a further certain embodiment, the glucocorticoid is medrysone.

In a particular embodiment, the hematopoietic stem or progenitor cells have been contacted with (i) one or more prostaglandin pathway agonists and (ii) one or more glucocorticoids for a time of at least about one hour.

In a further particular embodiment, the hematopoietic stem or progenitor cells have been contacted with (i) one or more prostaglandin pathway agonists and (ii) one or more glucocorticoids for a time of about two hours to about six hours.

In an additional particular embodiment, the hematopoietic stem or progenitor cells have been contacted with (i) one or more prostaglandin pathway agonists and (ii) one or more glucocorticoids for a time of about two hours to about four hours.

In another particular embodiment, the hematopoietic stem or progenitor cells have been contacted with (i) one or more prostaglandin pathway agonists and (ii) one or more glucocorticoids for a time of about four hours.

In a certain embodiment, the population of cells comprises less than about 0.10, 0.50, 1.0, 3, 5, 10, 15, 20, or 30% $CD34^+$ cells.

In a further embodiment, the population of cells comprises at least about 0.01% and no more than about 50% of $CD34^+$ cells.

In another embodiment, the population of cells comprises at least about 1% $CD34^+$ cells.

In an additional embodiment, the population of cells comprises at least about 3% $CD34^+$ cells.

In a particular embodiment, the population of cells comprises at least about 5% $CD34^+$ cells.

In another particular embodiment, the population of cells comprises at least about 10% $CD34^+$ cells.

In yet another particular embodiment, the population of cells comprises at least about 20% $CD34^+$ cells.

In still yet another particular embodiment, the population of cells comprises at least about 30% $CD34^+$ cells.

In a certain embodiment, the population of cells comprises at least about 40% $CD34^+$ cells.

In another certain embodiment, the population of cells comprises at least about 50% $CD34^+$ cells.

In yet another certain embodiment, the population of cells comprises at least about 60% $CD34^+$ cells.

In still yet another certain embodiment, the population of cells comprises at least about 70% $CD34^+$ cells.

In a further embodiment, the population of cells comprises at least about 80% $CD34^+$ cells.

In another further embodiment, the population of cells comprises at least about 90% $CD34^+$ cells.

In yet another further embodiment, the population of cells comprises at least about 95% $CD34^+$ cells.

In an additional embodiment, the population of cells is not expanded ex vivo.

In a certain embodiment, the composition is generated at a point-of-care and is administered into a patient without culturing the population of cells.

In a further embodiment, the composition is washed and is substantially free of the one or more agents.

In another embodiment, the population of cells is obtained from bone marrow, fetal liver, fetal blood, placenta, placental blood, umbilical cord blood, or mobilized peripheral blood.

In various embodiments, the population of cells comprises one or more cord blood units.

In various preceding embodiments, the subject has acute myelogenous leukemia (AML), acute lymphoblastic leukemia (ALL), chronic myelogenous leukemia (CML), chronic lymphocytic leukemia (CLL), juvenile myelomonocytic leukemia, Hodgkin's lymphoma, non-Hodgkin's lymphoma, multiple myeloma, severe aplastic anemia, Fanconi's anemia, paroxysmal nocturnal hemoglobinuria (PNH), pure red cell aplasia, amegakaryocytosis/congenital thrombocytopenia, severe combined immunodeficiency syndrome (SCID), Wiskott-Aldrich syndrome, beta-thalassemia major, sickle cell disease, Hurler's syndrome, adrenoleukodystrophy, metachromatic leukodystrophy, myelodysplasia, refractory anemia, chronic myelomonocytic leukemia, agnogenic myeloid metaplasia, familial erythrophagocytic lymphohistiocytosis, or solid tumors.

In several preceding embodiments, the subject has breast cancer, ovarian cancer, brain cancer, prostate cancer, lung cancer, colon cancer, skin cancer, liver cancer, pancreatic cancer, or sarcoma.

In any of the preceding embodiments, the subject has received bone marrow ablative or non-myeolablative chemotherapy or radiation therapy.

In particular preceding embodiments, the subject is a bone marrow donor.

In certain preceding embodiments, the population of cells is autogeneic to the subject.

In several preceding embodiments, the population of cells is mobilized from the peripheral blood or bone marrow of the subject.

In various preceding embodiments, the population of cells is allogeneic to the subject.

DETAILED DESCRIPTION

A. Overview

Figure 1:
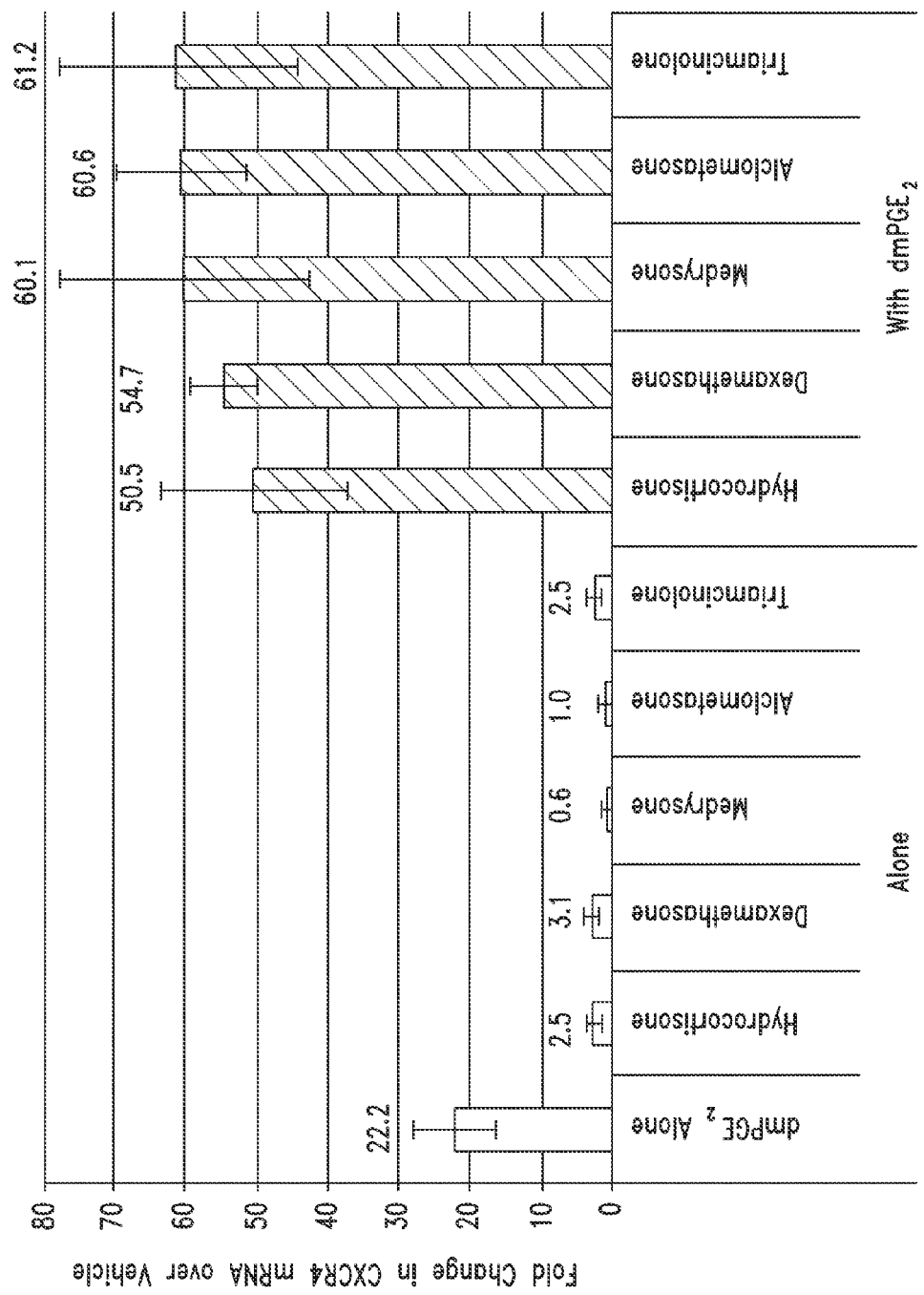
FIG. 1 shows the increase in levels of CXCR4 mRNA detected (relative to vehicle treatment) in human cord blood CD34+ cells when the cells are treated with either 10 μM of a single agent or with a combination of 10 μM dmPGE$_2$ and 10 μM of one of five different glucocorticoids. Glucocorticoids act synergistically with dmPGE$_2$ to increase CXCR4 gene expression.

The invention provides human hematopoietic stem and progenitor cells that are treated ex vivo to enhance the therapeutic properties of the cells. In particular, the hematopoietic stem and progenitor cells of the invention have been modified ex vivo by briefly treating the cells with one or more agents that increase gene expression of genes involved in homing. In one embodiment, hematopoietic stem and progenitor cells of the invention have been modified ex vivo by briefly treating the cells with one or more agents that increase CXCR4 expression. The therapeutic cells of the invention express unexpectedly high levels of CXCR4 compared to untreated human hematopoietic stem and progenitor cells. In particular embodiments, the pharmacologically enhanced cells of the invention are characterized by an increase in gene expression of CXCR4 of at least about 30 fold compared to untreated cells. In various embodiments, the therapeutic cells are CD34+ cells.

CXCR4 is believed to be associated with increased homing and engraftment of hematopoietic stem and progenitor cells, and therefore the treated hematopoietic stem and progenitor cells of the invention have enhanced therapeutic properties, including for example, increased homing to bone marrow and ischemia-damaged tissue, as well as enhanced proliferative and regenerative properties.

In various embodiments, cells of the invention and compositions containing such enhanced cells are useful for treating conditions and disorders where increased numbers of hematopoietic stem and progenitor cells are needed or beneficial, including among other treatments, hematopoietic stem cell transplants and in treating ischemia-damaged tissue. Without wishing to be bound by theory, the present invention contemplates, in part, that the increased levels of CXCR4 protein on the surface of the enhanced hematopoietic stem and progenitor cells of the invention improve homing of the enhanced cells to the bone marrow and to sites of tissue injury. The enhanced hematopoietic stem and progenitor cells may improve patient outcome during stem cell transplants by increasing the efficacy of hematopoietic stem and progenitor cells used in stem cell transplants, including for example, by increasing homing and/or engraftment of treated cells to the bone marrow, and increasing the ability of treated cells to self-renew and proliferate in vivo after administration to a patient.

The enhanced hematopoietic stem and progenitor cells of the invention may improve patient outcome when used for treating ischemic tissue or ischemia-damaged tissue by, for example, improving vascularization in ischemic tissue, improving tissue regeneration at sites of ischemia, decreasing ischemic tissue necrosis or apoptosis, and/or increasing cell survival at sites of ischemia.

B. Definitions

The articles "a," "an," and "the" are used herein to refer to one or to more than one (i.e., to at least one) of the grammatical object of the article. By way of example, "an element" means one element or more than one element.

The use of the alternative (e.g., "or") should be understood to mean either one, both, or any combination thereof of the alternatives. As used herein, the terms "include" and "comprise" are used synonymously.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, +9%, ±8%, ±7%, ±6%, ±5%, ±4%, ±3%, ±2%, or ±1% about a reference quantity, level, value, number, frequency, percentage, dimension, size, amount, weight or length.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The recitations "ex vivo administration," "ex vivo treatment," or "ex vivo therapeutic use," relate generally to medical procedures in which one or more organs, cells, or tissues are obtained from a living or recently deceased subject, optionally purified/enriched, exposed to a treatment or procedure (e.g., an ex vivo administration step that involves incubating the cells with a composition or agent of the present invention to enhance expansion of particular cells, such as hematopoietic stem or progenitor cells). Cells treated ex vivo may be administered to the donor or to a different living subject.

Such ex vivo therapeutic applications may also include an optional in vivo treatment or procedural step, such as by administering contacted cells of the invention one or more times to the living subject. Both local and systemic administration is contemplated for these embodiments, according to well-known techniques in the art and as described elsewhere herein. The amount of cells administered to a subject will depend on the characteristics of that subject, such as general health, age, sex, body weight, and tolerance to drugs, as well as the degree, severity, and type of reaction to the drug and/or cell transplant.

The term "in vivo" refers generally to activities that take place inside an organism, such as cell engraftment, cell homing, self-renewal of cells, and expansion of cells. In one embodiment, the term "in vivo expansion" refers to the ability of a cell population to increase in number in vivo. In particular embodiments, the in vivo expansion include self-renewal and/or proliferation of stem cells.

By "enhance" or "promote," or "increase" or "activate" refers generally to the ability of an agent to produce or cause a greater physiological response (i.e., downstream effects) in a cell, as compared to the response caused by either vehicle or a control molecule/composition, e.g., increased engraftment/engraftment potential of hematopoietic stem and progenitor cells and increased in vivo stem cell expansion. A measurable physiological response may include an increase in hematopoietic stem and progenitor cell engraftment, viability, homing, self-renewal, and/or expansion, among others apparent from the understanding in the art and the description herein. In one embodiment, the increase can be an increase in gene expression as a result of increased signaling through the $PGE_2R_2$ and/or $PGE_2R_4$ cell signaling pathways, including, but not limited to an increase in CREB phosphorylation, an increase in CREM expression, and an increase in CXCR4 expression. Increases in hematopoietic stem and progenitor cell engraftment, viability, homing, self-renewal and/or in vivo expansion, can also be ascertained using methods known in the art, such as gene expression, CFU-C assays, CFU-S assays, CAFC assays, and cell surface protein expression, among others. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response produced by vehicle (the absence of an agent) or a control composition.

By "decrease" or "lower," or "lessen," or "reduce," or "abate" refers generally to the ability of an agent to produce or cause a lesser physiological response (i.e., downstream effects) in a cell, as compared to the response caused by either vehicle or a control molecule/composition, e.g., decreased apoptosis. In one embodiment, the decrease can be a decrease in gene expression or a decrease in cell signaling that normally is associated with a reduction of cell viability. An "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response produced by vehicle (the absence of an agent) or a control composition.

By "maintain," or "preserve," or "maintenance," or "no change," or "no substantial change," or "no substantial decrease" refers generally to the ability of a agent to produce or cause a comparable physiological response (i.e., downstream effects) in a cell, as compared to the response caused by either vehicle or a control molecule/composition (reference response). A comparable response is one that is not significantly different or measurably different from the reference response.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

In certain embodiments, therapeutic cells of the invention comprise a unique or substantially unique gene signature. As used herein, the term "gene expression profile," "gene expression signature" or "gene signature" refers to the levels of expression of multiple different genes measured for the same sample, i.e., a population of cells. A gene expression signature may be defined so as to identify a group of genes "signature genes" that serves to distinguish the therapeutic cells from existing cells in the art and/or control, vehicle, or non-treated cells.

A "signature gene", as used herein, means any gene in a signature gene set. For example, signature genes include hyaluronan synthase 1 (HAS1), GTP-binding protein GEM (GEM), dual specificity protein phosphatase 4 (DUSP4), amphiregulin (AREG), Nuclear receptor related 1 protein (NR4A2), renin (REN), cAMP-responsive element modulator (CREM), collagen, type I, alpha 1 (COL1A1), Fos-related antigen 2 (FOSL2), and CXC chemokine receptor 4 (CXCR4). For clarity, signature genes do not include housekeeping genes.

"Gene expression" as used herein refers to the relative levels of expression and/or pattern of expression of a gene in a biological sample, such as the stem and progenitor cells, or population of cells comprising stem or progenitor cells. In particular embodiments, the stem or progenitor cells are hematopoietic stem and progenitor cells.

Any methods available in the art for detecting expression of the genes characterizing the cells comprising the therapeutic composition of the invention are encompassed herein. As used herein, the term "detecting expression" means determining the quantity or presence of an RNA transcript or its expression product of a gene. Methods for detecting expression of genes, that is, gene expression profiling, include methods based on hybridization analysis of polynucleotides, methods based on sequencing of polynucleotides, immunohistochemistry methods, and proteomics-based methods. The methods generally detect expression products (e.g., mRNA) of the genes of interest. In some embodiments, PCR-based methods, such as reverse transcription PCR (RT-PCR) (Weis et al., TIG 8:263-64, 1992), and array-based methods such as microarray (Schena et al., Science 270:467-70, 1995) are used.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

C. Hematopoietic Stem and Progenitor Cells

The invention provides human hematopoietic stem and progenitor cells wherein the stem cells have been contacted ex vivo with one or more agents capable of increasing the therapeutic properties of the cell. In one embodiment, human hematopoietic stem and progenitor cells have been contacted ex vivo with one or more agents that increase CXCR4 gene expression in the cells. In one preferred embodiment, the gene expression of CXCR4 is increased in the treated human hematopoietic stem cells at least about 30 fold compared to non-contacted hematopoietic stem and progenitor cells or cells treated with a vehicle control.

Hematopoietic stem cells are multipotent stem cells that give rise to all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al., U.S. Pat. No. 5,635,387; McGlave, et al., U.S. Pat. No. 5,460,964; Simmons, P., et al, U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827). Hematopoietic progenitor cells (HSCs) give rise to committed hematopoietic progenitor cells (HPCs) that are capable of generating the entire repertoire of mature blood cells over the lifetime of an organism.

As used herein, the term "hematopoietic stem and progenitor cell" or "HSPC" refers to a cell identified by the presence of the antigenic marker CD34 (CD34$^+$) and are therefore characterized as CD34$^+$ cells, and populations of such cells. In particular embodiments, the term "HSPC" refers to a cell identified by the presence of the antigenic marker CD34 (CD34$^+$) and the absence of lineage (lin) markers and are therefore characterized as CD34$^+$/Lin(−) cells, and populations of such cells. It is recognized that the population of cells comprising CD34$^+$ and/or Lin(−) cells also includes hematopoietic progenitor cells, and so for the purposes of this application the term "HSPC" includes hematopoietic progenitor cells.

"Enhanced hematopoietic stem and progenitor cell" or "enhanced HSPC" refers to a HSPC treated ex vivo with one or more agents that increase CXCR4 gene expression in the cell at least about 30 fold compared to control, vehicle or untreated cells.

As used herein, a "non-contacted" or an "untreated" cell is a cell that has not been treated, e.g., cultured, contacted, or incubated with an agent other than a control agent. Cells contacted with DMSO (a control agent), or contacted with another vehicle are non-contacted cells.

The HSPCs of the invention are identified and are characterized by, a gene expression profile indicating high levels of CXCR4 expression. The HSPCs can also be characterized based upon increased CXCR4 gene expression and increased cell surface expression of CXCR4 polypeptide. In certain embodiments, the CXCR4 gene expression in the HSPCs of the invention is increased by at least 30, 35, 40, 45, 50, 55, 60, 65, 70, 75, 80, 85, 90, 95, or 100 fold compared to the expression of CXCR4 in non-contacted cells.

In particular embodiments, CXCR4 gene expression in the HSPCs is increased by about 30 to about 80 fold compared to untreated HSPCs. In further embodiments, CXCR4 gene expression in the HSPCs is increased by about 40 to about 80 fold, about 50 to about 80 fold, about 60 to about 80 fold, or about 50 to about 70 fold, compared to untreated HSPCs.

CXCR4 gene expression or the gene expression signature of the treated HSPCs of the invention may be determined after the cells are treated with one or more agents. For example, HSPCs may be treated ex vivo with one or more agents, washed to remove the agent(s), and the gene expression analyzed without further incubation of the cells.

Human HSPCs contacted in the methods of the invention and having enhanced therapeutic properties can also be characterized in multiple and various other ways, such as by increased levels of intracellular cAMP signaling, e.g., CREB phosphorylation, or as determined by a biochemical assay; gene expression signatures indicating upregulation of genes implicated in the $PGE_2R_2/R4$ cell signaling pathway, e.g., CREM, and genes that increase stem and progenitor cell homing and engraftment, e.g., CXCR4, as determined by gene expression assays, e.g., microarrays; no measurable decrease in stem and progenitor cell viability as determined by cell viability assays, e.g., 7-aminoactinomycinD (7-AAD) staining; and/or an increased capacity of stem cells to self-renew as determined by an in vitro colony forming units (CFU-C) assay, for example.

1. Determining Gene Expression

"Gene expression" as used herein refers to the relative levels of expression and/or pattern of expression of a gene, such as CXCR4, in a biological sample, such as stem and progenitor cells, or a population of cells comprising stem or progenitor cells, in a therapeutic composition of the invention. A sample may comprise heterogeneous or homogenous population of cells and the cell populations may be purified or not purified from the sample. The expression of a gene, such as CXCR4, may be measured at the level of cDNA, RNA, mRNA, or combinations thereof.

Any methods available in the art for detecting expression of the CXCR4 gene are encompassed herein. As used herein, the term "detecting expression" means determining the quantity or presence of an RNA transcript or its expression product of a gene. Methods for detecting expression of genes include methods based on PCR, hybridization analysis of polynucleotides, methods based on sequencing of polynucleotides, immunohistochemistry methods, and proteomics-based methods. The methods generally detect expression products (e.g., mRNA) of the genes of interest. In some embodiments, PCR-based methods, such as reverse transcription PCR (RT-PCR) (Weis et al., TIG 8:263-64, 1992), and array-based methods such as microarray (Schena et al., Science 270:467-70, 1995) are used.

General methods for RNA extraction are well known in the art and are disclosed in standard textbooks of molecular biology, including Ausubel et al., ed., *Current Protocols in Molecular Biology*, John Wiley & Sons, New York 1987-1999. In particular, RNA isolation can be performed using a purification kit, a buffer set and protease from commercial manufacturers, such as Qiagen (Valencia, Calif.), according to the manufacturer's instructions. For example, total RNA from cells in culture can be isolated using Qiagen RNeasy mini-columns. Isolated RNA can be used in hybridization or amplification assays that include, but are not limited to, PCR analyses and probe arrays. One method for the detection of RNA levels involves contacting the isolated RNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 60, 100, 250, or 500 nucleotides in length and sufficient to specifically hybridize under stringent conditions to an intrinsic gene of the present invention, or any derivative DNA or RNA. Hybridization of an mRNA with the probe indicates that the intrinsic gene in question is being expressed.

An alternative method for determining the level of gene expression in a sample involves the process of nucleic acid amplification, for example, by RT-PCR (U.S. Pat. No. 4,683, 202), ligase chain reaction (Barany, *Proc. Natl. Acad. Sci. USA* 88:189-93, 1991), self sustained sequence replication (Guatelli et al., *Proc. Natl. Acad. Sci. USA* 87:1874-78, 1990), transcriptional amplification system (Kwoh et al., *Proc. Natl. Acad. Sci. USA* 86:1173-77, 1989), Q-Beta Replicase (Lizardi et al., *Bio/Technology* 6:1197, 1988), rolling circle replication (U.S. Pat. No. 5,854,033), or any other nucleic acid amplification method, followed by the detection of the amplified molecules using techniques well known to those of skill in the art.

In particular aspects of the invention, gene expression of CXCR4 is assessed by quantitative RT-PCR. Numerous different PCR or QPCR protocols are known in the art and exemplified herein below and can be directly applied or adapted for use using the presently-described compositions for the detection and/or quantification of CXCR4. Quantitative PCR (QPCR) (also referred as real-time PCR) is preferred under some circumstances because it provides not only a quantitative measurement, but also reduced time and contamination. In some instances, the availability of full gene expression profiling techniques is limited due to requirements for fresh frozen tissue and specialized laboratory equipment, making the routine use of such technologies difficult in a clinical setting. As used herein, "quantitative PCR (or "real time QPCR") refers to the direct monitoring of the progress of PCR amplification as it is occurring without the need for repeated sampling of the reaction products. In quantitative PCR, the reaction products may be monitored via a signaling mechanism (e.g., fluorescence) as they are generated and are tracked after the signal rises above a background level but before the reaction reaches a plateau. The number of cycles required to achieve a detectable or "threshold" level of fluorescence varies directly with the concentration of amplifiable targets at the beginning of the PCR process, enabling a measure of signal intensity to provide a measure of the amount of target nucleic acid in a sample in real time.

"Normalization" may be used to remove sample-to-sample variation. For microarray data, the process of normalization aims to remove systematic errors by balancing the fluorescence intensities of the two labeling dyes. The dye bias can come from various sources including differences in dye labeling efficiencies, heat and light sensitivities, as well as scanner settings for scanning two channels. Some commonly used methods for calculating normalization factor include: (i) global normalization that uses all genes on the array, such as by log scale robust multi-array analysis (RMA); (ii) housekeeping genes normalization that uses constantly expressed housekeeping/invariant genes; and (iii) internal controls normalization that uses known amount of exogenous control genes added during hybridization (Quackenbush (2002) *Nat. Genet.* 32 (Suppl.), 496-501). In one embodiment, expression of the genes disclosed herein can be determined by normalizing the expression to control housekeeping gene expression or by performing log scale robust multi-array analysis (RMA).

2. Gene Expression Profile of Stem or Progenitor Cells

The therapeutic compositions comprise a population of treated stem or progenitor cells having increased therapeutic properties related to the treatment of ischemic tissue. Without wishing to be bound to any particular theory, treatment of the cells with a prostaglandin pathway agonist and/or a glucocorticoid imbues the cells with the increased therapeutic properties useful for treating ischemic tissue or more or more symptoms associated with an ischemic tissue. Cells that have the increased therapeutics properties are characterized by increased CXCR4 gene expression and increased cell surface expression of CXCR4 polypeptide. In a particular embodiment, the therapeutic composition comprises hematopoietic stem or progenitor cells characterized by increased levels of gene and cell-surface CXCR4 expression.

Stem or progenitor cells, e.g., hematopoietic stem or progenitor cells, treated with a prostaglandin pathway agonist and a glucocorticoid can be characterized by at least a 40, 45, 50, 55, 60, 65, 70, 75, or 80 fold increase in CXCR4 gene expression compared to the expression of CXCR4 in untreated cells.

Cells that have increased therapeutic properties can further characterized by a unique gene expression signature wherein expression of 1, 2, 3, 4, 5, 6, 7, 8, 9, or all 10 of the signature genes selected from the group consisting of: CXCR4, hyaluronan synthase 1 (HAS1), GTP-binding protein GEM (GEM), dual specificity protein phosphatase 4 (DUSP4), amphiregulin (AREG), Nuclear receptor related 1 protein (NR4A2), renin (REN), cAMP-responsive element modulator (CREM), collagen, type I, alpha 1 (COL1A1), and Fos-related antigen 2 (FOSL2) is increased, compared to untreated cells.

In other particular embodiments, hematopoietic stem or progenitor cells treated with a prostaglandin pathway agonist and a glucocorticoid have a gene expression signature, wherein 1, 2, 3, 4, 5, 6, 7, 8, 9, 10 or more of the signature genes is increased by at least 40, 45, 50, 55, 60, 65, 70, 75, or 80 fold compared to untreated cells. In some embodiments, the average fold change of all signature genes is at least about 15, 20, 25, 30, or 35 fold. In some embodiments, the average fold change of all signature genes is at least about 25, or 30 fold.

The gene expression or gene expression signature of the treated stem or progenitor cells may be determined after cells are treated with an agent, or cells may be incubated for some period of time after treatment before determining the gene expression signature of the cells. For example, cells may be treated ex vivo with one or more agents, washed to remove the agents, and the gene expression analyzed without further incubation of the cells. Alternatively, in some embodiments, cells are treated with one or more agents, washed to remove the agents from the cell population, and then the cells are incubated ex vivo for some period of time prior to analyzing the gene expression signature of the cells.

3. Sources of HSPCs

The HSPCs prepared in the methods of the invention may be obtained from any suitable source of hematopoietic stem and progenitor cells, and may be provided, and treated, as a highly purified population of HSPCs (a homogenous population), or as a composition that comprises from 0.01% to about 100% of HSPCs (a heterogeneous population). For example, and without limitation, HSPCs may be provided in compositions such as unfractionated bone marrow (in which $CD34^+$ cells comprise less than about 1% of the bone marrow cell population), umbilical cord blood, placental blood, placenta, fetal blood, fetal liver, fetal spleen, Wharton's jelly, or mobilized peripheral blood.

Suitable sources of HSPCs for use in the methods of the invention include, but are not limited to, cells isolated or obtained from an organ of the body containing cells of hematopoietic origin. By "isolated" is meant material that is removed from its original environment. For example, a cell is isolated if it is separated from some or all of the components that normally accompany it in its native state. For example, an "isolated population of cells," an "isolated source of cells," or "isolated HSPCs" and the like, as used herein, refer to in vitro or ex vivo separation of one or more cells from their natural cellular environment, and from association with other components of the tissue or organ, i.e., it is not significantly associated with in vivo substances.

HSPCs can be obtained or isolated from bone marrow of adults, which includes femurs, hip, ribs, sternum, and other bones. Bone marrow aspirates containing HSPCs can be obtained or isolated directly from the hip using a needle and syringe. Other sources of HSPCs include umbilical cord blood, placental blood, mobilized peripheral blood, Wharton's jelly, placenta, fetal blood, fetal liver, or fetal spleen. In particular embodiments, harvesting a sufficient quantity of HSPCs for use in therapeutic applications may require mobilizing the stem and progenitor cells in the donor.

"Hematopoietic stem cell mobilization" refers to the release of stem cells from the bone marrow into the peripheral blood circulation for the purpose of leukapheresis, prior to stem cell transplantation. By increasing the number of stem cells harvested from the donor, the number of stem cells available for therapeutic applications can be significantly improved. Hematopoietic growth factors, e.g., granulocyte colony stimulating factor (G-CSF) or chemotherapeutic agents often are used to stimulate the mobilization. Commercial stem cell mobilization drugs exist and can be used in combination with G-CSF to mobilize sufficient quantities of hematopoietic stem and progenitor cells for transplantation into a subject. For example, G-CSF and Mozobil™ (Genzyme Corporation) can be administered to a donor in order to harvest a sufficient number of hematopoietic cells for transplantation. Other methods of mobilizing hematopoietic stem and progenitor cells would be apparent to one having skill in the art.

In particular embodiments, HSPCs are obtained from umbilical cord blood. Cord blood can be harvested according to techniques known in the art (see, e.g., U.S. Pat. Nos. 7,147,626 and 7,131,958, herein incorporated by reference for such methodologies).

In one embodiment, HSPCs can be obtained from pluripotent stem cell sources, e.g., induced pluripotent stem cells (iPSCs) and embryonic stem cells (ESCs). As used herein, the term "induced pluripotent stem cell" or "iPSC" refers to a non-pluripotent cell that has been reprogrammed to a pluripotent state. Once the cells of a subject have been reprogrammed to a pluripotent state, the cells can then be programmed to a desired cell type, such as a hematopoietic stem or progenitor cell. As used herein, the term "reprogramming" refers to a method of increasing the potency of a cell to a less differentiated state. As used herein, the term "programming" refers to a method of decreasing the potency of a cell or differentiating the cell to a more differentiated state.

4. Therapeutic Cellular Compositions

The invention also provides therapeutic compositions comprising the enhanced HSPCs described herein. In particular, the therapeutic compositions of the invention comprise a population of cells comprising HSPCs wherein the HSPCs have been contacted ex vivo with one or more agents capable of increasing CXCR4 gene expression in the HSPCs, and wherein the gene expression of CXCR4 is increased in the HSPCs by at least about 30 fold relative to non-contacted HSPCs. In one embodiment, the therapeutic compositions of the invention comprise a population of cells comprising HSPCs treated ex vivo with a prostaglandin pathway agonist and a glucocorticoid. In certain embodiments, the therapeutic composition comprising the enhanced HSPCs is whole bone marrow, umbilical cord blood, or mobilized peripheral blood.

In particular embodiments, the therapeutic composition comprises a population of cells, wherein the population of cells is about 95% to about 100% HSPCs. The invention contemplates, in part, that using therapeutic compositions of highly purified HSPCs, e.g., a composition comprising a population of cells wherein the cells comprise about 95% HSPCs, may improve the efficiency of stem cell therapies. Currently practiced methods of transplantations typically use unfractionated mixtures of cells where HSPCs comprise less than 1% of the total cell population.

In some embodiments, the therapeutic composition comprises a population of cells, wherein the population of cells comprises less than about 0.1%, 0.5%, 1%, 2%, 5%, 10%, 15%, 20%, 25%, or 30% HSPCs. The population of cells in some embodiments comprises less than about 0.1%, 0.5%, 1%, 2%, 5%, 10%, 15%, 20%, 25%, or 30% HSPCs. In other embodiments, the population of cells is about 0.1% to about 1%, about 1% to about 3%, about 3% to about 5%, about 10%-about 15%, about 15%-20%, about 20%-25%, about 25%-30%, about 30%-35%, about 35%-40%, about 40%-45%, about 45%-50%, about 60%-70%, about 70%-80%, about 80%-90%, about 90%-95%, or about 95% to about 100% HSPCs.

In particular embodiments, the population of cells is about 0.1% to about 1%, about 1% to about 3%, about 3% to about 5%, about 10%-about 15%, about 15%-20%, about 20%-25%, about 25%-30%, about 30%-35%, about 35%-40%, about 40%-45%, about 45%-50%, about 60%-70%, about 70%-80%, about 80%-90%, about 90%-95%, or about 95% to about 100% HSPCs.

HSPCs in the therapeutic compositions of the invention can be autologous/autogeneic ("self") or non-autologous ("non-self," e.g., allogeneic, syngeneic or xenogeneic) relative to a subject to which the therapeutic composition is to be administered. "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In particular embodiments, the HSPCs of the invention are allogeneic or autologous.

HSPCs for use in the methods of the present invention may be depleted of mature hematopoietic cells such as T cells, B cells, NK cells, dendritic cells, monocytes, granulocytes, erythroid cells, and their committed precursors from bone marrow aspirate, umbilical cord blood, or mobilized peripheral blood (mobilized leukapheresis product). Mature, lineage committed cells are depleted by immunodepletion, for example, by labeling solid substrates with antibodies that bind to a panel of so-called "lineage" antigens: CD2, CD3, CD11b, CD14, CD15, CD16, CD19, CD56, CD123, and CD235a. A subsequent step can be performed to further purify the population of cells, in which a substrate labeled with antibodies that bind to the CD34$^+$ antigen are used to isolate primitive hematopoietic stem and progenitor cells. Kits are commercially available for purifying stem and progenitor cells from various cell sources and in particular embodiments, these kits are suitable for use with the methods of the present invention. Exemplary commercially available kits for purifying stem and progenitor cells include, but are not limited to Lineage (Lin) Depletion Kit (Miltenyi Biotec); CD34$^+$ enrichment kit (Miltenyi Biotec); RosettaSep (Stem Cell Technologies).

In one embodiment, the amount of HSPCs in the therapeutic composition is at least $0.1 \times 10^5$ cells, at least $0.5 \times 10^5$ cells, at least $1 \times 10^5$ cells, at least $5 \times 10^5$ cells, at least $10 \times 10^5$ cells, at least $0.5 \times 10^6$ cells, at least $0.75 \times 10^6$ cells, at least $1 \times 10^6$ cells, at least $1.25 \times 10^6$ cells, at least $1.5 \times 10^6$ cells, at least $1.75 \times 10^6$ cells, at least $2 \times 10^6$ cells, at least $2.5 \times 10^6$ cells, at least $3 \times 10^6$ cells, at least $4 \times 10^6$ cells, at least $5 \times 10^6$ cells, at least $10 \times 10^6$ cells, at least $15 \times 10^6$ cells, at least $20 \times 10^6$ cells, at least $25 \times 10^6$ cells, or at least $30 \times 10^6$ cells.

In a particular embodiment, the amount of HSPCs in the therapeutic composition is about $0.1 \times 10^5$ cells to about $10 \times 10^5$ cells; about $0.5 \times 10^6$ cells to about $5 \times 10^6$ cells; about $1 \times 10^6$ cells to about $3 \times 10^6$ cells; about $1.5 \times 10^6$ cells to about $2.5 \times 10^6$ cells; or about $2 \times 10^6$ cells to about $2.5 \times 10^6$ cells.

In a particular embodiment, the amount of HSPCs in the therapeutic composition is about $1 \times 10^6$ cells to about $3 \times 10^6$ cells; about $1.0 \times 10^6$ cells to about $5 \times 10^6$ cells; about $1.0 \times 10^6$ cells to about $10 \times 10^6$ cells, about $10 \times 10^6$ cells to about $20 \times 10^6$ cells, about $10 \times 10^6$ cells to about $30 \times 10^6$ cells, or about $20 \times 10^6$ cells to about $30 \times 10^6$ cells.

In another embodiment, the amount of HSPCs in the therapeutic composition is about $1 \times 10^6$ cells to about $30 \times 10^6$ cells; about $1.0 \times 10^6$ cells to about $20 \times 10^6$ cells; about $1.0 \times 10^6$ cells to about $10 \times 10^6$ cells, about $2.0 \times 10^6$ cells to about $30 \times 10^6$ cells, about $2.0 \times 10^6$ cells to about $20 \times 10^6$ cells, or about $2.0 \times 10^6$ cells to about $10 \times 10^6$ cells.

In a particular embodiment, the amount of HSPCs in the therapeutic composition is about $1 \times 10^6$ HSPCs, about $2 \times 10^6$ cells, about $5 \times 10^6$ cells, about $7 \times 10^6$ cells, about $10 \times 10^6$ cells, about $15 \times 10^6$ cells, about $17 \times 10^6$ cells, about $20 \times 10^6$ cells about $25 \times 10^6$ cells, or about $30 \times 10^6$ cells.

In one embodiment, the amount of HSPCs in the therapeutic composition is the amount of HSPCs in a partial or single cord of blood, or is at least $0.1 \times 10^5$ cells/kg of bodyweight, at least $0.5 \times 10^5$ cells/kg of bodyweight, at least $1 \times 10^5$ cells/kg of bodyweight, at least $5 \times 10^5$ cells/kg of bodyweight, at least $10 \times 10^5$ cells/kg of bodyweight, at least $0.5 \times 10^6$ cells/kg of bodyweight, at least $0.75 \times 10^6$ cells/kg of bodyweight, at least $1 \times 10^6$ cells/kg of bodyweight, at least $1.25 \times 10^6$ cells/kg of bodyweight, at least $1.5 \times 10^6$ cells/kg of bodyweight, at least $1.75 \times 10^6$ cells/kg of bodyweight, at least $2 \times 10^6$ cells/kg of bodyweight, at least $2.5 \times 10^6$ cells/kg of bodyweight, at least $3 \times 10^6$ cells/kg of bodyweight, at least $4 \times 10^6$ cells/kg of bodyweight, at least $5 \times 10^6$ cells/kg of bodyweight, at least $10 \times 10^6$ cells/kg of bodyweight, at least $15 \times 10^6$ cells/kg of bodyweight, at least $20 \times 10^6$ cells/kg of bodyweight, at least $25 \times 10^6$ cells/kg of bodyweight, or at least $30 \times 10^6$ cells/kg of bodyweight.

D. Methods of Preparing the Enhanced Cells of the Invention

The invention contemplates in part, methods of preparing HSPCs characterized by increased levels of CXCR4 gene expression. In a particular embodiment, the method of preparing the HSPCs comprises treating HSPCs ex vivo with one or more agents capable of increasing CXCR4 gene expression in the contacted cells under conditions sufficient to increase CXCR4 gene expression at least 30, 40, 50, 60, 70, or 80 fold in the contacted cells compared to non-contacted cells. In one embodiment, method of preparing the HSPCs of the invention comprises treating HSPCs ex vivo with a prostaglandin pathway agonist and a glucocorticoid.

As used herein, the terms "conditions sufficient," or "under conditions sufficient," refer to the conditions for treating the HSPCs with one or more agents to increase CXCR4 gene expression in the cells to surprising and unexpected levels compared to control, vehicle, or non-treated cells.

Conditions include, but are not limited to the source of the cells, the agents used to treat the cells and concentrations of agent(s), the time the cells are exposed to the agent(s), and the temperature of treatment.

1. Agents Useful in Preparing Enhanced Cells

As used herein, "agent" refers to a compound or molecule capable of increasing CXCR4 gene expression in HSPCs treated with the agent, and refers to compounds that increase CXCR4 expression when used either alone or in combination with another compound or molecule. In particular embodiments of the invention, a combination of two or more agents that act synergistically to increase CXCR4 gene expression in HSPCs treated with the combination is used in preparing the enhanced HSPCs. Particular agents include, for example, compounds capable of stimulating the prostaglandin pathway, e.g., prostaglandin pathway agonists, as well as glucocorticoids.

2. Prostaglandin Pathway Agonists

As used herein, the term "prostaglandin pathway agonist" refers to an agent that stimulates prostaglandin cell signaling pathways, including an agent that stimulates the $PGE_2R_2$ and/or $PGE_2R_4$ cell signaling pathways, and increases CXCR4 gene expression in the cells. Illustrative examples of prostaglandin pathway agonists that are suitable for use in preparing cells of the invention, include, but are not limited to, $PGE_2$, $dmPGE_2$, 15(S)-15-methyl $PGE_2$, 20-ethyl $PGE_2$, 8-iso-16-cyclohexyl-tetranor $PGE_2$, and $PGE_2$ analogues. In certain embodiments, $PGE_2R_2$ and $PGE_2R_4$ agonists and analogues thereof are of particular interest, and in some embodiments, the agent preferentially binds and activates a $PGE_2$ $EP_2$ or $PGE_2$ $EP_4$ receptor.

As used herein, the terms "prostaglandin $E_2$" or "$PGE_2$" include, without limitation, any naturally-occurring or chemically synthesized $PGE_2$ molecule, as well as "analogues" thereof. As used herein, the term "analogue" or relates to a chemical molecule that is similar to another chemical substance, e.g., $PGE_2$, in structure and function, often differing structurally by a single element or group, but may differ by modification of more than one group (e.g., 2, 3, or 4 groups) if it retains the same function as the parental chemical. Such modifications are routine to persons skilled in the art, and include, for example, additional or substituted chemical moieties, such as esters or amides of an acid, protecting groups such as a benzyl group for an alcohol or thiol, and tert-butoxylcarbonyl groups for an amine. Also included are modifications to alkyl side chains, such as alkyl substitutions (e.g., methyl, dimethyl, ethyl, etc.), modifications to the level of saturation or unsaturation of side chains, and the addition of modified groups such as substituted phenyl and phenoxy. Analogues can also include conjugates, such as biotin or avidin moieties, enzymes such as horseradish peroxidase and the like, and including radio-labeled, bioluminescent, chemoluminescent, or fluorescent moieties. Also, moieties may be added to the agents described herein to alter their pharmacokinetic properties, such as to increase half-life in vivo or ex vivo, or to increase their cell penetration properties, among other desirable properties. Also included are prodrugs, which are known to enhance numerous desirable qualities of pharmaceuticals (e.g., solubility, bioavailability, manufacturing, etc.) (see, e.g., WO/2006/047476 for exemplary EP agonist prodrugs, which is incorporated by reference for its disclosure of such agonists).

Illustrative examples of $PGE_2$ "analogues" include, without limitation, 16,16-dimethyl $PGE_2$ ("$dmPGE_2$"), 16,16-dimethyl $PGE_2$ p-(p-acetamidobenzamido) phenyl ester, 11-deoxy-16,16-dimethyl $PGE_2$, 9-deoxy-9-methylene-16,16-dimethyl $PGE_2$, 9-deoxy-9-methylene $PGE_2$, 9-keto Fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15(S)-15-methyl $PGE_2$, 15(R)-15-methyl $PGE_2$, 8-iso-15-keto $PGE_2$, 8-iso $PGE_2$ isopropyl ester, 8-iso-16-cyclohexyl-tetranor $PGE_2$, 20-hydroxy $PGE_2$, 20-ethyl $PGE_2$, 11-deoxy PGEZ, nocloprost, sulprostone, butaprost, 15-keto $PGE_2$, and 19 (R) hydroxy $PGE_2$. Also included are PG analogues or derivatives having a similar structure to $PGE_2$ that are substituted with halogen at the 9-position (see, e.g., WO 2001/12596, herein incorporated by reference in its entirety), as well as 2-decarboxy-2-phosphinico prostaglandin derivatives, such as those described in U.S. Publication No. 2006/0247214, herein incorporated by reference in its entirety).

$PGE_1$ analogues, including without limitation alprostadil, can also be used to activate the $PGE_2R_2$ ($EP_2$) and $PGE_2R_4$ ($EP_4$) cell signaling pathways, and are contemplated as agents useful in the methods of the invention.

Stimulation/activation of the $PGE_2R_2$ ($EP_2$) and $PGE_2R_4$ ($EP_4$) cell signaling pathways are contemplated to underlie the physiological responses in HSPCs that increase engraftment, maintain cell viability, and increase homing and proliferation of the cells. Accordingly, in one embodiment, a "non-$PGE_2$-based ligand" that binds to and stimulates $PGE_2R_2$ and $PGE_2R_4$ receptors (i.e., a $PGE_2R_2/PGE_2R_4$ agonist) is contemplated for use in the methods of the invention.

Illustrative examples of non-$PGE_2$-based $EP_2$ receptor agonists include CAY10399, ONO_8815Ly, ONO-AE1-259, CP-533,536 and carbazoles and fluorenes disclosed in WO 2007/071456.

Illustrative examples of non-$PGE_2$-based $EP_4$ agonists include ONO-4819, APS-999 Na, AH23848, ONO-AE1-329, and other non-$PGE_2$-based $EP_4$ agonists disclosed in WO/2000/038663; U.S. Pat. No. 6,747,037; and U.S. Pat. No. 6,610,719).

Agents selective for the $PGE_2$ $EP_4$ receptor preferentially bind to and activate $PGE_2$ $EP_4$ receptors. Such agents have a higher affinity for the $EP_4$ receptor than for any of the other three EP receptors namely $EP_1$, $EP_2$ and $EP_3$. Agents that selectively bind the PGE $EP_4$ receptor include, but are not limited to, agents selected from the group consisting of: 5-[(1E,3R)-4,4-difluoro-3-hydroxy-4-phenyl-1-buten-1-yl]-1-[6-(2H-tetrazol-5R-yl)hexyl]-2-pyrrolidinone; 2-[3-[(1R, 2S,3R)-3-hydroxy-2-[(E,3S)-3-hydroxy-5-[2-(methoxymethyl)phenyl]pent-1-enyl]-5-oxocyclopentyl]sulfanylpropylsulfanyl]acetic acid; methyl 4-[2-[(1R,2R,3R)-3-hydroxy-2-[(E,3S)-3-hydroxy-4-[3-(methoxymethyl)phenyl]but-1-enyl]-5-oxocyclopentyl]ethylsulfanyl]butanoate; 16-(3-Methoxymethyl)phenyl-ro-tetranor-5-thiaPGE; 5-{3-[(2S)-2-{(3R)-3-hydroxy-4-[3-(trifluoromethyl)phenyl]butyl}-5-oxopyrrolidin-1-yl]propyl]thiophene-2-carboxylate; [4'-[3-butyl-5-oxo-1-(2-trifluoromethyl-phenyl)-1,5-dihydro-[1,2,4]triazol-4-ylmethyl]-biphenyl-2-sulfonic acid (3-methyl-thiophene-2-carbonyl)-amide]; and ((Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid), and pharmaceutically acceptable salts of any of these agents.

In particular embodiments, the prostaglandin pathway agonist is $PGE_2$, $dmPGE_2$, 15(S)-15-methyl $PGE_2$, 20-ethyl $PGE_2$, or 8-iso-16-cyclohexyl-tetranor $PGE_2$.

3. Glucocorticoids

Illustrative examples of glucocorticoids and glucocorticoid receptor agonists suitable for use in the methods of the invention include, but are not limited to, medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol, as well as combinations thereof.

In particular embodiments, the glucocorticoid comprises medrysone, hydrocortisone, triamcinolone, alclometasone, or dexamethasone. In more particular embodiments, the glucocorticoid is medrysone.

4. Combinations of Agents

Combinations of agents can also be used in preparing the enhanced HSPCs of the invention, and in particular embodiments treating HSPCs with a combination of agents results in an unexpected synergistic increase in CXCR4 gene and protein expression in treated cells. In particular, HSPCs treated with combinations of prostaglandin pathway agonists and glucocorticoids exhibit an unexpectedly high increase in CXCR4 gene and protein expression, and this correlates to improved therapeutic properties of the treated cells compared to control, vehicle, or non-treated cells.

In particular embodiments of the invention, the HSPCs are treated with a combination of one or more prostaglandin pathway agonists and one or more glucocorticoids.

In particular embodiments of the invention, the prostaglandin pathway agonist in the combination is a compound that selectively binds the $PGE_2$ $EP_2$ or the $PGE_2$ $EP_4$ receptor. In other embodiments of the invention, the prostaglandin pathway agonist comprises $PGE_2$, or a $PGE_2$ analogue or derivative thereof. In particular embodiments, the prostaglandin pathway agonist is $PGE_2$, $dmPGE_2$, 15(S)-15-methyl $PGE_2$, 20-ethyl $PGE_2$, or 8-iso-16-cyclohexyl-tetranor $PGE_2$. In more particular embodiments of the invention, the prostaglandin pathway agonist is $PGE_2$ or 16,16-dimethyl $PGE_2$.

In some embodiments, the glucocorticoid in the combination is selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol.

In more particular embodiments, the glucocorticoid in the combination comprises medrysone, hydrocortisone, alclometasone, dexamethasone, methylprednisolone, or triamcinolone. In one embodiment, the glucocorticoid is medrysone.

In some embodiments, the HSPCs are treated with a combination comprising a prostaglandin pathway agonist selected from the group consisting of $PGE_2$, $dmPGE_2$, 15(S)-15-methyl $PGE_2$, 20-ethyl $PGE_2$, and 8-iso-16-cyclohexyl-tetranor $PGE_2$ and one or more glucocorticoids. In a particular embodiment, the HSPCs are treated with a combination comprising $PGE_2$ or $dmPGE_2$ and a glucocorticoid.

In some embodiments, the HSPCs are treated with a combination comprising a prostaglandin pathway agonist selected from the group consisting of $PGE_2$, $dmPGE_2$, 15(S)-15-methyl $PGE_2$, 20-ethyl $PGE_2$, and 8-iso-16-cyclohexyl-tetranor $PGE_2$, and a glucocorticoid selected from the group consisting of medrysone, hydrocortisone, alclometasone, dexamethasone, methylprednisolone, or triamcinolone.

In other embodiments, the combination comprises $PGE_2$ or $dmPGE_2$ and medrysone, hydrocortisone, alclometasone, dexamethasone, methylprednisolone, or triamcinolone. In more particular embodiments, the HSPCs are treated with a combination comprising $PGE_2$ or $dmPGE_2$ and medrysone.

5. Formulations of Agents

Using cGMP practices, agents useful in preparing the therapeutic composition of the invention can be formulated in an organic solvent, such as methyl acetate, for use in contacting the cells of the invention, and may be supplied in an endotoxin free vessel. Agents contemplated by the invention are suitable for ex vivo administration to mammalian cells, as described herein. In certain embodiments, the solvent is typically a suitable organic solvent, as described herein (e.g., DMSO, DMF, DME, etc., including combinations or mixtures thereof). One or more solvents may be combined at certain ratios. For instance, a mixture of two solvents may be combined at a ratio of 9.5:0.5, 9:1, 8:2, 7:3, 6:4, 5:5, etc., including all integers and decimal points.

The recitation "organic solvent" or "suitable organic solvent" relates generally to carbon containing liquids or gases that dissolve a solid, liquid, or gaseous solute, resulting in a solution. A "suitable" organic solvent is one that is appropriate for ex vivo administration to, or incubation with, mammalian cells, and may also be appropriate for in vivo administration to a subject, such as by having minimal toxicity or other inhibitory effects under ex vivo conditions (e.g., cell culture) or in vivo at a selected concentration for the time of incubation or administration. A suitable organic solvent should also be appropriate for storage stability and handling of the agents described herein. Examples of suitable organic solvents include, but are not limited to, dimethyl sulfoxide (DMSO), N,N-dimethylformamide (DMF), dimethoxyethane (DME), and dimethylacetamide, including mixtures or combinations thereof. In certain embodiments, a composition or organic solvent is "substantially free" of methyl acetate, meaning that there should be no more than trace amounts of methyl acetate in the composition or solvent, and preferably undetectable amounts (e.g., as measured by high pressure liquid chromatography (HPLC), gas chromatography (GC), etc.).

As used herein, the term "endotoxin free" refers to vessels and/or compositions that contain at most trace amounts (i.e., amounts having no adverse physiological effects to a subject) of endotoxin, and preferably undetectable amounts of endotoxin. By "substantially free of endotoxin" is meant that there is less endotoxin per dose of cells than is allowed by the FDA for a biologic, which is a total endotoxin of 5 EU/kg body weight per day, which for an average 70 kg person is 350 EU per total dose of cells. In one embodiment, the term "endotoxin free" refers to a vessel and/or compositions that is at least 95%, at least 96%, at least 97%, at least 98%, at least 99%, or 100% endotoxin free. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipooligosaccharides (LOS) found in the outer membrane of various Gram-negative bacteria, and which represent a central pathogenic feature in the ability of these bacteria to cause disease. Small amounts of endotoxin in humans can produce fever, a lowering of the blood pressure, and activation of inflammation and coagulation, among other adverse physiological effects. Therefore, it is often desirable to remove most or all traces of endotoxin from drug product containers, because even small amounts may cause adverse effects in humans. Endotoxins can be removed from vessels using methods known in the art, for example, vessels can be cleaned in HEPA filtered washing equipment with endotoxin-free water, depyrogenated at 250° C., and clean-packaged in HEPA filtered workstations located inside a class 100/10 clean room (e.g., a class 100 clean room, contains no more than 100 particles bigger than half a micron in a cubic foot of air).

In particular embodiments, the HSPCs are treated (e.g., contacted) with one or more agents, each at a final concentration of about 1 µM to about 100 µM. In certain embodiments, HSPCs are treated with one or more agents, each at a final concentration of about $1\times10^{-14}$ M to about $1\times10^{-3}$ M, about $1\times10^{-13}$ M to about $1\times10^{-4}$ M, about $1\times10^{-12}$ M to about $1\times10^{-5}$ M, about $1\times10^{-11}$ M to about $1\times10^{-4}$ M, about $1\times10^{-11}$ M to about $1\times10^{-5}$ M, about $1\times10^{-10}$ M to about $1\times10^{-4}$ M, about $1\times10^{-10}$ M to about $1\times10^{-5}$ M, about $1\times10^{-9}$ M to about $1\times10^{-4}$ M, about $1\times10^{-9}$ M to about $1\times10^{-5}$ M, about $1\times10^{-8}$ M to about $1\times10^{-4}$ M, about $1\times10^{-7}$ M to about $1\times10^{-4}$ M, about $1\times10^{-6}$ M to about $1\times10^{-4}$ M, or any intervening ranges of final concentrations.

In another particular embodiment, HSPCs are treated with one or more agents, each at a final concentration of about $1\times10^{-14}$ M, about $1\times10^{-13}$ M, about $1\times10^{-12}$ M, about $1\times10^{-10}$ M, about $1\times10^{-9}$ M, about $1\times10^{-8}$ M, about $1\times10^{-7}$ M to about $1\times10^{-6}$ M, about $1\times10^{-5}$ M, about $1\times10^{-4}$ M, about $1\times10^{-3}$ M, or any intervening final concentration. In treatments comprising one or more agents, the agents can be at different concentrations from each other or at the same concentration.

In particular embodiments, HSPCs are treated (e.g., contacted with one or more agents) 1, 2, 3, 4, 5, 6, 7, 8, 9 or 10 or more times. The HSPCs can be intermittently, episodically, or sequentially contacted with one or more agents within the same vessel (e.g., contacting the population of cells with one drug for a period of time, exchanging the culture medium and/or washing the population of cells, then repeating the cycle with the same or a different combination of pharmaceutical agents for the same predetermined period of time or a different predetermined period of time).

6. Treatment of HSPCs

In one embodiment, the method of preparing the HSPCs comprises treating HSPCs ex vivo with one or more agents capable of increasing CXCR4 gene expression conditions sufficient to increase CXCR4 gene expression at least 30, 40, 50, 60, 70, or 80 fold in the contacted cells compared to non-contacted cells. The HSPCs may be treated with agents disclosed herein after isolation from a subject. In another embodiment, HSPCs are isolated from a subject and expanded prior to treatment with the agents disclosed herein. In one embodiment, the HSPCs are isolated from a subject and cryopreserved prior to treatment with the agents disclosed herein.

In particular embodiments, HSPCs are treated with one or more agents, e.g., a combination of a prostaglandin pathway agonist and a glucocorticoid, in an amount effective and for a time sufficient (i.e., under conditions sufficient) to increase CXCR4 gene expression at least 30, 40, 50, 60, 70, or 80 fold in the contacted cells compared to non-contacted cells.

In various embodiments, sufficient temperature conditions include incubation of the HSPCs with the one or more agents at a physiologically relevant temperature, such as a temperature range of about 22° C. to about 39° C. (about room temperature to about body temperature), including but not limited to temperatures of about 22° C., 23° C., 24° C., 25° C., 26° C., 27° C., 28° C., 29° C., 30° C., 31° C., 32° C., 33° C., 34° C., 35° C., 36° C., 37° C., 38° C., and 39° C. In a particular embodiment, the sufficient temperature condition is between about 35° C. and 39° C. In one embodiment, the sufficient temperature condition is about 37° C.

In various embodiments, a sufficient concentration of an agent is a final concentration of about 10 nM to about 100 µM, about 100 nM, about 500 nM, about 1 µM, about 10 µM, about 20 µM, about 30 µM, about 40 µM, about 50 µM, about 60 µM, about 70 µM, about 80 µM, about 90 M, about 100 µM, about 110 µM, or about 120 µM, or any other intervening concentration of the agent (e.g., 0.1 µM, 1 µM, 5 µM, 10 µM, 20 µM, 50 µM, 100 µM). In a particular embodiment, the sufficient concentration of each agent is a final concentration of about 10 µM to about 25 µM. In one embodiment, the sufficient concentration of an agent is a final concentration of about 10 µM.

In various embodiments, the sufficient time period for treating the HSPCs with one or more agents is an incubation period of about 60 minutes to about 24 hours, about 60 minutes to about twelve hours, about 60 minutes to about 6 hours, about 2 hours to about 6 hours, about 2 hours to about 4 hours, and including, but not limited to, treatment for a duration of about 60 minutes, about 70 minutes, about 80 minutes, about 90 minutes, about 100 minutes, about 110 minutes, about 2 hours, about 2.5 hours, about 3 hours, about 3.5 hours or about 4 hours or any other intervening duration. In a particular embodiment, the sufficient incubation period is about 2 hours to about 4 hours. In one embodiment, the sufficient incubation period for treating the HSPCs is about four hours.

In particular embodiments, conditions sufficient to increase CXCR4 gene expression at least 30, 40, 50, 60, 70, or 80 fold in the contacted cells compared to non-contacted cells comprises treating HSPCs ex vivo at a temperature range of about 22° C. to about 39° C.; at a final concentration of about 10 µM to about 25 µM of a prostaglandin pathway agonist, and about 10 µM to about 25 µM of a glucocorticoid; and incubation with the agents for about 1 hour to about 4 hours, for about 2 hours to about 3 hours, for about 2 hours to about 4 hours, or for about 3 hours to about 4 hours.

In particular embodiments, conditions sufficient to increase CXCR4 gene expression at least 30, 40, 50, 60, 70, or 80 fold in the contacted cells compared to non-contacted cells comprises treating HSPCs ex vivo at a temperature range of about 22° C. to about 39° C.; at a final concentration of about 10 µM to about 25 µM of $PGE_2$ or $dmPGE_2$, and about 10 µM to about 25 µM of a glucocorticoid; and incubation with the agents for about 1 hour to about 4 hours, for about 2 hours to about 3 hours, for about 2 hours to about 4 hours, or for about 3 hours to about 4 hours.

In particular embodiments, conditions sufficient to increase CXCR4 gene expression at least 30, 40, 50, 60, 70, or 80 fold in the contacted cells compared to non-contacted cells comprises treating HSPCs ex vivo at a temperature range of about 22° C. to about 39° C.; at a final concentration of about 10 µM to about 25 µM of $PGE_2$ or $dmPGE_2$, and about 10 µM to about 25 µM of a compound selected from the group consisting of medrysone, hydrocortisone, alclometasone, dexamethasone, methylprednisolone, or triamcinolone; and incubation with the agents (compounds) for about 1 hour to about 4 hours, for about 2 hours to about 3 hours, for about 2 hours to about 4 hours, or for about 3 hours to about 4 hours.

In particular embodiments, conditions sufficient to increase CXCR4 gene expression at least 30, 40, 50, 60, 70, or 80 fold in the contacted cells compared to non-contacted cells comprises treating HSPCs ex vivo at a temperature range of about 22° C. to about 39° C.; at a final concentration of about 10 µM to about 25 µM of a prostaglandin pathway agonist, and about 10 µM to about 25 µM of medrysone; and incubation with the agents for about 1 hour to about 4 hours, for about 2 hours to about 3 hours, for about 2 hours to about 4 hours, or for about 3 hours to about 4 hours.

In another embodiment, conditions sufficient to increase CXCR4 gene expression at least 30, 40, 50, 60, 70, or 80 fold in the contacted cells compared to non-contacted cells comprises treating HSPCs ex vivo include, incubation at a temperature of about 37° C. (about body temperature); a final concentration of about 10 µM $PGE_2$ or 16,16-dimethyl $PGE_2$, in combination with a final concentration of about 10 µM of a compound selected from the group consisting of medrysone, hydrocortisone, alclometasone, dexamethasone, methylprednisolone, or triamcinolone; and incubation for about four hours.

In another embodiment, conditions sufficient to increase CXCR4 gene expression at least 30, 40, 50, 60, 70, or 80 fold in the contacted cells compared to non-contacted cells comprises treating HSPCs ex vivo include, incubation at a temperature of about 37° C. (about body temperature); a final concentration of about 10 µM $PGE_2$ or 16,16-dimethyl $PGE_2$, in combination with a final concentration of about 10 µM of medrysone; and incubation for about four hours.

In particular embodiments, HSPCs are treated (e.g., contacted with one or more agents) 1, 2, 3, 4, 5, 6, 7, 8, 9 or 10 or more times. Cells can be intermittently, episodically, or sequentially contacted with one or more agents within the same vessel (e.g., contacting the HSPCs with one agent for a period of time, exchanging the culture medium and/or washing the population of cells, then repeating the cycle with the same or a different combination of agents for the same predetermined period of time or a different predetermined period of time).

E. Therapeutic Uses of the Enhanced Stem Cells

HSPCs described herein have increased CXCR4 gene and protein expression, and also exhibit enhanced therapeutic properties compared to untreated cells. In particular, the HSPCs of the invention exhibit increased homing to bone marrow, ischemic tissue sites, and ischemia-damaged tissue, and also exhibit increased engraftment. The HSPCs of the invention are thus useful for treating subjects in need of treatment with increased homing and/or engraftment of HSPCs to the bone marrow or sites of ischemia or ischemia-damaged tissue. In certain embodiments, the HSPCs are also useful for improving hematopoietic stem cell transplants and in treating ischemia or ischemia-damaged tissue, and in reducing further damage to ischemic tissue and/or repairing damage to ischemic tissue through cell recruitment, improving vascularization in ischemic tissue, improving tissue regeneration at sites of ischemia, decreasing ischemic tissue necrosis or apoptosis, and/or increasing cell survival at sites of ischemia. In particular embodiments, the HPSCs are useful to subjects in need of hematopoietic reconstitution, such as subjects that have undergone or are scheduled to undergo myeloablative therapy.

As used herein, the term "engraft" refers to the ability of a cell to integrate into a location, such as a tissue, and persist in the particular location over time. Cells may engraft in the bone marrow, for instance, or in another location such as a site of injured or ischemic tissue. "Homing" refers to the ability of HSPCs to localize, i.e., travel, to a particular area or tissue. Homing may include localization of administered HSPCs to the bone marrow or to another location such as a site of injured or ischemic tissue. In one embodiment, cells use a chemoattractant mechanism to home to a particular tissue: cells having increased expression of CXCR4 have improved homing to ischemic tissues secreting stromal cell derived factor 1 (SDF1), the cognate ligand of CXCR4.

A "subject," as used herein, includes any human that exhibits a symptom that can be treated with a cell-based composition of the invention, or can be treated with HSPCs having increased CXCR4 gene expression.

In various other embodiments, the invention provides methods of treating a subject in need thereof that comprise identifying a subject in need, and administering to the subject HSPCs contacted with one or more agents that increase CXCR4 gene expression in the cells, including a combination of a prostaglandin pathway agonist and a glucocorticoid, under conditions sufficient to increase CXCR4 gene expression in the cells at least 30, 40, 50, 60, 70, or 80 fold compared to the level of CXCR4 gene expression in non-contacted cells, thereby treating the subject in need.

As used herein, the terms "treatment," "treating," and the like, refer to obtaining a desired pharmacologic and/or physiologic effect, including without limitation achieving an improvement or elimination of symptoms of a disease. The effect may be prophylactic in terms of completely or partially preventing a disease or symptom thereof and/or may be therapeutic in terms of achieving an improvement or elimination of symptoms, or providing a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; (c) relieving the disease, e.g., causing regression of the disease, e.g., to completely or partially eliminate symptoms of the disease; and (d) restoring the individual to a pre-disease state, e.g., reconstituting the hematopoietic system.

"Treatment" or "treating," as used herein, includes any desirable effect on the symptoms or pathology of a disease or pathological condition, and may include even minimal reductions in one or more measurable markers of the disease or condition being treated. "Treatment" does not necessarily indicate, or require, complete eradication or cure of the disease or condition, or associated symptoms thereof.

1. Stem Cell Transplant Methods

"Subjects in need" of hematopoietic reconstitution, reconstitution of the hematopoietic system, and an increased number of HSPCs include, but are not limited to subjects that have or that have been diagnosed with various types of leukemias, anemias, lymphomas, myelomas, immune deficiency disorders, and solid tumors as discussed elsewhere herein. A "subject" also includes a human who is a candidate for stem cell transplant or bone marrow transplantation, such as during the course of treatment for a malignant disease or a component of gene therapy. In particular embodiments, a subject receives genetically modified HSPCs as a cell-based gene therapy. Subjects may also include individuals or animals that donate stem cells or bone marrow for allogeneic transplantation. In certain embodiments, a subject may have undergone myeloablative irradiation therapy or chemotherapy, or may have experienced an acute radiation or chemical insult resulting in myeloablation. In certain embodiments, a subject may have undergone irradiation therapy or chemotherapy, such as during various cancer treatments. Typical subjects include animals that exhibit aberrant amounts (lower or higher amounts than a "normal" or "healthy" subject) of one or more physiological activities that can be modulated by an agent or a stem cell or marrow transplant.

Subjects in need of hematopoietic reconstitution include subjects undergoing chemotherapy or radiation therapy for cancer, as well as subjects suffering from (e.g., afflicted with) non malignant blood disorders, particularly immunodeficiencies (e.g. SCID, Fanconi's anemia, severe aplastic anemia, or congenital hemoglobinopathies, or metabolic storage diseases, such as Hurler's disease, Hunter's disease, mannosidosis, among others) or cancer, particularly hematological malignancies, such as acute leukemia, chronic leukemia (myeloid or lymphoid), lymphoma (Hodgkin's or non-Hodgkin's), multiple myeloma, myelodysplastic syndrome, or non-hematological cancers such as solid tumors (including breast cancer, ovarian cancer, brain cancer, prostate cancer, lung cancer, colon cancer, skin cancer, liver cancer, or pancreatic cancer).

Subjects may also include subjects suffering from aplastic anemia, an immune disorder (severe combined immune deficiency syndrome or lupus), myelodysplasia, thalassemaia, sickle-cell disease or Wiskott-Aldrich syndrome. In some embodiments, the subject suffers from a disorder that is the result of an undesired side effect or complication of another primary treatment, such as radiation therapy, chemotherapy, or treatment with a bone marrow suppressive drug, such as zidovadine, chloramphenical or gangciclovir. Such disorders include neutropenias, anemias, thrombocytopenia, and immune dysfunction.

Other subjects may have disorders caused by an infection (e.g., viral infection, bacterial infection or fungal infection) which causes damage to stem or progenitor cells of the bone marrow.

In addition, subject suffering from the following conditions can also benefit from treatment using HSPCs of the invention: lymphocytopenia, lymphorrhea, lymphostasis, erythrocytopenia, erthrodegenerative disorders, erythroblastopenia, leukoerythroblastosis; erythroclasis, thalassemia, myelofibrosis, thrombocytopenia, disseminated intravascular coagulation (DIC), immune (autoimmune) thrombocytopenic purpura (ITP), HIV inducted ITP, myelodysplasia; thrombocytotic disease, thrombocytosis, congenital neutropenias (such as Kostmann's syndrome and Schwachman-Diamond syndrome), neoplastic associated-neutropenias, childhood and adult cyclic neutropaenia; post-infective neutropaenia; myelodysplastic syndrome; neutropaenia associated with chemotherapy and radiotherapy; chronic granulomatous disease; mucopolysaccharidoses; Diamond Blackfan; Sickle cell disease; or Beta thalassemia major.

In a particular embodiment, the subject is a bone marrow donor who has donated bone marrow, is a bone marrow donor who has yet to donate bone marrow, is a bone marrow donor transplant recipient, has hematopoietic progenitor cells under environmental stress, has anemia, has a reduced level of immune cell function compared to a normal subject, or has an immune system deficiency.

In a certain embodiment, the subject has myeloma, non-Hodgkin's lymphoma, Hodgkin's lymphoma, chronic myeloid leukemia, chronic myelogenous leukemia, chronic granulocytic leukemia, acute lymphoblastic leukemia, acute nonlymphoblastic leukemia, or pre-leukemia.

In particular embodiments, the subject is in need of gene therapy, such as, for example, a hemoglobinopathy. As used herein, the term "hemoglobinopathy" or "hemoglobinopathic condition" includes any disorder involving the presence of an abnormal hemoglobin molecule in the blood. Examples of hemoglobinopathies included, but are not limited to, hemoglobin C disease, hemoglobin sickle cell disease (SCD), sickle cell anemia, and thalassemias. Also included are hemoglobinopathies in which a combination of abnormal hemoglobins are present in the blood (e.g., sickle cell/Hb-C disease).

The term "sickle cell anemia" or "sickle cell disease" is defined herein to include any symptomatic anemic condition which results from sickling of red blood cells. Manifestations of sickle cell disease include: anemia; pain; and/or organ dysfunction, such as renal failure, retinopathy, acute-chest syndrome, ischemia, priapism and stroke. As used herein the term "sickle cell disease" refers to a variety of clinical problems attendant upon sickle cell anemia, especially in those subjects who are homozygotes for the sickle cell substitution in HbS. Among the constitutional manifestations referred to herein by use of the term of sickle cell disease are delay of growth and development, an increased tendency to develop serious infections, particularly due to pneumococcus, marked impairment of splenic function, preventing effective clearance of circulating bacteria, with recurrent infarcts and eventual destruction of splenic tissue. Also included in the term "sickle cell disease" are acute episodes of musculoskeletal pain, which affect primarily the lumbar spine, abdomen, and femoral shaft, and which are similar in mechanism and in severity to the bends. In adults, such attacks commonly manifest as mild or moderate bouts of short duration every few weeks or months interspersed with agonizing attacks lasting 5 to 7 days that strike on average about once a year. Among events known to trigger such crises are acidosis, hypoxia and dehydration, all of which potentiate intracellular polymerization of HbS (J. H. Jandl, Blood: Textbook of Hematology, 2nd Ed., Little, Brown and Company, Boston, 1996, pages 544-545). As used herein, the term "thalassemia" encompasses hereditary anemias that occur due to mutations affecting the synthesis of hemoglobin. Thus, the term includes any symptomatic anemia resulting from thalassemic conditions such as severe or β-thalassemia, thalassemia major, thalassemia intermedia, α-thalassemias such as hemoglobin H disease.

As used herein, "thalassemia" refers to a hereditary disorder characterized by defective production of hemoglobin. Examples of thalassemias include β and a thalassemia, β thalassemias are caused by a mutation in the beta globin chain, and can occur in a major or minor form. In the major form of β thalassemia, children are normal at birth, but develop anemia during the first year of life. The mild form of β thalassemia produces small red blood cells a thalassemias are caused by deletion of a gene or genes from the globin chain. As used herein, "antisickling proteins" include proteins which prevent or reverse the pathological events leading to sickling of erythrocytes in sickle cell conditions. In one embodiment of the invention, the transduced cells of the invention are used to deliver antisickling proteins to a subject with a hemoglobinopathic condition. Antisickling proteins also include mutated β-globin genes comprising antisickling amino acid residues.

In various embodiments, the invention provides, in part, methods for obtaining and preparing HSPCs for a hematopoietic stem progenitor cell transplant, comprising contacting HSPCs with one or more agents that increase CXCR4 gene expression in the HSPCs, including a combination of a prostaglandin pathway agonist and a glucocorticoid, under conditions sufficient to increase CXCR4 gene expression in the HSPCs at least 30, 40, 50, 60, 70, or 80 fold compared to the level of CXCR4 gene expression in non-contacted cells.

In various other embodiments, the invention provides, in part, a method of increasing hematopoietic stem and progenitor cell homing in a subject comprising contacting HSPCs with one or more agents that increase CXCR4 gene expression in the HSPCs, including a combination of a prostaglandin pathway agonist and a glucocorticoid, under conditions sufficient to increase CXCR4 gene expression in the HSPCs at least 30, 40, 50, 60, 70, or 80 fold compared to the level of CXCR4 gene expression in non-contacted cells, In particular embodiments, the treated HSPCs are washed to substantially remove the agents, and subsequently administered to a subject in need of an increase in hematopoietic stem cell homing.

The invention contemplates, in part, methods to increase stem cell engraftment in a subject in need thereof comprising contacting a population of cells that comprises HSPCs (e.g., bone marrow cells, peripheral blood cells, and/or umbilical cord blood cells) with one or more agents that increase CXCR4 gene expression in the HSPCs, including a combination of a prostaglandin pathway agonist and a glucocorticoid, under conditions sufficient to increase CXCR4 gene expression in the HSPCs at least 30, 40, 50, 60, 70, or 80 fold compared to the level of CXCR4 gene expression in non-contacted cells, and administering the enhanced HSPCs to the subject.

In a particular embodiment, the invention provides a method of treating a subject in need of hematopoietic reconstitution or reconstitution of the hematopoietic system comprising identifying a subject in need of hematopoietic reconstitution, and administering to the subject an amount of HSPCs contacted with one or more agents that increase CXCR4 gene expression in the HSPCs, including a combination of a prostaglandin pathway agonist and a glucocorticoid, under conditions sufficient to increase CXCR4 gene expression in the HSPCs at least 30, 40, 50, 60, 70, or 80 fold compared to the level of CXCR4 gene expression in non-contacted cells, thereby treating the subject in need of hematopoietic reconstitution.

In another particular embodiment, the invention provides a method of treating a subject in need of hematopoietic reconstitution, reconstitution of the hematopoietic system, or an increased number of HSPCs, comprising identifying a subject in need of hematopoietic reconstitution, and administering to the subject an amount of HSPCs contacted with one or more agents that increase CXCR4 gene expression in the HSPCs, including a combination of a prostaglandin pathway agonist and a glucocorticoid, under conditions sufficient to increase CXCR4 gene expression in the HSPCs at least 30, 40, 50, 60, 70, or 80 fold compared to the level of CXCR4 gene expression in non-contacted cells, thereby treating the subject in need of hematopoietic reconstitution.

In another particular embodiment, the invention contemplates, a method of treating a subject in need of a hematopoietic stem cell transplant that comprises: selecting the subject in need of a hematopoietic stem cell transplant and administering to a subject HSPCs that have been contacted with one or more agents that increase CXCR4 gene expression in the cells, including a combination of a prostaglandin pathway agonist and a glucocorticoid, under conditions sufficient to increase CXCR4 gene expression in the HSPCs at least 30, 40, 50, 60, 70, or 80 fold compared to the level of CXCR4 gene expression in non-contacted cells. In particular embodiments, the subject is in need of hematopoietic reconstitution.

In particular illustrative embodiments of the methods described herein for increasing homing or engraftment of HSPCs, or for treating subjects in need of hematopoietic reconstitution, reconstitution of the hematopoietic system, or for performing a hematopoietic stem cell transplant, the HSPCs are treated with a combination of one or more agents that includes (i) $PGE_2$, $dmPGE_2$, 15(S)-15-methyl $PGE_2$, 20-ethyl $PGE_2$, or 8-iso-16-cyclohexyl-tetranor $PGE_2$ and (ii) a glucocorticoid. In more particular embodiments, the combination includes (i) $PGE_2$ or 16,16-dimethyl $PGE_2$ and (ii) medrysone, hydrocortisone, dexamethasone, methylprednisolone, triamcinolone, or alclometasone. In more particular embodiments, the combination includes (i) $PGE_2$ or 16,16-dimethyl $PGE_2$ and (ii) medrysone.

Without wishing to be bound to any particular theory, the present invention contemplates, in part, that one of the advantages of using the enhanced HSPCs of the invention in stem cell transplants is that fewer HSPCs can be used in a transplant because the enhanced HSPCs have, for example, increased engraftment potential, improved homing, and increased capacity for in vivo expansion compared to untreated HSPCs.

2. Ischemic Tissue Treatment Methods

The invention provides methods of cell-based therapy for treating ischemic tissue or treating or ameliorating one or more symptoms associated with tissue ischemia, including, but not limited to, impaired, or loss of, organ function (including without limitation impairments or loss of brain, kidney, or heart function), cramping, claudication, numbness, tingling, weakness, pain, reduced wound healing, inflammation, skin discoloration, and gangrene.

Ischemic tissue may be treated by increased homing of stem cells to sites of ischemic tissue damage, increased recruitment of endogenous stem cells and endothelial progenitor cells at the ischemic tissue site, increased vascularization at the ischemic tissue site, reducing ischemic tissue necrosis or programmed cell death, or increasing cell survival at the ischemic tissue site. Accordingly, the invention contemplates, in part, cells having these therapeutic properties would be useful in treating ischemic tissue or a tissue damaged by ischemia or treating or ameliorating at least one symptom associated with an ischemic tissue.

As used herein, the terms "ischemia," "ischemic condition," or "ischemic event" mean any decrease or stoppage in the blood supply to any cell, tissue, organ, or body part caused by any constriction, damage, or obstruction of the vasculature. Ischemia sometimes results from vasoconstriction or thrombosis or embolism. Ischemia can lead to direct ischemic injury, tissue damage due to cell death caused by reduced supply of oxygen (hypoxia, anoxia), glucose, and nutrients. "Hypoxia" or a "hypoxic condition" intends a condition under which a cell, organ or tissue receives an inadequate supply of oxygen. "Anoxia" refers to a virtually complete absence of oxygen in the organ or tissue, which, if prolonged, may result in death of the cell, organ or tissue.

"Symptoms associated with ischemia," "symptoms resulting from ischemia," or "symptoms caused by ischemia" refers to symptoms that include, but are not limited to: impaired, or loss of, organ function (including without limitation impairments or loss of brain, kidney, or heart function), cramping, claudication, numbness, tingling, weakness, pain, reduced wound healing, inflammation, skin discoloration, and gangrene.

"Ischemic tissue injury," "ischemic tissue damage," "tissue damage due to ischemia," "tissue damage associated with ischemia," "tissue damage as a result of ischemia," "tissue damaged caused by ischemia," and "ischemic-damaged tissue" refers to morphological, physiological, and/or molecular damage to an organ or tissue or cell as a result of a period of ischemia.

In one embodiment, the subject exhibits at least one symptom of an ischemic tissue or tissue damaged by ischemia. In particular embodiments, the subject is a human who is has or who is at risk of having an ischemic tissue or tissue damaged by ischemia, e.g., a subject that has diabetes, peripheral vascular disease, thromboangiitis obliterans, vasculitis, cardiovascular disease, coronary artery disease or heart failure, or cerebrovascular disease, cardiovascular disease, or cerebrovascular disease.

The invention also provides, in particular embodiments, a method of treating ischemic tissue or a tissue damaged by ischemia, comprising administering to a patient in need of such treatment HSPCs contacted with one or more agents that increase CXCR4 gene expression in the cells, including a combination of a prostaglandin pathway agonist and a glucocorticoid, under conditions sufficient to increase CXCR4 gene expression in the cells at least 30, 40, 50, 60, 70, or 80 fold compared to the level of CXCR4 gene expression in non-contacted cells.

In one embodiment, the cells provide therapy to the subject by increased homing of stem cells to sites of ischemic tissue damage, increased recruitment of endogenous stem cells and endothelial progenitor cells at the ischemic tissue site, increased stimulation of vascularization at the ischemic tissue site, reducing ischemic tissue necrosis or programmed cell death, or increasing cell survival at the ischemic tissue site.

In various other embodiments, the invention provides a method of treating or ameliorating an ischemic tissue injury comprising administering to a subject a therapeutically effective amount of a composition comprising HSPCs contacted with one or more agents that increase CXCR4 gene expression in the cells, including a combination of a prostaglandin pathway agonist and a glucocorticoid, under conditions sufficient to increase CXCR4 gene expression in the cells at least 30, 40, 50, 60, 70, or 80 fold compared to the level of CXCR4 gene expression in non-contacted cells.

In various other embodiments, the invention provides a method of treating or ameliorating a symptom associated with an ischemic tissue injury comprising administering to a subject HSPCs contacted with one or more agents that increase CXCR4 gene expression in the cells, including a combination of a prostaglandin pathway agonist and a glucocorticoid, under conditions sufficient to increase CXCR4 gene expression in the cells at least 30, 40, 50, 60, 70, or 80 fold compared to the level of CXCR4 gene expression in non-contacted cells.

Illustrative examples of tissues that are suitable for treatment with the compositions of the present invention include, mesodermal tissue, endodermal tissue, or ectodermal tissue. Other tissues suitable for treatment with the compositions of the present invention include, but are not limited to, skin tissue, skeletal muscle tissue, cardiac muscle tissue, smooth muscle tissue, cartilage tissue, tendon tissue, bone tissue, brain tissue, spinal cord tissue, retinal tissue, corneal tissue, lung tissue, liver tissue, kidney tissue, pancreatic tissue, ovarian tissue, testicular tissue, intestinal tissue, stomach tissue, and bladder tissue.

In particular embodiments, any tissue that has a compromised blood supply and is ischemic or at risk for becoming ischemic may be treated using the methods of the invention.

Illustrative examples of genetic disorders, syndromic conditions, traumatic injuries, chronic conditions, medical interventions, or other conditions that cause or are associated with ischemia, or increase the risk of ischemia in a subject, or cause a subject to exhibit more or more symptoms of ischemia, and thus, suitable for treatment or amelioration using the methods of the present invention, include, but are not limited to, acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, frostbite, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

Other illustrative examples of genetic disorders, syndromic conditions, traumatic injuries, chronic conditions, medical interventions, or other conditions that cause or are associated with ischemia, or increase the risk of ischemia in a subject, or cause a subject to exhibit more or more symptoms of ischemia suitable for treatment or amelioration using the methods of the present invention, include, ischemia resulting from surgery, chemotherapy, radiation therapy, or cell, tissue, or organ transplant or graft.

In various embodiments, the methods of the invention are suitable for treating cerebrovascular ischemia, myocardial ischemia, limb ischemia (CLI), myocardial ischemia (especially chronic myocardial ischemia), ischemic cardiomyopathy, cerebrovascular ischemia, renal ischemia, pulmonary ischemia, intestinal ischemia, and the like.

In various embodiments, the invention contemplates that the therapeutic cell compositions disclosed herein can be used to treat an ischemic tissue in which it is desirable to increase the blood flow, oxygen supply, glucose supply, or supply of nutrients to the tissue.

3. Expanded HSPCs

The invention further contemplates that the enhanced HSPCs provided by the invention are not expanded ex vivo or in vitro prior to administration to a subject. In particular embodiments, an unexpanded population of HSPCs is obtained, the population of HSPCs is treated ex vivo in accordance with the protocol provided herein to obtain enhanced HSPCS, the enhanced HSPCs may be washed to remove the treatment agent(s), and the enhanced HSPCs are administered to a patient without expansion of the HSPC population ex vivo. In some embodiments, HSPCs are obtained from a donor, including cord blood, and are not expanded prior to or after treatment of the HSPCs, or at any time prior to administration of the therapeutic composition to a patient.

In one embodiment, an unexpanded population of HSPCs is treated and is administered to a patient prior to any substantial ex vivo cell division of the HSPCs in the population, or prior to the time required for any substantial cell division ex vivo. In other embodiments, an unexpanded population of HSPCs is treated and is administered to a patient prior to any substantial ex vivo mitosis of the HSPCs in the population, or prior to the time required for any substantial mitosis ex vivo. In some embodiments, an unexpanded population of HSPCs is treated and is administered to a patient prior to the doubling time of the HSPCs in the population. In some embodiments, an unexpanded population of HSPCs is treated and is administered to a patient within 6, 12, or 24 hours of treatment of the HSPCs. In other embodiments, an unexpanded population of HSPCs is treated and is administered to a patient within 2 hours of treatment of the HSPCs.

In various embodiments, the HSPCs of the invention are not cultured prior to treatment with one or more agents, or combinations of agents, ex vivo or at any time prior to administration to a patient. In some embodiments, the HSPCs are cultured for less than about 24 hours. In other embodiments, the HSPCs are cultured for less than about 12 hours, 10 hours, 8 hours, 6 hours, 4 hours, or two hours.

In other embodiments, the invention provides HSPCs that are expanded prior to treatment of the HSPCs with agents to obtain enhanced HSPCs. HSPCs, whether obtained from cord blood, bone marrow, peripheral blood, Wharton's jelly, placental blood or other source, may be grown or expanded in any suitable, commercially available or custom defined medium, with or without serum, as desired (see, e.g., Hartshorn et al., *Cell Technology for Cell Products*, pages 221-224, R. Smith, Editor; Springer Netherlands, 2007, herein incorporated by reference in its entirety). For instance, in certain embodiments, serum free medium may utilize albumin and/or transferrin, which have been shown to be useful for the growth and expansion of $CD34^+$ cells in serum free medium. Also, cytokines may be included, such as Flt-3 ligand, stem cell factor (SCF), and thrombopoietin (TPO), among others. HSPCs may also be grown in vessels such as bioreactors (see, e.g., Liu et al., *Journal of Biotechnology* 124:592-601, 2006, herein incorporated by reference in its entirety). A suitable medium for ex vivo expansion of HSPCs may also comprise supporting cells, such as stromal cells (e.g., lymphoreticular stromal cells), which can be derived, for instance, from the disaggregation of lymphoid tissue, and which have been show to support the in vitro, ex vivo, and in vivo maintenance, growth, and differentiation of hematopoietic stem and progenitor cells, as well as their progeny.

In various embodiments, the enhanced HSPCs administered to a subject are a heterogeneous population of cells including, whole bone marrow, umbilical cord blood, mobilized peripheral blood, hematopoietic stem cells, hematopoietic progenitor cells, and the progeny of hematopoietic stem and progenitor cells, including granulocytes (e.g., promyelocytes, myelocytes, metamyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages).

4. Administration of HSPCs and Compositions Thereof

In various embodiments, the present invention provides, in part, methods comprising administration of treated HPSCs to a subject in need thereof. Suitable methods for administering populations of cells used in the methods described herein include parenteral administration, including, but not limited to methods of intravascular administration, such as intravenous and intraarterial administration. Additional illustrative methods for administering cells of the invention include intramuscular, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

In one embodiment, a method for increasing homing or engraftment of HSPCs comprises parenteral administration of HSPCs contacted with one or more agents that increase CXCR4 gene expression in the cells, including a combination of a prostaglandin pathway agonist and a glucocorticoid, under conditions sufficient to increase CXCR4 gene expression in the cells at least 30, 40, 50, 60, 70, or 80 fold compared to the level of CXCR4 gene expression in non-contacted cells.

In one embodiment, a method for hematopoietic reconstitution, reconstitution of the hematopoietic system, or for performing a hematopoietic stem cell transplant, comprises parenteral administration of HSPCs contacted with one or more agents that increase CXCR4 gene expression in the cells, including a combination of a prostaglandin pathway agonist and a glucocorticoid, under conditions sufficient to increase CXCR4 gene expression in the cells at least 30, 40, 50, 60, 70, or 80 fold compared to the level of CXCR4 gene expression in non-contacted cells.

In preferred embodiments, the HSPCs are administered or infused to a subject intravenously.

In particular illustrative embodiments of the methods described herein for increasing homing or engraftment of HSPCs, or for treating subjects in need of hematopoietic reconstitution, reconstitution of the hematopoietic system, or for performing a hematopoietic stem cell transplant, comprise intravenously administering or infusing HSPCs treated with a combination of one or more agents that includes (i) $PGE_2$, $dmPGE_2$, 15(S)-15-methyl $PGE_2$, 20-ethyl $PGE_2$, or 8-iso-16-cyclohexyl-tetranor $PGE_2$ and (ii) a glucocorticoid. In more particular embodiments, the methods comprise intravenously administering or infusing HSPCs treated with (i) $PGE_2$ or 16,16-dimethyl $PGE_2$ and (ii) medrysone, hydrocortisone, dexamethasone, methylprednisolone, triamcinolone, or alclometasone. In more particular embodiments, the methods comprise intravenously administering or infusing HSPCs treated with (i) $PGE_2$ or 16,16-dimethyl $PGE_2$ and (ii) medrysone.

In particular embodiment, the composition may be administered to an individual having ischemia, ischemic tissue, or at least one symptom of ischemia. Most preferably, the site of administration is close to or nearest the intended site of activity, i.e., near the site of tissue ischemia. In cases when a subject suffers from global ischemia, a systemic administration, such as intravenous administration, is preferred. Without intending to be bound by mechanism, when the therapeutic compositions are administered, the HSPCs migrate or home to the ischemic tissue in response to chemotactic factors produced due to the injury to effect treatment of ischemic tissue or treatment and amelioration of at least one symptom associated with the ischemic tissue.

The HSPCs can be injected directly into the area of ischemia, or the stem cells may be infused into an artery supplying the area of tissue ischemia. Where the subject has a totally occluded vessel that would normally supply the area of the ischemic tissue, the selected artery for infusion is preferably a vessel that provides collateral flow to the ischemic tissue in the distribution of the totally occluded vessel.

HSPCs and therapeutic compositions of the invention may be inserted into a delivery device which facilitates introduction by injection or implantation into the subjects. Such delivery devices may include tubes, e.g., catheters, for injecting cells and fluids into the body of a recipient subject.

In one embodiment, the tubes additionally have a needle, e.g., a syringe, through which the cells of the invention can be introduced into the subject at a desired location. In a particular embodiment, cells are formulated for administration into a blood vessel via a catheter (where the term "catheter" is intended to include any of the various tube-like systems for delivery of substances to a blood vessel).

In one embodiment, a method for treating an ischemic tissue, or a tissue damaged by ischemia, comprises parenteral administration of HSPCs contacted with one or more agents that increase CXCR4 gene expression in the cells, including a combination of a prostaglandin pathway agonist and a glucocorticoid, under conditions sufficient to increase CXCR4 gene expression in the cells at least 30, 40, 50, 60, 70, or 80 fold compared to the level of CXCR4 gene expression in non-contacted cells.

In one embodiment, a method for treating or ameliorating at least one symptom associated with an ischemic tissue or a tissue damaged by ischemia, comprises parenteral administration of HSPCs contacted with one or more agents that increase CXCR4 gene expression in the cells, including a combination of a prostaglandin pathway agonist and a glucocorticoid, under conditions sufficient to increase CXCR4 gene expression in the cells at least 30, 40, 50, 60, 70, or 80 fold compared to the level of CXCR4 gene expression in non-contacted cells.

In preferred embodiments, the HSPCs are administered intravenously or by direct injection to the ischemic site.

In particular illustrative embodiments of the methods described herein for treating or ameliorating ischemia or at least one symptom of ischemia, comprise intravenously administering or directly injecting HSPCs treated with a combination of one or more agents that includes (i) $PGE_2$, $dmPGE_2$, 15(S)-15-methyl $PGE_2$, 20-ethyl $PGE_2$, or 8-iso-16-cyclohexyl-tetranor $PGE_2$ and (ii) a glucocorticoid. In more particular embodiments, the methods comprise intravenously administering or infusing HSPCs treated with (i) $PGE_2$ or 16,16-dimethyl $PGE_2$ and (ii) medrysone, hydrocortisone, dexamethasone, methylprednisolone, triamcinolone, or alclometasone. In more particular embodiments, the methods comprise intravenously administering or infusing HSPCs treated with (i) $PGE_2$ or 16,16-dimethyl $PGE_2$ and (ii) medrysone.

In particular embodiments, the composition may be administered topically to a site of ischemic tissue damage, such as, for example, the surface of a wound, e.g., a non-healing wound, an ulcer, a burn, or frostbite.

The compositions of the invention may be specially formulated for administration in solid or liquid form, including those adapted for the following: (1) parenteral administration, for example, by subcutaneous, intramuscular, intravenous or epidural injection as, for example, a sterile solution or suspension, or sustained-release formulation as part of a cell grafts, biocompatible scaffolds, etc. In various embodiments, a biocompatible scaffold or graft is provided to promote repair, replacement, and/or regeneration of a damaged, injured, or diseased tissue or organ, e.g., an ischemic tissue.

In certain illustrative embodiments, a method for treating a subject in need of the HPSCs of the invention comprises providing an biocompatible scaffold or cell graft comprising HPSCs of the invention. As used herein, the term "biocompatible scaffold" or "cell graft" refers to a biocompatible natural and/or synthetic structure comprising one or more cell-based compositions, cells, tissues, polymers, polynucleotides, lattices, and/or matrices that is injected, applied to the surface of, or engrafted within a patient or subject that is suitable for directing or attracting a cell-based composition to repair, regenerate, or replace a cell, tissue or organ in vivo.

In particular illustrative embodiments, an implant comprises a biocompatible matrix that can be molded into any suitable form and has especially important roles to prepare tissues in a three-dimensional shape having a certain depth or height or a flat sheet-like shape for application to dermal wounds. Biomaterial science is an established and evolving field (Takayama et al., Principles of Tissue Engineering, Second Edition, edit Lanza R P, Langer R, Vacanti J., Academic Press, San Diego, 2000, pg 209-218; Saltmann et al., Principles of Tissue Engineering, Second Edition, edit Lanza R P, Langer R, Vacanti J., Academic Press, San Diego, 2000, p 221-236; Hubbell et al, Principles of Tissue Engineering, Second Edition, edit Lanza R P, Langer R, Vacanti J., Academic Press, San Diego, 2000, p 237-250; Thomson et al, Principles of Tissue Engineering, Second Edition, edit Lanza R P, Langer R, Vacanti J., Academic Press, San Diego, 2000, p 251-262; Pachence et al, Principles of Tissue Engineering, Second Edition, edit Lanza R P, Langer R, Vacanti J., Academic Press, San Diego, 2000, p 263-278).

Chemists have developed methods to synthesize biocompatible scaffold comprising polymers to direct and modulate cell growth in vitro, ex vivo, and in vivo. The physical properties of the polymers can be modulated to create solid and liquid matrices of specific strengths and viscosities. Some polymers are stable in vivo and will remain in a patient's body for up to 1, 2, 3, 4, 5, 10, 15 or more years. Other polymers are also biodegradable, resorbing at a fixed rate over time to allow replacement by newly synthesized extracellular matrix proteins. Resorption can occur within days to weeks or months following implantation (Pachence et al., *Principles of Tissue Engineering*, Second Edition, edit Lanza R P, Langer R, Vacanti J., Academic Press, San Diego, 2000, p 263-278).

In other illustrative embodiments, a biocompatible scaffold comprises a bioabsorbable material. A porous carrier is preferably made of one component or a combination of multiple components selected from the group consisting of collagen, collagen derivatives, hyaluronic acid, hyaluronates, chitosan, chitosan derivatives, polyrotaxane, polyrotaxane derivatives, chitin, chitin derivatives, gelatin, fibronectin, heparin, laminin, and calcium alginate; wherein a support member is made of one component or a combination of multiple components selected from the group consisting of polylactic acid, polyglycolic acid, polycaprolactone, polylactic acid-polyglycolic acid copolymer, polylactic acid-polycaprolactone copolymer, and polyglycolic acid-polycaprolactone copolymer (see, for example, U.S. Pat. No. 5,077,049 and U.S. Pat. No. 5,42,033, and U.S. Patent Application Publication No. 2006/0121085, of which the polymer formulations and methods of making the same of each patent and application is incorporated herein in its entirety).

In particular illustrative embodiments of the invention, the biocompatible scaffold or cell graft comprises a viscous, biocompatible liquid material. The biocompatible liquid is capable of gelling at body temperature and is selected from the group consisting of alginate, collagen, fibrin, hyaline, or plasma. The viscous, biocompatible liquid material can also be combined with a malleable, three dimensional matrix capable of filling an irregular tissue defect. The matrix is a material including, but not limited to, polyglycolic-polylactic acid, poly-glycolic acid, poly-lactic acid, or suture-like material.

In further illustrative embodiments, biocompatible scaffolds or cell grafts comprising matrices can be molded into desired shapes (e.g., two-dimensional or three-dimensional structures) conducive to or facilitating cell, tissue, and/or organ development. The implant can be formed from polymeric material, having fibers such as a mesh or sponge. Such a structure provides sufficient area on which the cells can grow and proliferate. Desirably, the matrices of the scaffolds or cell grafts are biodegradable over time, so that they will be absorbed into the animal matter as it develops. Suitable polymers can be homopolymers or heteropolymers and can be formed from monomers including, but not limited to, glycolic acid, lactic acid, propyl fumarate, caprolactone, and the like. Other suitable polymeric material can include a protein, polysaccharide, polyhydroxy acid, polyorthoester, polyanhydride, polyphosphozene, or a synthetic polymer, particularly a biodegradable polymer, or any combination thereof.

Sheet-like scaffolds and grafts provide reparative, replacement, and/or regenerative therapy for dermal tissues, membranes for tooth root coverage procedures, membranous tissues (e.g., dura mater), flat bones (e.g., skull, breastbone) and the like. Tubular implants and grafts provide reparative, replacement, and/or regenerative therapy for arteries, veins, ureters, urethras, nerves, long bones (e.g., femur, fibula, tibia, humerus, radius, ulna, metacarpals, metatarsals, etc.) and the like. Other three dimensional implants and grafts provide reparative, replacement, and/or regenerative therapy for organ transplants (e.g., liver, lung, skin, heart, pancreas, etc.), bone remodeling or mending of all types of bones, dental implants, or for muscle, tendon, ligament, and cartilage grafts.

In one embodiment, a method for treating or ameliorating at least one symptom associated with an ischemic tissue or a tissue damaged by ischemia, comprises direct administration, to an ischemic tissue, of a biocompatible scaffold or cell graft comprising HSPCs contacted with one or more agents that increase CXCR4 gene expression in the cells, including a combination of a prostaglandin pathway agonist and a glucocorticoid, under conditions sufficient to increase CXCR4 gene expression in the cells at least 30, 40, 50, 60, 70, or 80 fold compared to the level of CXCR4 gene expression in non-contacted cells.

In particular illustrative embodiments of the methods described herein for treating or ameliorating at least one symptom associated with an ischemic tissue or a tissue damaged by ischemia, comprise direct administration, to an ischemic tissue, of a biocompatible scaffold or cell graft comprising HSPCs treated with a combination of one or more agents that includes (i) $PGE_2$, $dmPGE_2$, 15(S)-15-methyl $PGE_2$, 20-ethyl $PGE_2$, or 8-iso-16-cyclohexyl-tetranor $PGE_2$ and (ii) a glucocorticoid. In more particular embodiments, the methods comprises direct administration, to an ischemic tissue, of a biocompatible scaffold or cell graft comprising HPSCs treated with (i) $PGE_2$ or 16,16-dimethyl $PGE_2$ and (ii) medrysone, hydrocortisone, dexamethasone, methylprednisolone, triamcinolone, or alclometasone. In more particular embodiments, the method comprises direct administration, to an ischemic tissue, of a biocompatible scaffold or cell graft comprising HPSCs treated with (i) $PGE_2$ or 16,16-dimethyl $PGE_2$ and (ii) medrysone.

F. Administration-Ready Compositions of the Invention

The compositions of treated cells of the invention are sterile, and are suitable and ready for administration (i.e., can be administered without any further processing) to human patients. In some embodiments, the therapeutic composition is ready for infusion into a patient. As used herein, the terms "administration-ready," "ready for administration"

or "ready for infusion" refer to a cell based composition of the invention that does not require any further treatment or manipulations prior to transplant or administration to a subject.

The sterile, therapeutically acceptable compositions suitable for administration to a patient may comprise one or more pharmaceutically acceptable carriers (additives) and/or diluents (e.g., pharmaceutically acceptable medium, for example, cell culture medium), or other pharmaceutically acceptable components. Pharmaceutically acceptable carriers and/or diluents are determined in part by the particular composition being administered, as well as by the particular method used to administer the therapeutic composition. Accordingly, there is a wide variety of suitable formulations of therapeutic compositions of the present invention (see, e.g., *Remington's Pharmaceutical Sciences*, 17$^{th}$ ed. 1985)).

In particular embodiments, therapeutic cell compositions comprising stem and/or progenitor cells comprise a pharmaceutically acceptable cell culture medium. A therapeutic composition comprising a cell-based composition of the present invention can be administered separately by enteral or parenteral administration methods or in combination with other suitable compounds to effect the desired treatment goals.

The pharmaceutically acceptable carrier and/or diluent must be of sufficiently high purity and of sufficiently low toxicity to render it suitable for administration to the human subject being treated. It further should maintain or increase the stability of the therapeutic composition. The pharmaceutically acceptable carrier can be liquid or solid and is selected, with the planned manner of administration in mind, to provide for the desired bulk, consistency, etc., when combined with other components of the therapeutic composition of the invention. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions of the present invention include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers envisioned by the invention include, but are not limited to, Dulbecco's phosphate buffered saline (PBS), Ringer's solution, 5% dextrose in water (D5W), normal/physiologic saline (0.9% NaCl).

These pharmaceutically acceptable carriers and/or diluents may be present in amounts sufficient to maintain a pH of the therapeutic composition of between about 3 and about 10. As such, the buffering agent may be as much as about 5% on a weight to weight basis of the total composition. Electrolytes such as, but not limited to, sodium chloride and potassium chloride may also be included in the therapeutic composition.

In one aspect, the pH of the therapeutic composition is in the range from about 4 to about 10. Alternatively, the pH of the therapeutic composition is in the range from about 5 to about 9, from about 6 to about 9, or from about 6.5 to about 8. In another embodiment, the therapeutic composition comprises a buffer having a pH in one of said pH ranges. In another embodiment, the therapeutic composition has a pH of about 7. Alternatively, the therapeutic composition has a pH in a range from about 6.8 to about 7.4. In still another embodiment, the therapeutic composition has a pH of about 7.4.

The sterile composition of the invention may be a sterile solution or suspension in a nontoxic pharmaceutically acceptable medium. The term "suspension" as used herein may refer to non-adherent conditions in which cells are not attached to a solid support. For example, cells maintained in suspension may be stirred and are not adhered to a support, such as a culture dish.

A suspension is a dispersion (mixture) in which a finely-divided species is combined with another species, with the former being so finely divided and mixed that it doesn't rapidly settle out. A suspension may be prepared using a vehicle such as a liquid medium, including a solution. In particular embodiments, the therapeutic composition of the invention is a suspension, where the stem and/or progenitor cells are dispersed within an acceptable liquid medium or solution, e.g., saline or serum-free medium, and are not attached to a solid support. In everyday life, the most common suspensions are those of solids in liquid water. Among the acceptable diluents, e.g., vehicles and solvents, that may be employed are water, Ringer's solution, isotonic sodium chloride (saline) solution, and serum-free cell culture medium. In some embodiments, hypertonic solutions are employed in making suspensions. In addition, sterile, fixed oils are conventionally employed as a solvent or suspending medium. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. In some embodiments, the infusion solution is isotonic to subject tissues. In some embodiments, the infusion solution is hypertonic to subject tissues.

The pharmaceutically acceptable carrier, diluents, and other components comprising the administration-ready therapeutic composition of the invention are derived from U.S. Pharmaceutical grade reagents that will permit the therapeutic composition to be used in clinical regimens. Typically, these finished reagents, including any medium, solution, or other pharmaceutically acceptable carriers and/or diluents, are sterilized in a manner conventional in the art, such as filter sterilized, and are tested for various undesired contaminants, such as mycoplasma, endotoxin, or virus contamination, prior to use. The pharmaceutically acceptable carrier in one embodiment is substantially free of natural proteins of human or animal origin, and suitable for storing the population of cells of the therapeutic composition, including hematopoietic stem and progenitor cells. The therapeutic composition is intended to be administered into a human patient, and thus is substantially free of cell culture components such as bovine serum albumin, horse serum, and fetal bovine serum.

The invention also contemplates, in part, the use of a pharmaceutically acceptable cell culture medium in particular compositions and/or cultures of the present invention. Such compositions are suitable for administration to human subjects. Generally speaking, any medium that supports the maintenance, growth, and/or health of the desired reprogrammed and/or programmed cells of the invention are suitable for use as a pharmaceutical cell culture medium. In particular embodiments, the pharmaceutically acceptable cell culture medium is a serum free medium.

The therapeutic composition may comprise serum-free medium suitable for storing the population of cells comprising the composition. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. Protein-free medium, in contrast, is defined as substantially free of protein.

The serum-free medium employed in the present invention is a formulation suitable for use in human therapeutic protocols and products. One serum-free media is QBSF-60 (Quality Biological, Inc.), as described in U.S. Pat. No. 5,945,337. QBSF-60 isoptimized with U.S. Pharmaceutical grade components and is composed of the basal medium IMDM plus 2 mM L-glutamine, 100 U/ml penicillin, 100 µg/ml streptomycin, human injectable grade serum albumin (4 mg/ml) (Alpha Therapeutic Corporation), partially iron saturated human transferrin (300 µg/ml) (Sigma Chemical Corporation or Bayer Corporation) and human recombinant sodium insulin (0.48 U/ml) (Sigma). Other serum-free media known in the art include, but are not limited to: Life Technologies Catalogue StemPro-34 serum free culture media; Capmany, et al., Short-term, serum-free, static culture of cord blood-derived CD34$^+$ cells: effects of FLT3-L and MIP-1α on in vitro expansion of hematopoietic progenitor cells, Haematologica 84:675-682 (1999); Daley, J P, et al., Ex vivo expansion of human hematopoietic progenitor cells in serum-free StemPro™-34 Medium, *Focus* 18(3):62-67; Life Technologies Catalogue information on AIM V serum free culture media; BioWhittaker Catalogue information on X-VIVO 10 serum free culture media; U.S. Pat. No. 5,397,706 entitled Serum-free basal and culture medium for hematopoietic and leukemia cells; no cell proliferation; Kurtzberg et al., 18:153-4 (2000); Kurtzberg et al., *Exp Hematol* 26(4):288-98 (April 1998).

One having ordinary skill in the art would appreciate that the above example of medium is illustrative and in no way limits the formulation of media suitable for use in the present invention and that there are many such media known and available to those in the art.

In various embodiments, the therapeutic composition of the invention comprises a sterile solution of human serum albumin (HSA), such as 5% HSA, and low molecular weight (LMW) dextran.

The therapeutic composition is substantially free of mycoplasm, endotoxin, and microbial contamination. In particular embodiments, the therapeutic composition contains less than about 10, 5, 4, 3, 2, 1, 0.1, 0.05 µg/ml bovine serum albumin.

By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells.

With respect to mycoplasma and microbial contamination, "substantially free" as used herein means a negative reading for the generally accepted tests known to those skilled in the art. For example, mycoplasma contamination is determined by subculturing a sample of the therapeutic composition in broth medium and distributed over agar plates on day 1, 3, 7, and 14 at 37° C. with appropriate positive and negative controls. The sample appearance is compared microscopically, at 100×, to that of the positive and negative control. Additionally, inoculation of an indicator cell culture is incubated for 3 and 5 days and examined at 600× for the presence of mycoplasmas by epifluorescence microscopy using a DNA-binding fluorochrome. The sample is considered satisfactory if the agar and/or the broth media procedure and the indicator cell culture procedure show no evidence of mycoplasma contamination.

EXAMPLES

Example 1

CXCR4 mRNA Expression Levels in Treated HSPCs

CXCR4 qPCR Using the Fluidigm Platform

Real-time PCR transcript quantitation of gene expression from ex vivo treated human umbilical cord blood derived CD34$^+$ cells (Stem Cell Technologies, Vancouver, BC, Canada) was performed using the BioMark Dynamic Array microfluidics system (Fluidigm Corporation, South San Francisco, Calif., USA).

CD34$^+$ cells derived from cord blood or mobilized peripheral blood were treated in Serum-Free Expansion Medium (SFEM; e.g., StemSpan® from StemCell Technologies, Inc.) for four hours at 37° C., 5% $CO_2$ with 10 uM prostaglandin pathway agonist alone or in combination with 10 uM of a glucocorticoid. Prostaglandin pathway agonists included 16,16-dimethyl $PGE_2$ (dm$PGE_2$), 20-ethyl PGE2 (e$PGE_2$), 15(S)-15-methyl PGE2 (m$PGE_2$), and $PGE_2$. Glucocorticoids included hydrocortisone, dexamethasone, medrysone, alclometasone, or triamcinalone. After treatment, cells were washed with SFEM and centrifuged at 300 g for 10 minutes.

Total RNA was isolated then isolated from treated cells using Pico Pure RNA Isolation Kit (Molecular Devices, Sunnyvale, Calif., USA). Complimentary DNA (cDNA) was reverse transcribed from 50 ng of isolated total RNA using the High-Capacity cDNA Reverse Transcription Kit (Life Technologies Corporation, Carlsbad, Calif., USA).

cDNA was pre-amplified for specific target genes (96) using a 200 nM mixture of 96 gene specific Applied Biosystems TaqMan Assays (see Table 1), including 3 reference control genes (GAPDH, HPRT1, and QARS) using the TaqMan PreAmp Master Mix Kit (Life Technologies) protocol. Specific target amplification (STA) from cDNA was performed using 14 cycles of amplification with the standard cycling conditions using the manufacturer's protocol. For samples, the reaction mix contained 3.0 µL Gene Expression Master Mix (Life Tech.), 0.3 µL Sample Loading Buffer (Fluidigm), 1.5 µL diluted (1:5 sterile nH2O) STA cDNA, and 1.2 µL sterile di$H_2$O for loading into the sample inlets of the 96.96 Dynamic Array (Fluidigm).

Samples were run in replicates, from 5 to 9 wells. The reaction mix contained 2.5 µL Gene Specific Taqman Assays (20×) and 2.5 µL Assay Loading Buffer (Fluidigm) for loading into the assay inlets on the 96.96 Dynamic Array (Fluidigm). 96.96 Dynamic arrays were loaded using a NanoFlex IFC Controller HX (Fluidigm) and real-time reactions were performed using a BioMark Real-Time PCR System (Fluidigm).

Results were analyzed using BioMark Real-Time PCR Analysis software. Average Cts were calculated from the sample replicates and delta-delta Cts (ΔΔCt) were calculated using the mean of 3 reference genes (GAPDH, HPRT1, QARS) against a vehicle only sample. Cts above 28 were excluded from the calculations. The results were displayed in an Excel graphic bar graph (Microsoft Corp., Redmond, Wash., USA) showing average fold change (2^ ΔΔCt) for CXCR4. Error bars depict +/− the Standard Deviation (SD) of the replicate measurements.

Results

An increase in CXCR4 mRNA expression was observed in umbilical cord blood CD34+ cells treated in SFEM with 10 µM 16,16-dimethyl $PGE_2$ (22 fold), or a combination of 10 µM dmPGE₂ and 10 µM glucocorticoid (50 to 61 fold), when compared to DMSO treated cells. A synergistic increase in CXCR4+ mRNA levels was detected following a combination treatment of 10 µM dmPGE₂ and 10 µM of any one of five different glucocorticoids (FIG. 1). Glucocorticoids act synergistically with dmPGE2 to increase CXCR4 gene expression.

Figure 2A:
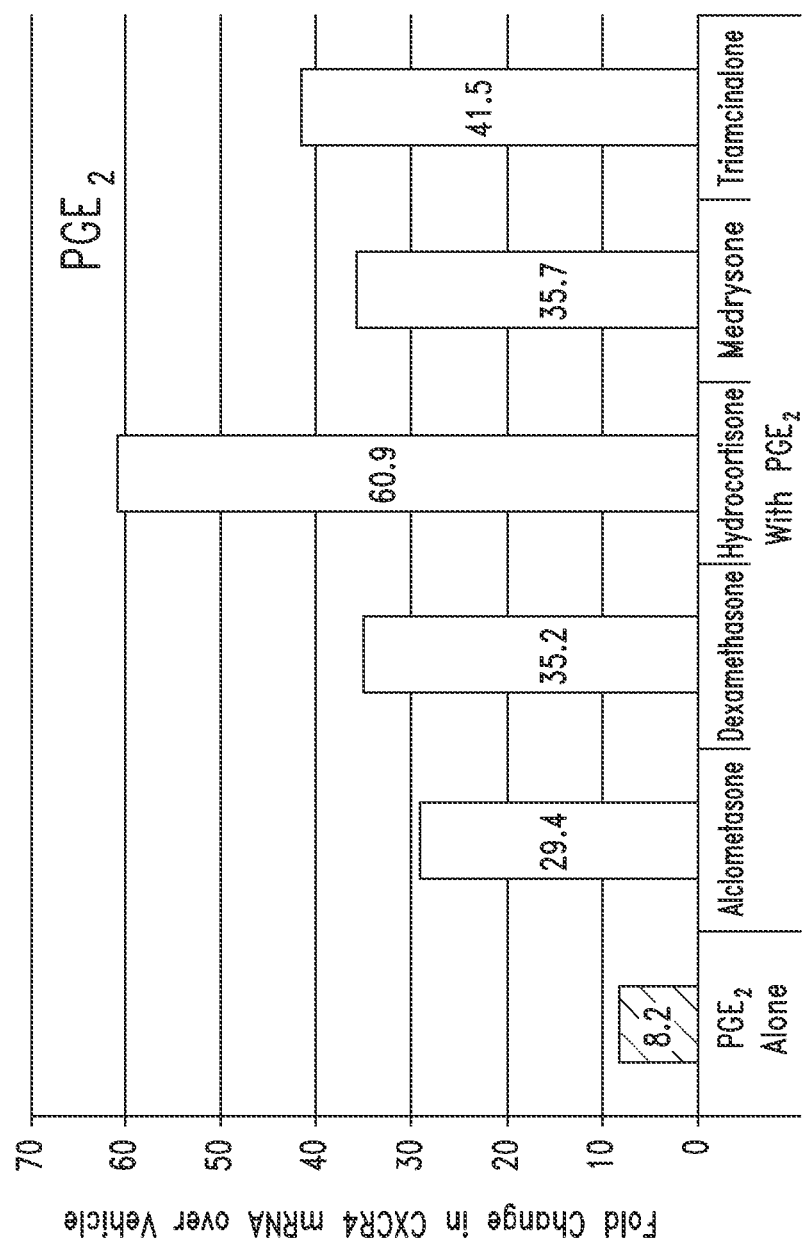
FIGS. 2A-2C show the increase in CXCR4 mRNA detected in human cord blood CD34+ cells when the CD34+ cells are treated with: PGE$_2$ alone or a combination of PGE$_2$ with various glucocorticoids (FIG. 2A); 15(S)-15-methyl PGE$_2$ (mPGE$_2$) alone or in combination with various glucocorticoids (FIG. 2B); or 20-ethyl PGE2 (ePGE$_2$) alone or in combination with various glucocorticoids (FIG. 2C). The data demonstrates that glucocorticoids act synergistically with prostaglandin pathway agonists to increase CXCR4 gene expression in CD34+ cells.
Figure 2B:
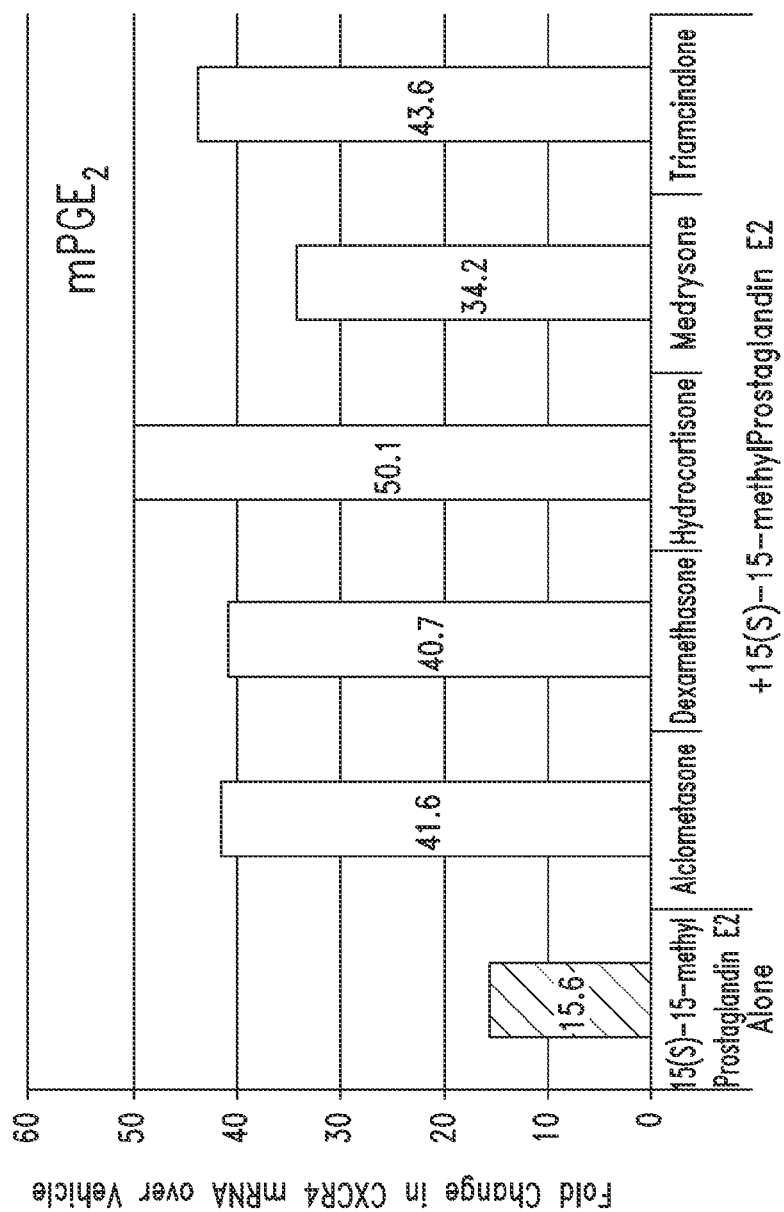
Figure 2C:
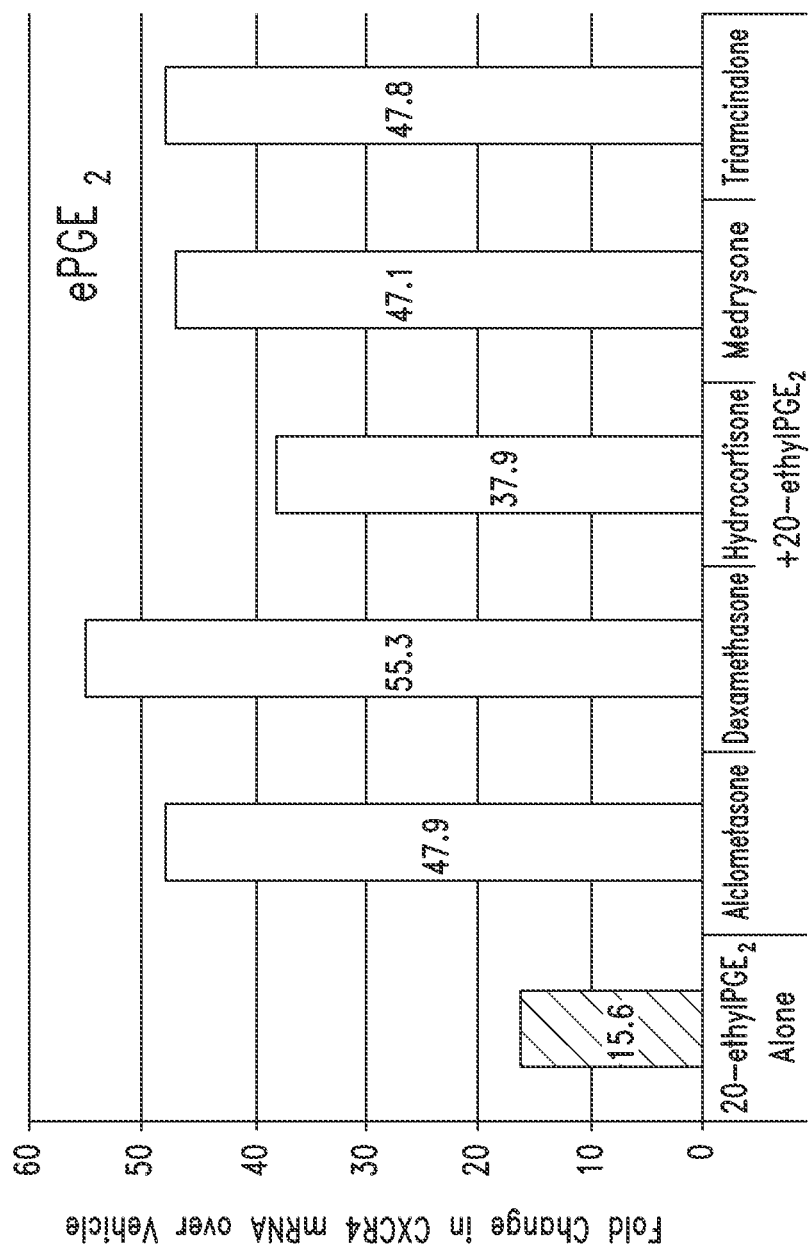

A similar synergistic increase in CXCR4 mRNA expression was also observed in umbilical cord blood CD34+ cells treated in SFEM for 4 hours with other prostaglandin pathway agonists, 10 µM $PGE_2$ (8 to 61 fold increase) (FIG. 2A), 10 µM 15,15-methyl $PGE_2$ (16 to 50 fold increase) (FIG. 2B), and 10 µM 20-ethyl $PGE_2$ (16 to 55 fold increase) (FIG. 2C) when combined with a glucocorticoid compared DMSO treated cells. Glucocorticoids also act synergistically with other prostaglandin pathway agonists to increase CXCR4 gene expression.

at 37° C., 5% $CO_2$ with 10 uM 16,16-dimethyl $PGE_2$ (dmPGE₂) alone or in combination with 10 uM medrysone. After treatment, cells were washed with SFEM and centrifuged at 300 g for 10 minutes.

Total RNA was then isolated from treated cells using Pico Pure RNA Isolation Kit (Molecular Devices, Sunnyvale, Calif., USA). Complimentary DNA (cDNA) was reverse transcribed from 50 ng of isolated total RNA using the High-Capacity cDNA Reverse Transcription Kit (Life Technologies).

Real-Time PCR analysis was run on the cDNA samples in duplicate. The reaction mix contained 1 µL Gene Specific Taqman Assay (20×) and 10 µL Gene Expression Master Mix (Life Technologies) with the remaining volume of 9 µL contained 10 ng cDNA and sterile $diH_2O$.

CXCR4 results (assay from Table 1) were analyzed using Applied Biosystems StepOne Software v2.1 Analysis software. Average Cts were calculated from the sample replicates and delta-delta Cts (ΔΔCt) were calculated using GAPDH results (assay from Table 1) as a reference gene against a vehicle only sample. Results were displayed in an Excel graphic bar graph (Microsoft Corp., Redmond, Wash., USA) showing average fold change (2^ ΔΔCt) for CXCR4. Error bars depict +/− the Standard Deviation (SD) of the replicate measurements (See FIGS. 1-3, 5, and 6).

Results

A similar increase in CXCR4 mRNA expression was observed in both cord blood derived CD34+ cells and CD34+ cells isolated from mobilized peripheral blood (22 and 27 fold increase respectively) after a 4 hour treatment in SFEM

TABLE 1

Applied Biosystems TaqMan Assays

| Gene | Assay ID | Gene | Assay ID | Gene | Assay ID | Gene | Assay ID |
|---|---|---|---|---|---|---|---|
| ANGPT1 | Hs00375822_m1 | CXCL6 | Hs00237017_m1 | PROM1 | Hs01009250_m1 | BMP4 | Hs00370078_m1 |
| ANGPT2 | Hs01048042_m1 | IKBKB | Hs00233287_m1 | PECAM1 | Hs00169777_m1 | TIE1 | Hs00178500_m1 |
| AREG | Hs00950669_m1 | CASP3 | Hs00234387_m1 | JAG1 | Hs01070032_m1 | GAPDH | Hs99999905_m1 |
| ARNT | Hs00231048_m1 | CREM | Hs01590456_m1 | CTGF | Hs00170014_m1 | CD40L | Hs00163934_m1 |
| BAX | Hs00180269_m1 | HGF | Hs00300159_m1 | SOD2 | Hs00167309_m1 | PDGFB | Hs00966522_m1 |
| THBS1 | Hs00962908_m1 | DUSP4 | Hs01027785_m1 | CYR61 | Hs00155479_m1 | CXCL1 | Hs00236937_m1 |
| TEK | Hs00945146_m1 | CFLAR | Hs01116280_m1 | IGF2 | Hs00171254_m1 | CXCR4 | Hs00976734_m1 |
| MMP2 | Hs01548727_m1 | FGF2 | Hs00266645_m1 | PTGS2 | Hs00153133_m1 | RAC2 | Hs01032884_m1 |
| PDGFR | Hs01019589_m1 | NR4A2 | Hs00428691_m1 | TERT | Hs00972656_m1 | TGFB1 | Hs00998133_m1 |
| MMP9 | Hs00234579_m1 | CD40 | Hs00374176_m1 | CD44 | Hs01075861_m1 | HMGB1 | Hs01923466_g1 |
| NOS3 | Hs01574659_m1 | KDR | Hs00911700_m1 | ITGB1 | Hs00559595_m1 | CTNNB1 | Hs00170025_m1 |
| CSF3 | Hs00357085_g1 | IL8 | Hs00174103_m1 | PLAUR | Hs00182328_m1 | DUSP4 | Hs00175210_m1 |
| BCL2 | Hs00608023_m1 | BMP2 | Hs00154192_m1 | CSF1 | Hs00174164_m1 | AKT1 | Hs00178289_m1 |
| VEGFA | Hs00900055_m1 | ICAM1 | Hs00164932_m1 | CXCL3 | Hs00171061_m1 | CASP8 | Hs01018151_m1 |
| CD34 | Hs00990732_m1 | IL1A | Hs00174092_m1 | CD47 | Hs00179953_m1 | CCL7 | Hs00171147_m1 |
| HIF1A | Hs00936371_m1 | EDN1 | Hs00174961_m1 | S1PR1 | Hs00173499_m1 | CCR1 | Hs00174298_m1 |
| SMAD4 | Hs00929647_m1 | FLT1 | Hs01052961_m1 | GEM | Hs00738924_m1 | CD151 | Hs00388381_m1 |
| PGF | Hs01119262_m1 | NFKB1 | Hs00765730_m1 | SMAD2 | Hs00183425_m1 | CXCR7 | Hs00604567_m1 |
| TGFB3 | Hs01086000_m1 | CXCL5 | Hs00171085_m1 | CCND1 | Hs00765553_m1 | HBEGF | Hs00181813_m1 |
| NR3C1 | Hs00353740_m1 | TNF | Hs00174128_m1 | ITGAL | Hs00158218_m1 | CXCR2 | Hs01011557_m1 |
| STAT1 | Hs01013996_m1 | ITGA4 | Hs00168433_m1 | LIF | Hs00171455_m1 | RASA1 | Hs00243115_m1 |
| CDH5 | Hs00901463_m1 | HPRT1 | Hs01003267_m1 | EFNB2 | Hs00187950_m1 | RGS16 | Hs00161399_m1 |
| CXCL2 | Hs00601975_m1 | ITGA5 | Hs01547673_m1 | CXCL12 | Hs00171022_m1 | TIMP1 | Hs00171558_m1 |
| FOSL2 | Hs00232013_m1 | ITGB2 | Hs00164957_m1 | QARS | Hs00192530_m1 | TIMP2 | Hs00234278_m1 |

CXCR4 qPCR Using the Applied Biosystems StepOnePlus

Figure 3:
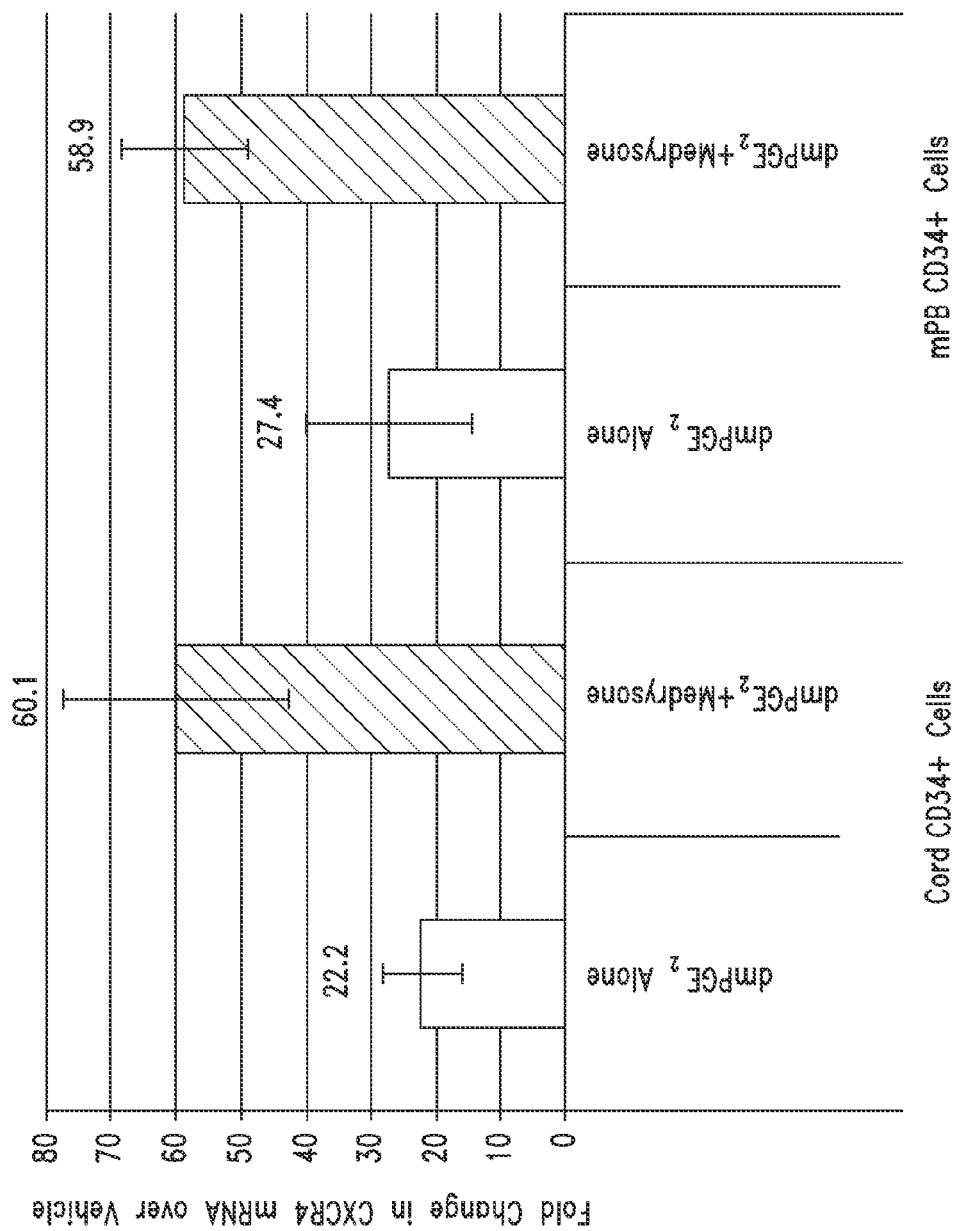
FIG. 3 shows the increase in CXCR4 mRNA detected in human CD34+ cells derived from cord blood or mobilized peripheral blood (mPB) when the CD34+ cells are treated with either a prostaglandin pathway agonist alone or in combination with a glucocorticoid. CD34+ cells respond similarly to treatment regardless of source of origin of the CD34+ cells.

Real-time PCR transcript quantitation from ex vivo treated cord CD34+ cells (Stem Cell Technologies, Vancouver, BC, Canada) and mobilized peripheral blood CD34+ cells (All Cells, LLC, Emoryville, Calif., USA) was performed using the Applied Biosystems StepOne Plus system (Life Technologies Corporation, Carlsbad, Calif., USA) (see FIG. 3). CD34+ cells were treated in SFEM for four hours with 10 µM 16,16-dimethyl $PGE_2$. A similar synergistic increase in CXCR4 mRNA was detected in both cord blood derived CD34+ cells and CD34+ cells isolated from mobilized peripheral blood (60 and 59 fold respectively) after a 4 hour combination treatment in SFEM with a prostaglandin pathway agonist (dmPGE₂) and a glucocorticoid (medrysone) (FIG. 3). CD34+ cells respond similarly to either treatment regardless of source of origin.

Example 2

Treatment of CD34+ Cells with a Combination of dmPGE₂ and Medrysone Results in Increased CXCR4 Surface Protein Expression CXCR4 Surface Expression Analysis on frozen CD34$^{+CB\ and\ PB}$ CD34+ cord blood (CB) cells (Stem Cell Technologies) and CD34+ mobilized peripheral blood (mPB) cells (All Cells) were treated in SFEM for 2 and 4 hours at 37° C., 5% $CO_2$ with 10 µM dmPGE₂, dmPGE₂ and medrysone, or DMSO as control. After treatment, cells were washed with SFEM and centrifuged at 300 g for 10 minutes. Cells were then resuspended in SFEM for incubation at 37° C. 5% $CO_2$ for diverse amount of time.

mPB and CB CD34+ cells were treated in SFEM for 2 or 4 hours with dmPGE₂, dmPGE₂ and medrysone, or DMSO, and cells were then assessed for CXCR4 surface protein expression at different time points during and after treatment (Table 2). In order to measure CXCR4 levels treated cells were centrifuged at 300 g for 10 minutes and resuspended in staining media containing Lineage cocktail 1-FITC, CD34-APC, CXCR4(CD184)-PE, and incubated on ice for 20 minutes. Fresh staining media was then added to the cells to wash the cells from any residual unbound antibodies, the cells were centrifuged at 300 g for 10 minutes, and this washing procedure was repeated twice. The stained cells were acquired on a Guava EasyCyte 8HT flow cytometer and analysis was performed using FloJo Software Package (Treestar).

TABLE 2

Treatments and time points used for CXCR4 protein surface analysis

| Time | Treatments | | |
|---|---|---|---|
| 2 hr Tx | DMSO | 10 uM dmPGE2 | 10 uM dmPGE2 + 10 uM Medrysone |
| 2 hr Tx + 2 hr at 37° C. | | | |
| 2 hr Tx + 4 hr at 37° C. | | | |
| 4 hr Tx | | | |
| 4 hr Tx + 2 hr at 37° C. | | | |
| 4 hr Tx + 4 hr at 37° C. | | | |

Results

Figure 5:
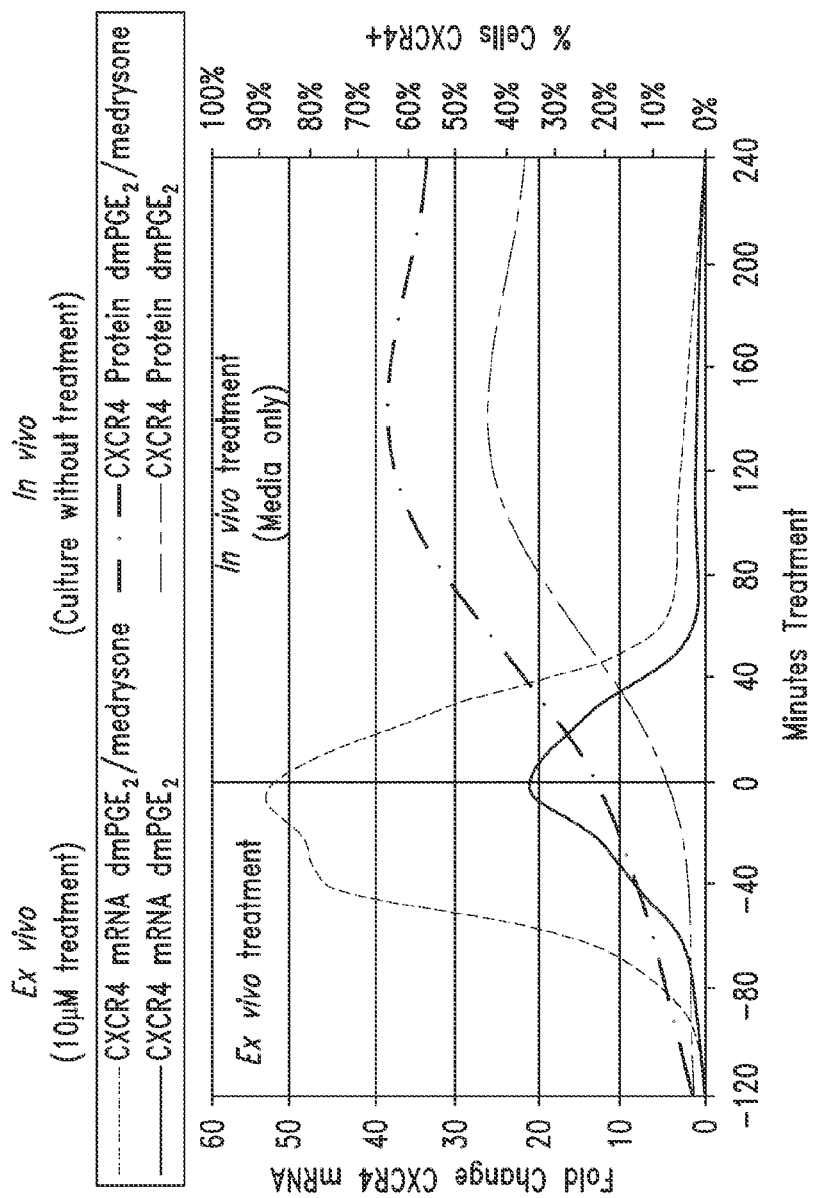
FIG. 5 shows the kinetic measurement of the increase in CXCR4 mRNA detected (fold change) and the number of human CD34+ cells expressing surface CXCR4 protein (% Cells CXCR4+) during a 2 hour treatment and for an additional 4 hours post-removal of treatment (media alone) after the CD34+ cells are treated with either a prostaglandin pathway agonist alone or in combination with a glucocorticoid.
Figure 6:
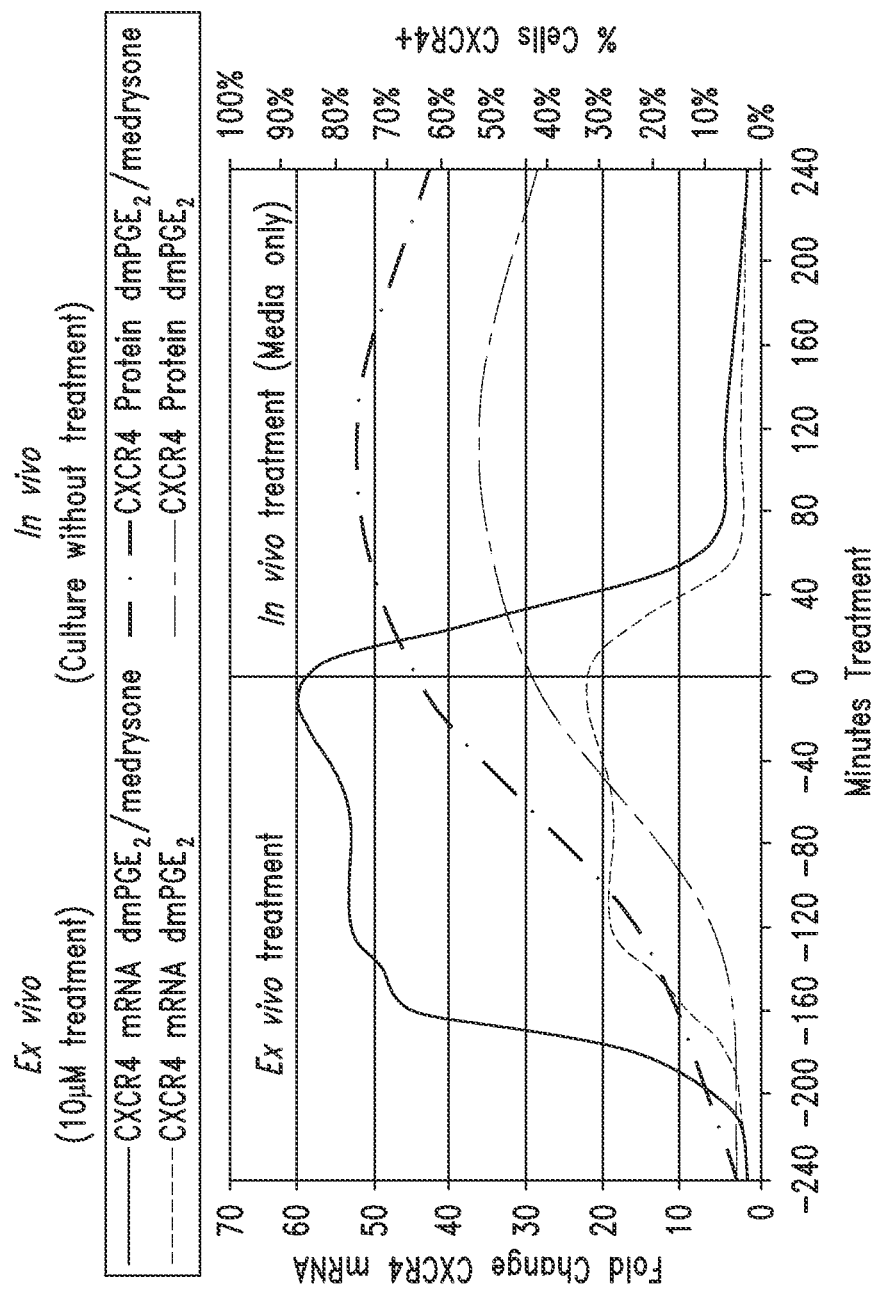
FIG. 6 shows the kinetic measurement of the increase in CXCR4 mRNA detected (Fold Change) and the number of human CD34+ cells expressing surface CXCR4 protein (% Cells CXCR4+) during a 4 hour treatment and for an additional 4 hours post removal of treatment (media alone) after the CD34+ cells are treated with either a prostaglandin pathway agonist alone or in combination with a glucocorticoid.

An increase in CXCR4 RNA expression was observed in CD34+ cells from cord blood or mPB cells treated in SFEM with 10 µM 16,16-dimethyl PGE₂ and dmPGE₂ and medrysone for 2 and 4 hours at 37° C. when compared to DMSO treated cells. The highest percentage of CXCR4+ cells was obtained 2 hours after a 4 hour treatment with dmPGE₂ and medrysone (FIGS. 5 and 6) for both type of cells regardless of the cell source. For mobilized peripheral blood CD34+ cells, 75% of the cells expressed CXCR4+ compared to 8% for control (FIG. 5). For cord blood CD34+ cells, 25% of the cells expressed CXCR4 after dmPGE₂ and medrysone treatment compared to 3-6% for control samples (FIG. 6).

Figure 4A:
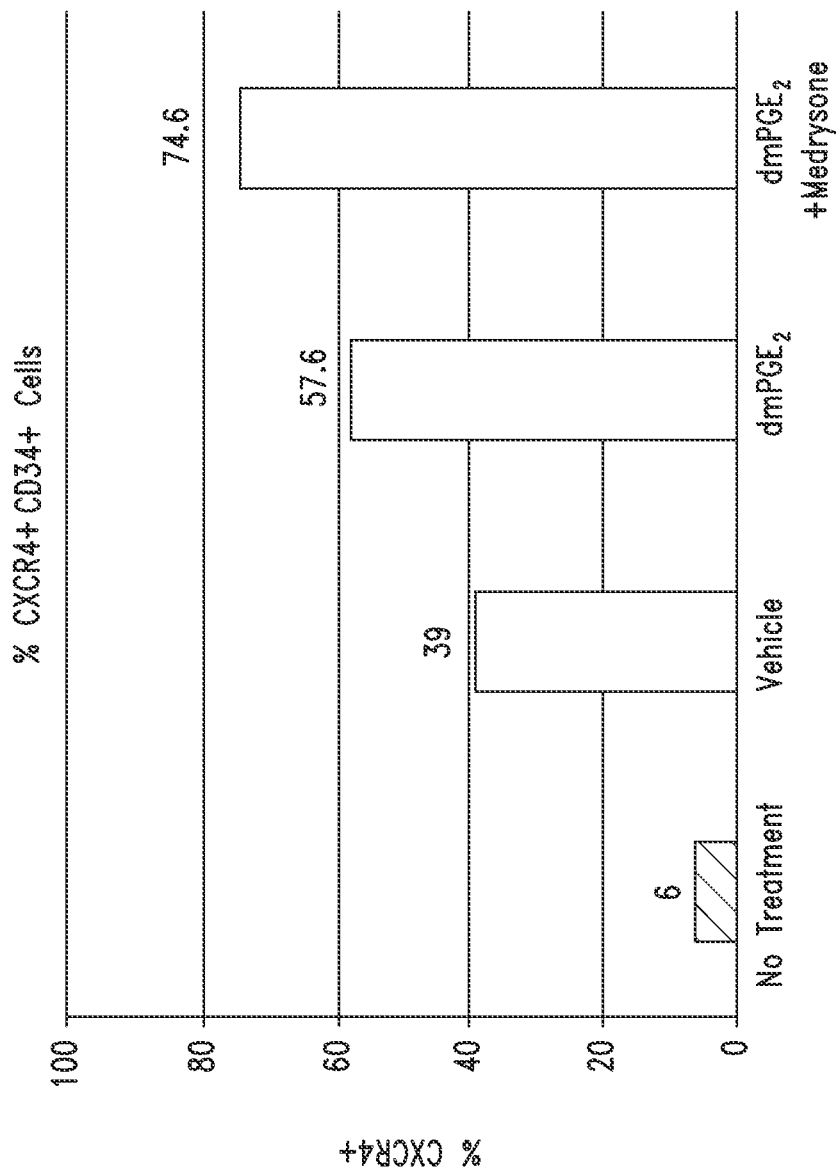
FIGS. 4A-4B show the increase in the number of CD34+ cells expressing CXCR4 surface protein (FIG. 4A), depicted as % CXCR4+, and the increase in the amount of CXCR4 surface protein on the CD34+ cells (FIG. 4B) measured in Mean Fluorescent Intensity (MFI) after the CD34+ cells are treated with either a prostaglandin pathway agonist alone or in combination with a glucocorticoid.
Figure 4B:
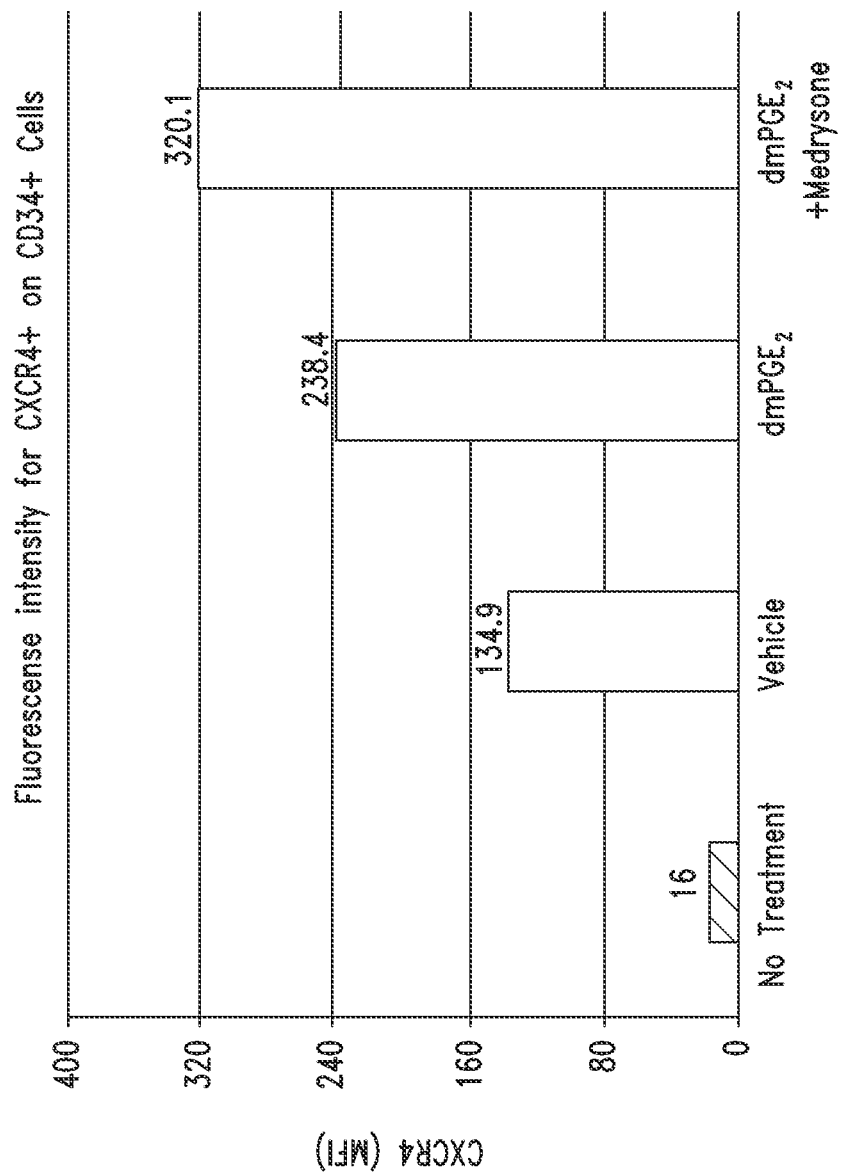

CD34+ cells from human bone marrow were also tested for their ability to respond to 16,16-dimethyl PGE₂ and the combination of dmPGE₂ and medrysone. In this case, previously frozen bone marrow CD34+ were treated in SFEM with 10 µM 16,16-dimethyl PGE₂+10 µM medrysone for 4 hours at 37° C. i. Cells were then washed and resuspended in SFEM for 2 hours. The CXCR4 surface protein was then assessed by flow cytometry as previously described. Treatment of BM CD34+ cells in SFEM with 10 µM 16,16-dimethyl PGE₂ alone or 10 µM 16,16-dimethyl PGE₂+10 µM medrysone results in an increase in the level of CXCR4 protein expression of 12 and 20 fold increase, respectively. Furthermore, treatment in SFEM with 10 µM 16,16-dimethyl PGE₂+10 µM medrysone results in a 12-fold increase in the percentage of CXCR4+ cells (FIGS. 4A and 4B).

Example 3

Sdf-1 Transwell Migration Assays

Methods

Transwell migration assays were performed using 96-well chemotaxis chambers, 5 µM pore size polycarbonate membrane (Corning Inc., Corning, N.Y.) in accordance with manufacturer's instructions. Briefly, CD34+ cells were then treated for 4 hours at 37° C. with 16,16-dimethyl PGE₂ (dmPGE₂), dmPGE₂ and glucocorticoid, or DMSO control at a concentration of 10 µM in StemSpan® media (Stem Cell Technology, Vancouver, Canada). The cells were then washed by centrifugation (300×g for 10 minutes) and resuspended in transwell assay buffer (Phenol Red Free RPMI media (Mediatech), 0.5% lipid free BSA (Sigma-Aldrich) at a concentration of 40,000-60,000 cells/75 µl.

To test the duration of the treatment effects, one portion of treated cells was washed by centrifugation (300×g for 10 minutes) and resuspended in StemSpan® media for 4 hours at 37° C. without dmPGE₂, glucocorticoids, or DMSO and then washed again by centrifugation (300×g for 10 minutes) and resuspended in transwell assay buffer (Phenol Red Free RPMI media (Mediatech), 0.5% lipid free BSA (Sigma-Aldrich) at a concentration of 40,000-60,000 cells/75 µl.

Seventy-five µl of cell suspension was added to the upper chamber of the plate, while 235 µl of transwell assay media containing 0 or 50 ng/ml SDF1α (R&D system, Minneapolis, Minn.) was added to the bottom well. Total cell number in the lower well was obtained by flow cytometry after 2.5 hours of incubation at 37° C., 5% $CO_2$.

Results

Figure 7:
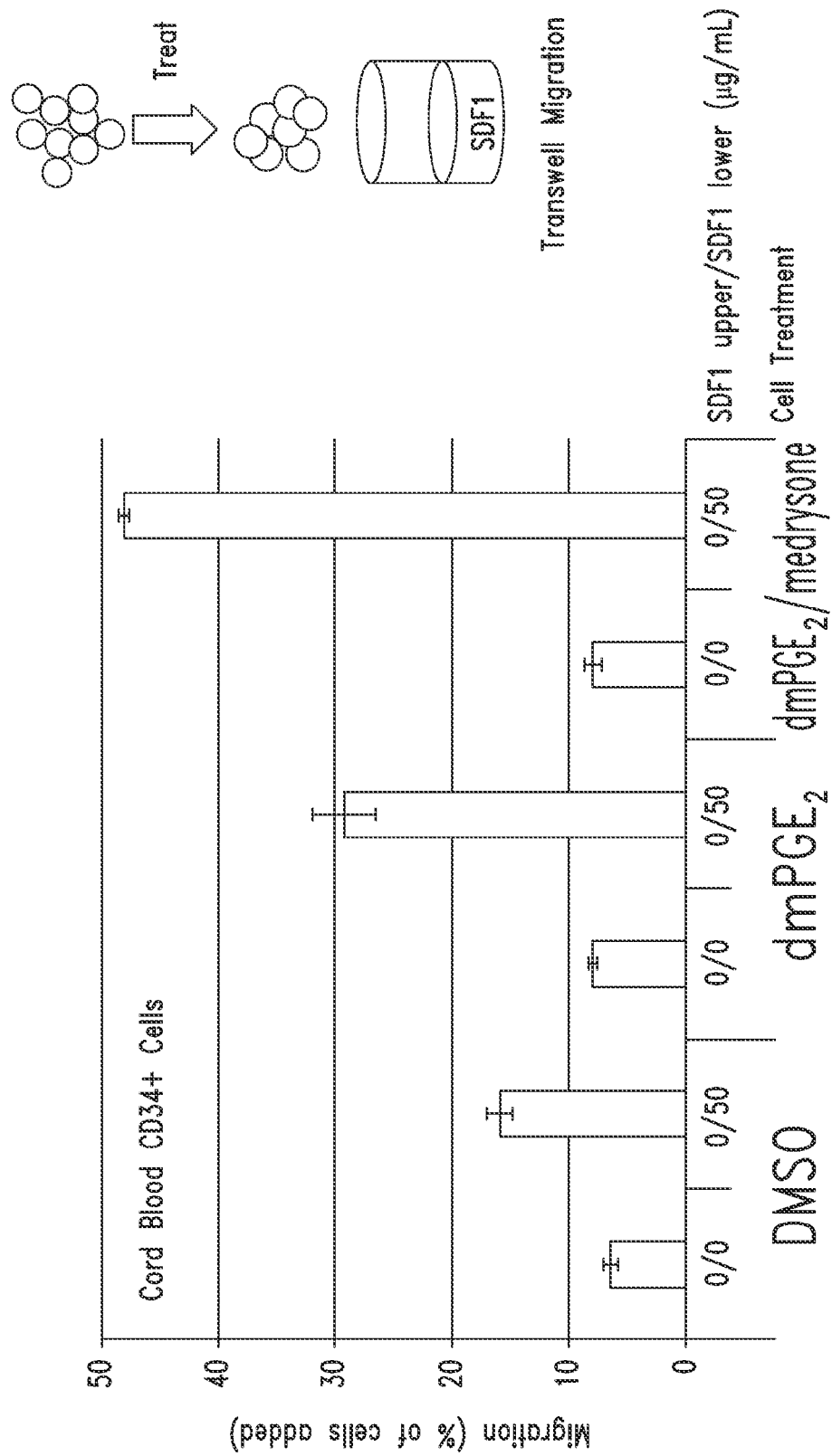
FIG. 7 shows the results from a representative SDF-1 transwell migration assay. The results show the effect of treating CD34+ cells with DMSO control, dmPGE$_2$, or dmPGE$_2$ and medrysone on the efficiency of cell migration towards SDF-1. The data demonstrates the enhanced ability of CD34+ cells treated with a combination of a prostaglandin pathway agonist and a glucocorticoid to migrate to an SDF-1 gradient in comparison to CD34+ cells treated with vehicle or a prostaglandin pathway agonist alone. The results indicate that the increase in CXCR4 gene expression in cells treated with the combination of a prostaglandin pathway agonist and a glucocorticoid translates to increased functional ability.

CD34+ cells were treated with DMSO control, dmPGE₂, or dmPGE₂ and medrysone as described above. The treated cells were placed in the upper chambers of a transwell culture plate with 0 ng/mL SDF1 or 50 ng/mL SDF1 in the lower chambers. Migration was expressed as the % of cells added, i.e., the number of cells in the lower chamber normalized to the number of cells initially added to the upper chamber. dmPGE₂ treatment increased SDF1-driven migration compared to the DMSO control (See FIG. 7). The combination treatment of dmPGE₂ and medrysone increased SDF1-driven cell migration more than dmPGE₂ alone or DMSO control (See FIG. 7). Thus, CD34+ cells in SFEM treated with dmPGE₂, or dmPGE₂ and medrysone migrated more efficiently towards SDF1 compared to DMSO control treated cells.

Figure 8:
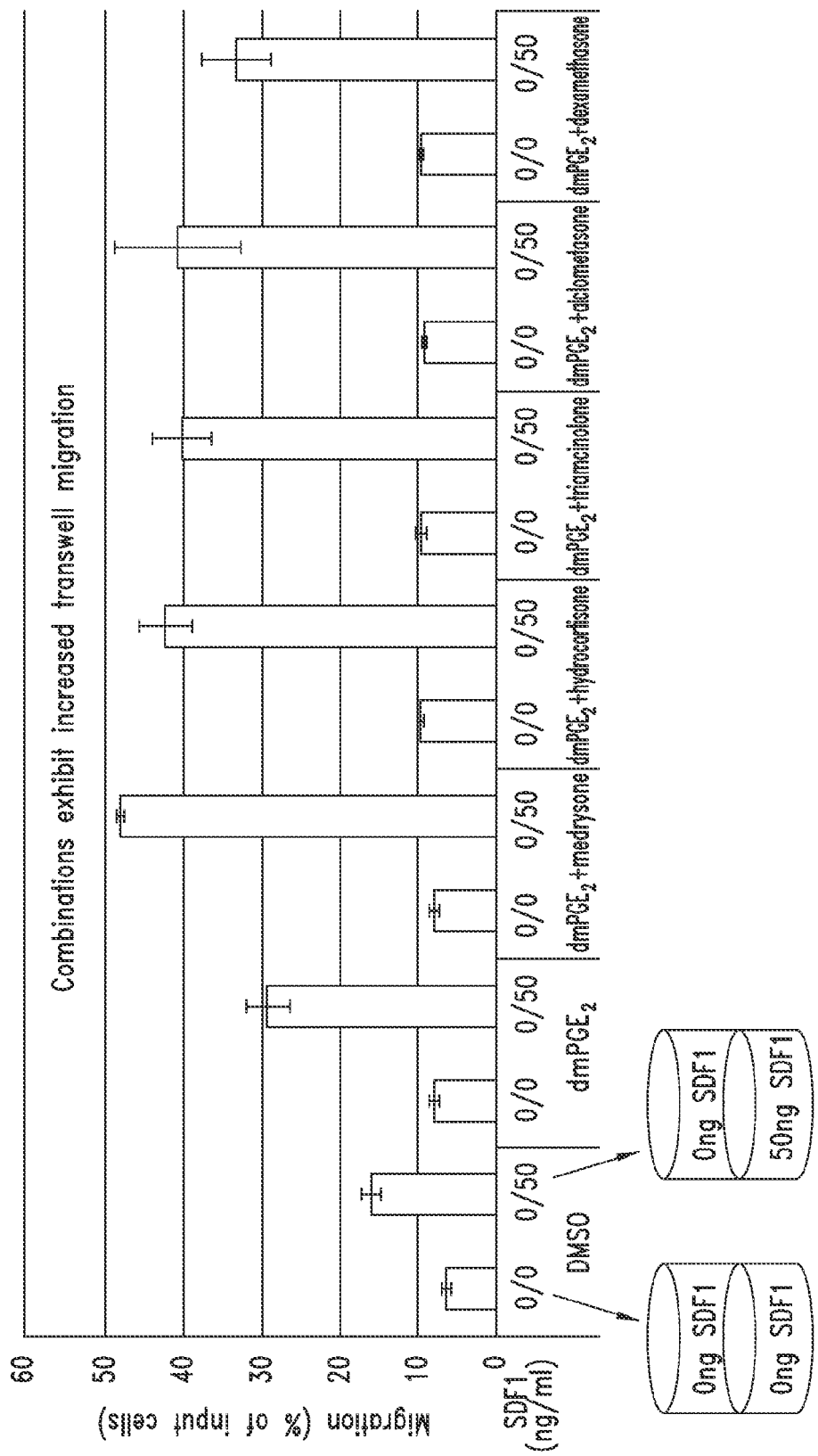
FIG. 8 shows the efficiency of cell migration towards SDF-1 of CD34+ cells treated with dmPGE$_2$ alone or in combination with various glucocorticoids. CD34+ cells treated with the combination of a prostaglandin pathway agonist and a glucocorticoid show increased ability to migrate towards an SDF-1 gradient as compared to CD34+ cells treated with vehicle or a prostaglandin pathway agonist alone.

CD34+ cells were treated with DMSO control, dmPGE₂, or dmPGE₂ and a glucosteroid (medrysone, hydrocortisone, triamcinolone, alclometasone, alclometasone dipropionate, or dexamethasone) as described above. The treated cells were placed in the upper chambers of a transwell culture plate with 0 ng/mL SDF1 or 50 ng/mL SDF1 in the lower chambers. Migration was expressed as the % of cells added, i.e., the number of cells in the lower chamber normalized to the number of cells initially added to the upper chamber. dmPGE₂ treatment increased SDF1-driven cell migration compared to the DMSO control (See FIG. 8). Moreover, treatment with dmPGE2 combined with either medrysone, hydrocortisone, triamcinolone, alclometasone, alclometasone dipropionate, or dexamethasone increased SDF1-driven cell migration more effectively than dmPGE2 alone or DMSO control (See FIG. 8). Thus, CD34+ cells treated in SFEM with dmPGE$_2$, or dmPGE$_2$ and various glucocorticoids migrated more efficiently towards SDF1 compared to DMSO control treated cells and showed that the enhanced migration property of the prostaglandin pathway agonist/glucocorticoid treated cells is not limited to a particular glucocorticoid.

Figure 9:
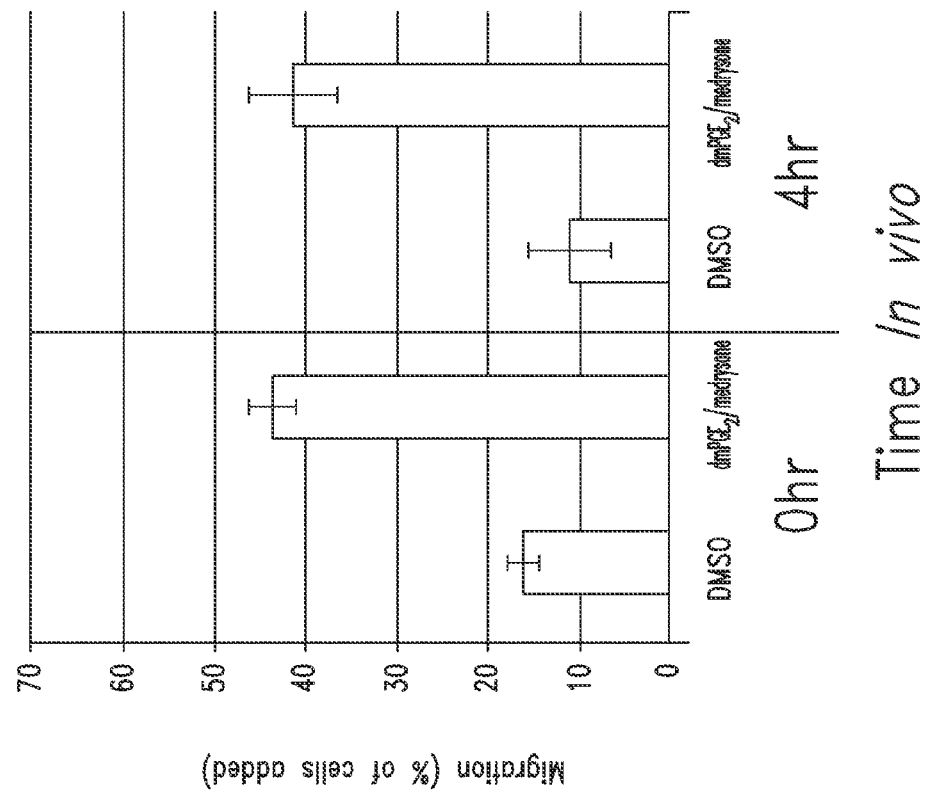
FIG. 9 shows the duration of the enhanced migration ability of CD34+ cells treated with a combination of a prostaglandin pathway agonist and a glucocorticoid. The results demonstrate that the duration of the enhanced migration ability is maintained for at least 4 hours after treatment of CD34+ cells.
Figure 9:
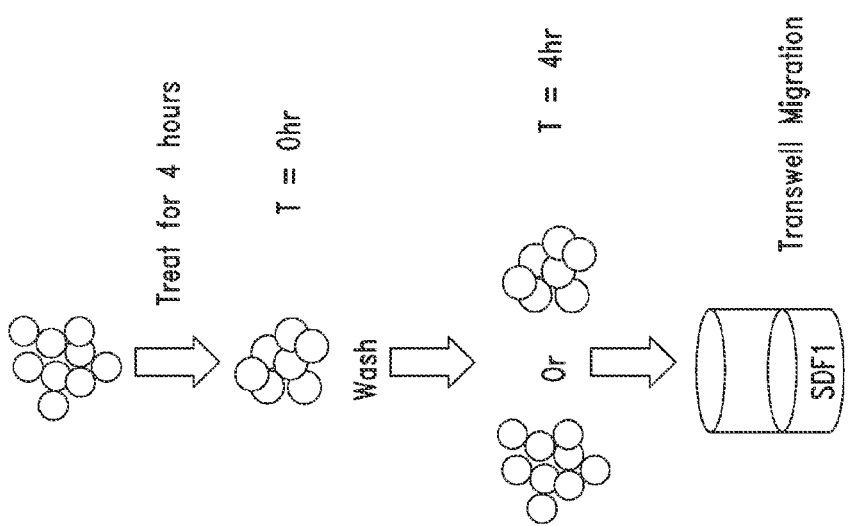

The duration of the enhanced migration effect of dmPGE$_2$/glucocorticoid treated cells towards SDF-1 was tested. CD34+ cells were treated with DMSO or dmPGE$_2$ and medrysone. Freshly treated cells or treated cells incubated for an additional 4 without further treatment (as described above) were placed in the upper chambers of a transwell culture plate with 0 ng/mL SDF1 or 50 ng/mL SDF-1 in the lower chambers. Migration was expressed as the % of cells added, i.e., the number of cells in the lower chamber normalized to the number of cells initially added to the upper chamber. dmPGE$_2$ and medrysone treatment increased SDF1-driven cell migration compared to the DMSO control (See FIG. 9). Moreover, dmPGE$_2$ and medrysone treated cells incubated for an additional 4 hours with no further treatment migrated as well as the freshly treated cells. Thus, the enhanced migration effect of prostaglandin pathway agonist/glucocorticoid treated cells towards SDF-1 is stable for at least four hours, an indicated that the effect would also be present in administering the treated cells to a subject.

Example 4

PGE$_2$ and PGE$_2$/Glucocorticoid Treated CD34+ Cells Improve Neurological and Locomotor Function in a Rat Ischemia Model Methods Adult male Wistar rats were subjected to a transient focal ischemia by blocking the right middle cerebral artery MCAO model (Middle Cerebral Artery Occlusion). A surgical nylon suture with a rounded tip was advanced from the external carotid artery into the lumen of the internal carotid artery until it blocked the origin of the middle cerebral artery. After 2 hours, the suture was withdrawn to allow reperfusion. One day after reperfusion, rats were injected via tail vein with either Hanks Balanced Salt Solution (HBSS), DMSO-treated CD34+ cells, or CD34+ cells treated with dmPGE$_2$ and medrysone. A phospodiesterase type 4 inhibitor (YM976) was also included to increase the durability of the enhanced cell effect. Our work demonstrates that PDE4 inhibitors do not significantly change the properties of the enhanced cell. Cells were incubated with compound or DMSO in culture medium for 4 hours at 37° C. Before injection, pretreated cells were centrifuged; the resultant supernatant was aspirated; and the cell pellet was resuspended in HBSS.

One day and 1, 2, 3, 4 and 5 weeks after injection, rats were assessed for neurological deficits with behavioral testing performed by an investigator who was blinded to the experimental groups. A modified Neurological Severity Score (mNSS) was calculated based on a published panel of motor, sensory, balance and reflex tests (Chen et al., *Stroke* 32:2682-2688 (2001)).

In addition, 1 day and 1, 2, 3, 4 and 5 weeks after injection, locomotor function was evaluated in the treated rats with a foot-fault test in which the animal crossed a perforated walkway. The total number of forelimb steps and the number of missteps, in which the left forelimb fell through a perforation, were measured.

Results

Figure 10:
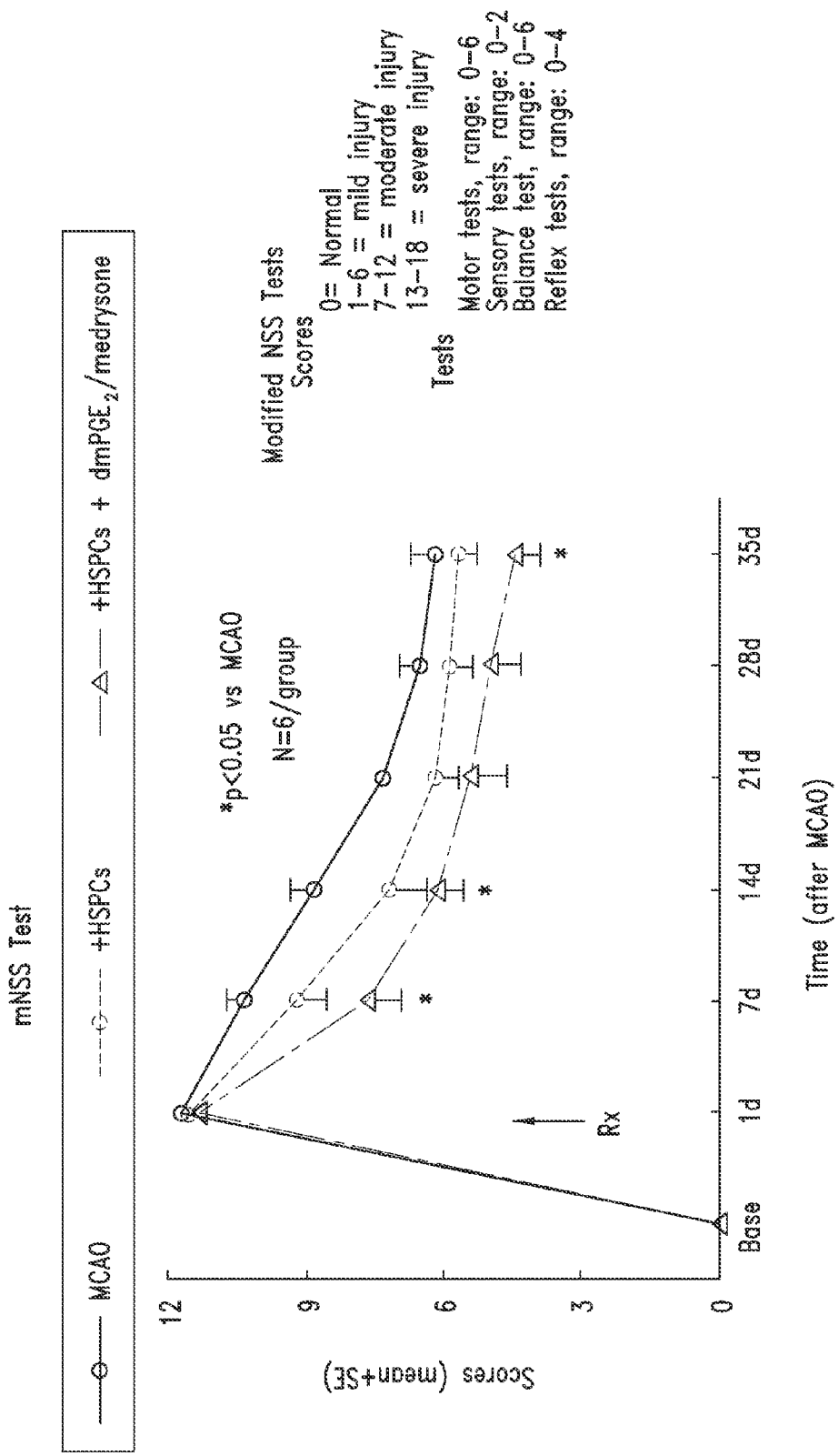
FIG. 10 shows the Neurological Severity Score (mNSS) results from a representative middle cerebral artery occlusion model (MCAO) ischemia rat model. The results show the effect of treating HSPCs cells with dmPGE$_2$ and medrysone on the ability of the cells to reduce neurological deficits in the MCAO stroke model. Neurological deficits are reduced, and neurological function is improved, in rats given HSPCs treated with the combination of a prostaglandin pathway agonist and a glucocorticoid, as compared to rats given untreated cells or vehicle alone.

Rats were administered treated HSPCs, and the ability of the treatment effect to reduce neurological deficit in the MCAO stroke model was tested. Treated HSPCs were intravenously injected 24 hours after unilateral ischemic brain injury. Neurological function was assessed with a battery of behavioral tests and reported as mNSS. Cells treated with dmPGE$_2$ and medrysone significantly improved mNSS at 7, 14 and 35 days compared to vehicle control, while DMSO-treated cells did not significantly affect mNSS (See FIG. 10). *$p<0.05$ (n=6/group).

Figure 11:
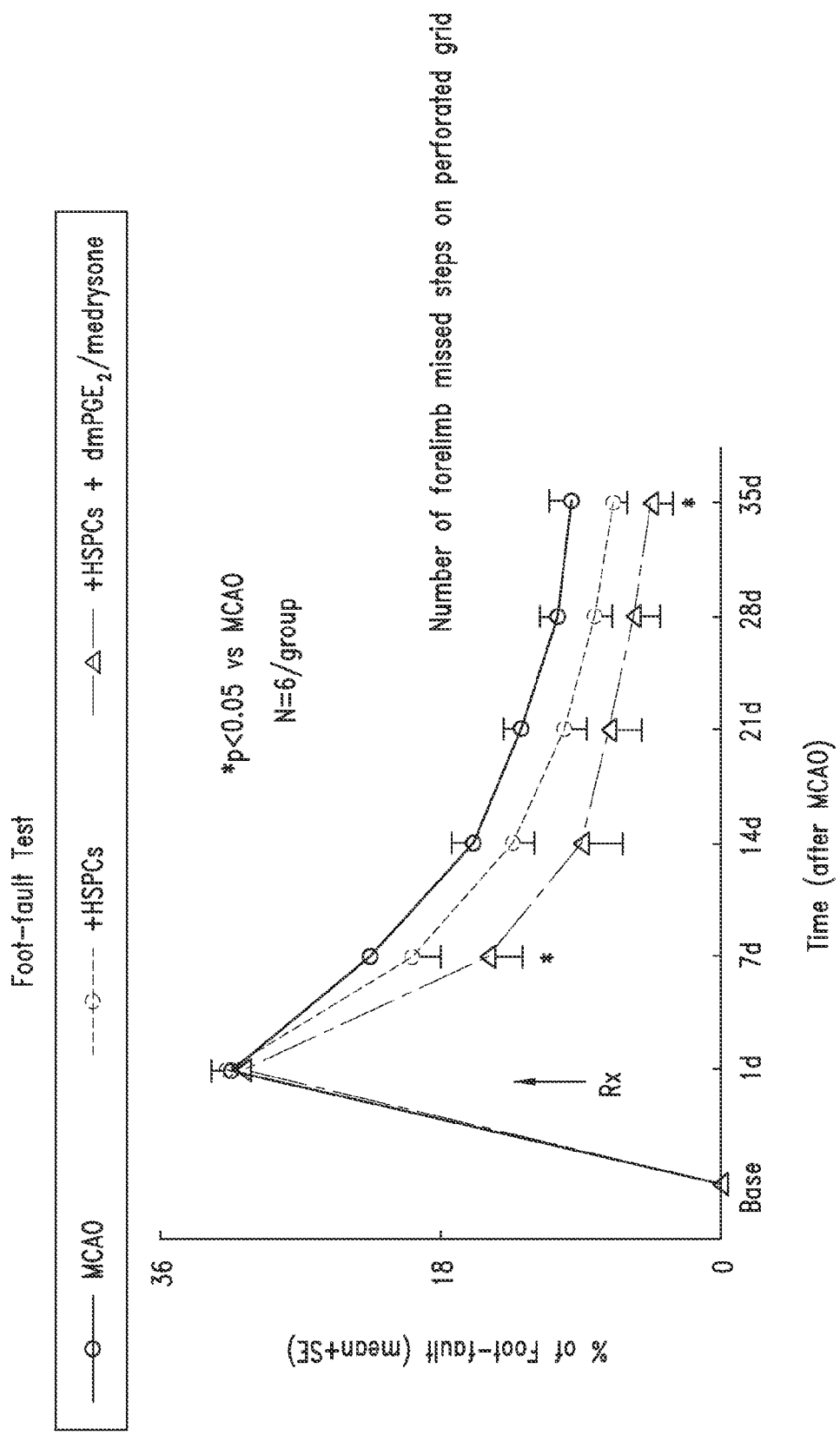
FIG. 11 shows the foot-fault assay results from a representative middle cerebral artery occlusion model (MCAO) ischemia rat model. The results show the effect of treating HSPCs with dmPGE$_2$ and medrysone on the ability of the cells to reduce locomotor deficits in the MCAO stroke model. Locomotor deficit is improved in rats given HSPCs treated with the combination of a prostaglandin pathway agonist and a glucocorticoid, as compared to rats given untreated cells or vehicle alone.

Rats were administered HSPCs treated with dmPGE$_2$ and medrysone, and the ability of the treatment effect to reduce locomotor deficit in the MCAO stroke model was tested. Treated HSPCs were intravenously injected 24 hours after unilateral ischemic brain injury. Locomotor function was assessed as % foot-faults when crossing a perforated walkway. Cells treated with dmPGE$_2$ and medrysone significantly decreased % foot-faults at 7 and 35 days compared to vehicle control, while DMSO-treated cells did not significantly affect % foot-faults (See FIG. 11). *$p<0.05$ (n=6/group).

Thus, the HSPCs treated with a prostaglandin pathway antagonist and a glucocorticoid effectively treated ischemia and the symptoms associated therewith, in the rat MCAO model.

Example 5

Methods

Isolation of Lin(−) CD34+ Cells from Treated Whole Cord Blood

Human whole cord blood mononuclear cells were obtained from Stem Cell Technologies (Vancouver, Canada). Upon thawing, the cells were treated with 16,16-dimethyl PGE$_2$ or appropriate controls, e.g., DMSO, in LMD/5% HSA medium.

After treatment, the cells were washed with LMD/5% HSA medium, centrifuged for 10 minutes at 650×g at room temperature and resuspended in a cold selection buffer (phosphate buffered saline (PBS) with no Ca+ or Mg+; 2 mM EDTA; and 0.5% HSA). Magnetic selection was performed using the Lineage (Lin) Depletion Kit (Miltenyi Biotec, CA) followed by a CD34+ enrichment kit (Miltenyi Biotec). Lineage depletion and CD34+ cell enrichment were performed according to manufacturer's instructions using a QuadroMACS™ separator. During this process, the cells were kept at 4° C. Once the Lin-CD34+ cells were isolated from the treated whole cord blood, an aliquot was analyzed by flow cytometry to assess purity. Purity of the cells was greater than 90%. The majority of the cells were used for RNA extraction using the Pico Pure RNA Isolation Kit (Molecular Devices, Sunnyvale, Calif.) for Affymetrix analysis.

The CD34+ cells described in the above examples were isolated from cord blood, mobilized peripheral blood and bone marrow cells, as noted, and obtained from Stem Cell Technologies and All Cells LLC. Upon receiving these cells, the level of differentiated cells contamination was determined by flow cytometry, based on the amount of lineage markers present on the surface of the CD34+ cells. CD34+ cells expressing lineage markers are differentiated progenitor cells that do not have the same self-renewal capacity as lineage negative CD34+ cells. All CD34+ cells obtained from these companies and referenced in the experiments herein were at least 85% CD34+/Lin(−) cells.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A human hematopoietic stem or progenitor cell that has been contacted ex vivo with one or more agents that increase CXCR4 gene expression in the cell by at least about 30 fold in the contacted hematopoietic stem or progenitor cell compared to a hematopoietic stem or progenitor cell that has not been contacted ex vivo with one or more agents that increase CXCR4 gene expression.

2. The hematopoietic stem or progenitor cell of claim 1, wherein the one or more agents comprise (i) one or more prostaglandin pathway agonists; and (ii) one or more glucocorticoids.

3. The hematopoietic stem or progenitor cell of claim 2, wherein the one or more prostaglandin pathway agonists comprises $PGE_2$ or a $PGE_2$ analogue or derivative thereof.

4. The hematopoietic stem or progenitor cell of claim 2, wherein the one or more glucocorticoids is selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6amethylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol.

5. The hematopoietic stem or progenitor cell of claim 1, wherein the cell is obtained from bone marrow, umbilical cord blood, mobilized peripheral blood, Wharton's jelly, placenta, or fetal blood.

6. A therapeutic composition comprising a population of cells comprising human hematopoietic stem or progenitor cells contacted ex vivo with one or more agents under conditions sufficient to increase CXCR4 expression in the human hematopoietic stem or progenitor cells by at least about 30 fold compared to hematopoietic stem or progenitor cells that have not been contacted ex vivo with one or more agents that increase CXCR4 gene expression.

7. The therapeutic composition of claim 6, wherein the one or more agents comprise (i) one or more prostaglandin pathway agonists and (ii) one or more glucocorticoids.

8. The therapeutic composition of claim 6, wherein gene expression of CXCR4 is increased by at least about 40 fold in the contacted hematopoietic stem or progenitor cells compared to hematopoietic stem or progenitor cells that have not been contacted ex vivo with one or more agents that increase CXCR4 gene expression.

9. The therapeutic composition of claim 7, wherein the one or more prostaglandin pathway agonists comprises $PGE_2$ or a $PGE_2$ analogue or derivative thereof.

10. The therapeutic composition of claim 7, wherein the one or more glucocorticoids is selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol.

11. The therapeutic composition of claim 6, wherein the hematopoietic stem or progenitor cells have been contacted for a time of at least about one hour with at least one of (i) one or more prostaglandin pathway agonists and (ii) one or more glucocorticoids.

12. The therapeutic composition of claim 6, wherein the population of cells comprises at least about 0.01% and no more than about 50% of CD34+ cells.

13. The therapeutic composition of claim 6, wherein the composition is not cultured.

14. A method of increasing hematopoietic stem or progenitor cell homing, engraftment, or reconstitution in a subject comprising administering to the subject a composition comprising a population of cells comprising human hematopoietic stem or progenitor cells wherein:
   a) the hematopoietic stem or progenitor cells have been contacted ex vivo with one or more agents that increase CXCR4 gene expression in the cells; and
   b) gene expression of CXCR4 is increased at least about 30 fold in the contacted hematopoietic stem or progenitor cells compared to hematopoietic stem or progenitor cells that have not been contacted ex vivo with one or more agents that increase CXCR4 gene expression in the cells.

15. The method of claim 14, wherein the one or more agents comprise (i) one or more prostaglandin pathway agonists; and (ii) one or more glucocorticoids.

16. The method of claim 14, wherein the hematopoietic stem or progenitor cells are obtained from bone marrow, umbilical cord blood, mobilized peripheral blood, Wharton's jelly, placenta, or fetal blood.

17. The method of claim 15, wherein gene expression of CXCR4 is increased by at least about 40 fold in the contacted hematopoietic stem or progenitor cells compared to hematopoietic stem or progenitor cells that have not been contacted ex vivo with one or more agents that increase CXCR4 gene expression.

18. The method of claim 15, wherein the prostaglandin pathway agonist comprises $PGE_2$ or a PGE2 analogue or derivative thereof.

19. The method of claim 15, wherein the one or more glucocorticoids are selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol.

20. The method of claim 15, wherein the hematopoietic stem or progenitor cells have been contacted with one or more prostaglandin pathway agonists and one or more glucocorticoids for a time of at least about one hour.

21. The method claim 15, wherein the population of cells comprises at least about 0.01% and no more than about 50% of CD34+ cells.

22. The method of claim 15, wherein the composition is not cultured.

23. The method of claim 15, wherein the subject:
a) has acute myelogenous leukemia (AML), acute lymphoblastic leukemia (ALL), chronic myelogenous leukemia (CML), chronic lymphocytic leukemia (CLL), juvenile myelomonocytic leukemia, Hodgkin's lymphoma, non-Hodgkin's lymphoma, multiple myeloma, severe aplastic anemia, Fanconi's anemia, paroxysmal nocturnal hemoglobinuria (PNH), pure red cell aplasia, amegakaryocytosis/congenital thrombocytopenia, severe combined immunodeficiency syndrome (SCID), Wiskott-Aldrich syndrome, beta-thalassemia major, sickle cell disease, Hurler's syndrome, adrenoleukodystrophy, metachromatic leukodystrophy, myelodysplasia, refractory anemia, chronic myelomonocytic leukemia, agnogenic myeloid metaplasia, familial erythrophagocytic lymphohistiocytosis, or solid tumors;
b) has breast cancer, ovarian cancer, brain cancer, prostate cancer, lung cancer, colon cancer, skin cancer, liver cancer, pancreatic cancer, or sarcoma;
c) has received bone marrow ablative or non-myeolablative chemotherapy or radiation therapy; or
d) is a bone marrow donor.

24. The hematopoietic stem or progenitor cell of claim 1, wherein the cell is contacted with the one or more agents at a temperature of about 22° C. to about 39° C.

25. The therapeutic composition of claim 1, wherein the cell is contacted with the one or more agents at a temperature of about 35° C. to about 39° C.

26. The therapeutic composition of claim 6, wherein the cell is contacted with the one or more agents at a temperature of about 22° C. to about 39° C.

27. The therapeutic composition of claim 6, wherein the cell is contacted with the one or more agents at a temperature of about 35° C. to about 39° C.

28. The therapeutic composition of claim 6, wherein the population of cells is not expanded ex vivo.

29. A human hematopoietic stem or progenitor cell having CXCR4 gene expression of at least 30-fold greater compared to basal CXCR4 gene expression of a control hematopoietic stem or progenitor cell.

30. The human hematopoietic stem or progenitor cell of claim 29, wherein the hematopoietic stem or progenitor cell has at least 40-fold greater CXCR4 gene expression compared to basal CXCR4 gene expression.

31. A population of cells comprising the human hematopoietic stem or progenitor cell of claim 29.

32. The population of cells of claim 31, wherein the population comprises at least about 0.01% and no more than about 50% CD34+ cells.

33. The population of cells of claim 31, wherein the cells are ready for administration to a human subject in need thereof.

34. A therapeutic composition comprising the human hematopoietic stem or progenitor cell of claim 29.

35. The hematopoietic stem or progenitor cell of claim 1, wherein the one or more prostaglandin pathway agonists comprises 16,16-dimethyl-$PGE_2$.

36. The therapeutic composition of claim 9, wherein the one or more prostaglandin pathway agonists comprises 16,16-dimethyl-$PGE_2$.

37. The therapeutic composition according to claim 11, wherein the one or more prostaglandin pathway agonists comprises 16,16-dimethyl-$PGE_2$.

38. The method of claim 15, wherein the one or more prostaglandin pathway agonists comprises 16,16-dimethyl-$PGE_2$.

39. The therapeutic composition of claim 6, wherein the hematopoietic stem or progenitor cells have been contacted for a time of two hours to six hours with at least one of (i) one or more prostaglandin pathway agonists and (ii) one or more glucocorticoids.

40. The method of claim 15, wherein the hematopoietic stem or progenitor cells have been contacted with one or more prostaglandin pathway agonists and one or more glucocorticoids for a time of two hours to six hours.

* * * * *